United States Patent
Kase et al.

(10) Patent No.: US 12,102,002 B2
(45) Date of Patent: Sep. 24, 2024

(54) COMPOUND HAVING BENZAZOLE RING STRUCTURE, AND ORGANIC ELECTROLUMINESCENT DEVICE

(71) Applicant: HODOGAYA CHEMICAL CO., LTD., Tokyo (JP)

(72) Inventors: Kouki Kase, Tokyo (JP); Si-In Kim, Tokyo (JP); Ji-Yung Kim, Tokyo (JP); Yuta Hirayama, Tokyo (JP); Kazuyuki Suruga, Tokyo (JP); Shuichi Hayashi, Tokyo (JP)

(73) Assignee: HODOGAYA CHEMICAL CO., LTD., Tokyo (JP)

( * ) Notice: Subject to any disclaimer, the term of this patent is extended or adjusted under 35 U.S.C. 154(b) by 663 days.

(21) Appl. No.: 17/414,601

(22) PCT Filed: Feb. 12, 2020

(86) PCT No.: PCT/JP2020/005410
§ 371 (c)(1),
(2) Date: Jun. 16, 2021

(87) PCT Pub. No.: WO2020/166630
PCT Pub. Date: Aug. 20, 2020

(65) Prior Publication Data
US 2022/0052273 A1 Feb. 17, 2022

(30) Foreign Application Priority Data
Feb. 13, 2019 (JP) .................................. 2019-023121

(51) Int. Cl.
*H10K 85/60* (2023.01)
(52) U.S. Cl.
CPC ....... *H10K 85/6572* (2023.02); *H10K 85/622* (2023.02); *H10K 85/624* (2023.02);
(Continued)

(58) Field of Classification Search
None
See application file for complete search history.

(56) References Cited

U.S. PATENT DOCUMENTS

| | | | |
|---|---|---|---|
| 4,892,953 A | 1/1990 | Arnold et al. | |
| 5,639,914 A | 6/1997 | Tomiyama et al. | |

(Continued)

FOREIGN PATENT DOCUMENTS

| | | | |
|---|---|---|---|
| CA | 2051518 A1 | 4/1992 | |
| CN | 108530437 A | 9/2018 | |

(Continued)

OTHER PUBLICATIONS

Abdellaoui et al., "Palladium-catalyzed non-directed C—H bond arylation of difluorobenzenes and dichlorobenzenes bearing benzoxazole or benzothiazole", Catalysis Communications, 2015, (Available online Aug. 5, 2015), pp. 13-16, XP055974045.

(Continued)

*Primary Examiner* — Robert S Loewe
(74) *Attorney, Agent, or Firm* — Birch, Stewart, Kolasch & Birch, LLP

(57) ABSTRACT

An object of the present invention is to provide, as a material for a highly efficient and highly durable organic EL element, an organic compound that has excellent properties, including excellent electron-injecting/transporting capability, hole-blocking capability, and high stability in the form of a thin film. Another object of the present invention is to provide a highly efficient and highly durable organic EL element by using this compound. The present invention focuses on the properties of the benzazole ring, which has affinity for electrons, and specifically focuses on the capability of its nitrogen atom to coordinate to a metal and also on excellent heat resistance. The inventors have thus designed and chemically synthesized various compounds having a benzazole ring structure, and then experimentally (Continued)

← 9 Cathode
← 8 Electron-injecting layer
← 7 Electron-transporting layer
← 6 Hole-blocking layer
← 5 Light-emitting layer
← 4 Hole-transporting layer
← 3 Hole-injecting layer
← 2 Transparent Anode
← 1 Glass Substrate produced organic EL elements including the compounds, followed by thoroughly evaluating the characteristics thereof. As a result, it has been found that it is possible to obtain an organic EL element having excellent properties by using a specific compound having a benzazole ring structure.

9 Claims, 14 Drawing Sheets

(52) U.S. Cl.
CPC ......... *H10K 85/626* (2023.02); *H10K 85/654* (2023.02); *H10K 85/6574* (2023.02); *H10K 85/6576* (2023.02)

(56) References Cited

U.S. PATENT DOCUMENTS

| | | | |
|---|---|---|---|
| 5,792,557 | A | 8/1998 | Nakaya et al. |
| 5,869,199 | A | 2/1999 | Kido |
| 6,878,469 | B2 | 4/2005 | Yoon et al. |
| 8,735,597 | B2 | 5/2014 | Nomura et al. |
| 9,123,897 | B2 | 9/2015 | Yokoyama et al. |
| 9,199,966 | B2 | 12/2015 | Kim et al. |
| 9,802,961 | B2 | 10/2017 | Clark et al. |
| 2005/0065340 | A1 | 3/2005 | Arruda et al. |
| 2005/0101647 | A1 | 5/2005 | Oda et al. |
| 2014/0239269 | A1 | 8/2014 | Jeong et al. |
| 2018/0354913 | A1 | 12/2018 | Jung et al. |
| 2020/0010460 | A1 | 1/2020 | Ryu et al. |

FOREIGN PATENT DOCUMENTS

| | | |
|---|---|---|
| CN | 108822096 A | 11/2018 |
| EP | 1 852 488 A1 | 11/2007 |
| EP | 2 684 932 A1 | 1/2014 |
| GB | 671939 A | 5/1952 |
| GB | 1080246 A | 8/1967 |
| JP | 42-15938 B1 | 9/1967 |
| JP | 4-264074 A | 9/1992 |
| JP | 6-228550 A | 8/1994 |
| JP | 2005-514382 A | 5/2005 |
| JP | 2016-15388 A | 1/2016 |
| JP | 2016-58205 A | 4/2016 |
| JP | 2018-532688 A | 11/2018 |
| KR | 10-2015-0052969 A | 5/2015 |
| WO | WO 03/045929 A1 | 6/2003 |
| WO | WO 2010/126270 A1 | 11/2010 |
| WO | WO 2019/166206 A1 | 9/2019 |
| WO | WO 2019/191666 A1 | 10/2019 |
| WO | WO 2020/009519 A1 | 1/2020 |

OTHER PUBLICATIONS

Kapileswar et al., "Cooperative Catalysis by Palladium-Nickel Binary Nanocluster for Suzuki-Miyaura Reaction of Ortho-Heterocycle-Tethered Sterically Hindered Aryl Bromides", Org. Lett., vol. 16, No. 9, 2014, (Published Apr. 10, 2014), pp. 2334-2337, XP055959132.
Bellina et al., "Colourless p-phenylene-spaced bis-azoles for luminescent concentrators," Dyes and Pigments, vol. 134, 2016, pp. 118-128.
Endo et al., "Efficient up-conversion of triplet excitons into a singlet state and its application for organic light emitting diodes," Applied Physics Letters, vol. 98, No. 083302, 2011, pp. 1-3.
Evindar et al., "Parallel Synthesis of a Library of Benzoxazoles and Benzothiazoles Using Ligand-Accelerated Copper-Catalyzed Cydizations of ortho-Halobenzanilides," J. Org. Chem., vol. 71, No. 5, 2006, pp. 1802-1808.
Hosokawa et al., "Development of Styryl-Based Light Emitting Material," Proceedings of the 9th Meeting of the Japan Society of Applied Physics, 2001, pp. 55-61.
International Search Report (PCT/ISA/210) issued in PCT/JP2020/005410, dated Apr. 14, 2020.
Journal of Molecular Electronics and Bioelectronics of the Japan Society of Applied Physics, vol. 11, No. 1, 2000, pp. 13-19.
Mayo et al., "Synthesis of Benzoxazoles from 2-Aminophenols and β-Diketones Using a Combined Catalyst of Brønsted Acid and Copper Iodide," The Journal of Organic Chemistry, vol. 79, 2014, pp. 6310-6314.
Wakimoto, "Optimization of driving lifetime durability in organic LED devices using phosphorescent guest emitter," Proceedings of the 9th Meeting of the Japan Society of Applied Physics, 2001, pp. 23-31.
Watanabe et al., "Organic LEDs using Hexaphenylbenzene Derivatives," Proceedings of the 50th Meeting of the Japan Society of Applied Physics and Related Societies, 28p-A-6, 2003, p. 1413.
"Benzonitrile, 4-[6-(2, 3, 4-Trimethoxyphenyl)-2-benzoxazolyl]," Database Registry [Online], CAS Registry No. 924596-18-9,924553-90-2,924544-54-7, 2007, retrieved from STN, 3 pages total.

(Compound-201)   (Compound-202)
(Compound-203)   (Compound-204)

← 9  Cathode
← 8  Electron-injecting layer
← 7  Electron-transporting layer
← 6  Hole-blocking layer
← 5  Light-emitting layer
← 4  Hole-transporting layer
← 3  Hole-injecting layer
← 2  Transparent Anode
← 1  Glass Substrate

COMPOUND HAVING BENZAZOLE RING STRUCTURE, AND ORGANIC ELECTROLUMINESCENT DEVICE

TECHNICAL FIELD

The present invention relates to a compound suitable for organic electroluminescent elements (hereinafter abbreviated as "organic EL elements"), which are self-emissive elements favorably used in various display devices, and also relates to an element. More particularly, the present invention relates to a compound having a benzazole ring structure and an organic EL element including the compound.

BACKGROUND ART

Since organic EL elements are self-emissive elements, they have larger brightness and better viewability than elements including liquid crystals, thus they can provide a clearer display. For these reasons, active studies have been carried out on organic EL elements.

In 1987, C. W. Tang et al. of Eastman Kodak Company developed an element having a layered structure in which various functions were assigned to different materials, and thus made a practical organic EL element including organic materials. They made an organic EL element having a layered structure including a layer of a fluorescent substance capable of transporting electrons and a layer of an organic substance capable of transporting holes, and injected both charges into the layer of the fluorescent substance to thereby cause the layer to emit light, and the organic EL element thus achieved a luminance as high as 1,000 cd/m$^2$ or more at a voltage of 10 V or less (see Patent Literatures 1 and 2, for example).

Organic EL elements have been heretofore much improved to put them to practical use. Electroluminescent elements have been suggested in which an anode, a hole-injecting layer, a hole-transporting layer, a light-emitting layer, an electron-transporting layer, an electron-injecting layer, and a cathode are sequentially provided on a substrate to subdivide various functions in the multi-layered structure even further, and such electroluminescent elements successfully have high efficiency and durability (see Non-Patent Literature 1, for example).

To further increase luminous efficacy, attempts have been made to utilize triplet excitons, and the utilization of phosphorescent compounds has been investigated (see Non-Patent Literature 2, for example).

Moreover, elements that utilize light emission by thermally activated delayed fluorescence (TADF) have also been developed. In 2011, Adachi et al. from Kyushu University achieved a result of an external quantum efficiency of 5.3% by an element including a thermally activated delayed fluorescence material (see Non-Patent Literature 3, for example).

The light-emitting layer can also be prepared by doping a charge-transporting compound, generally called a host material, with a fluorescent compound, a phosphorescent compound, or a material that radiates delayed fluorescence. As stated in the non-patent literature above, the selection of the organic materials in an organic EL element greatly affects the characteristics of that element, such as efficiency and durability (see Non-Patent Literature 2, for example).

In an organic EL element, the charges injected from both electrodes recombine in the light-emitting layer, thereby producing light emission, and how efficiently the both charges, i.e., the holes and the electrons, are passed to the light-emitting layer is of importance. For this purpose, it is necessary to enhance the electron-injecting capability and increase the electron mobility to thereby increase the probability that holes and electrons recombine in the light-emitting layer. In other words, highly efficient light emission can be achieved if an environment that increases the probability of the recombination even more can be created by confining holes transported from the anode side in the light-emitting layer, preventing deterioration of the electron-transporting layer, and confining excitons generated in the light-emitting layer. Therefore, the functions of the electron-transporting material are important, and there is a need for an electron-transporting material that has great electron-injecting capability, high electron mobility, high hole-blocking capability, and high durability against holes.

Moreover, heat resistance and amorphousness of the materials are also important for element lifespan. A material with low heat resistance thermally decomposes, due to heat generated during driving the element, even at a low temperature, and thus the material deteriorates. A film made of a material with low amorphousness causes crystallization thereof even in a short period of time to result in deterioration of the element. Thus, the materials to be used are required to have high heat resistance and good amorphousness.

Tris(8-hydroxyquinoline)aluminum (hereinafter abbreviated as Alq3), which is a typical light emitting material, is also commonly used as an electron-transporting material. However, it provides low electron mobility and has a work function of 5.6 eV, and therefore it cannot be said that Alq3 has sufficient hole-blocking capability.

Compounds having a benzotriazole structure have been suggested as compounds improved in the properties including the electron-injecting capability and the electron mobility (see Patent Literature 3, for example). Elements having an electron-transporting layer including such a compound have improved properties including luminous efficacy; however, these properties are still insufficient. Therefore, there is a demand for a further decrease in driving voltage and a further increase in luminous efficacy.

Also, 3-(4-biphenylyl)-4-phenyl-5-(4-t-butylphenyl)-1,2,4-triazole (hereinafter abbreviated as TAZ) has been suggested as an electron-transporting material with excellent hole-blocking capability (see Patent Literature 4, for example).

TAZ has a work function as high as 6.6 eV and has high hole-blocking capability. Therefore, TAZ is used for an electron transportable, hole-blocking layer stacked on the cathode side of a fluorescent or phosphorescent light-emitting layer produced by vacuum deposition or coating, and TAZ thus contributes to an increase in the efficiency of an organic EL element (see Non-Patent Literature 4, for example).

However, low electron-transporting capability is a critical problem with TAZ, and it is necessary to combine TAZ with an electron-transporting material having higher electron-transporting capability when producing an organic EL element (see Non-Patent Literature 5, for example).

2,9-dimethyl-4,7-diphenyl-1,10-phenanthroline (BCP), which is known as an electron-transporting material, also has a work function as high as 6.7 eV and has high hole-blocking capability. However, BCP has a glass transition point (Tg) as low as 83° C., which results in poor stability of a thin film made of it, and therefore cannot be said to be capable of sufficiently functioning as a hole-blocking layer.

All of these materials have insufficient stability in the form of a film or have insufficient hole-blocking capability. In view of improving characteristics of an organic EL element, there is a demand for an organic compound that has excellent electron-injecting/transporting capability and hole-blocking capability, and also has high stability in the form of a thin film.

CITATION LIST

Patent Literature

Patent Literature 1: U.S. Pat. No. 5,792,557
Patent Literature 2: U.S. Pat. No. 5,639,914
Patent Literature 3: U.S. Pat. No. 9,123,897
Patent Literature 4: U.S. Pat. No. 5,869,199
Patent Literature 5: U.S. Pat. No. 8,735,597
Patent Literature 6: U.S. Pat. No. 9,802,961
Patent Literature 7: EP 2684932
Patent Literature 8: U.S. Pat. No. 9,199,966
Patent Literature 9: U.S. Pat. No. 6,878,469

Non-Patent Literature

Non-Patent Literature 1: Proceedings of the 9th Meeting of the Japan Society of Applied Physics, pp. 55-61 (2001)
Non-Patent Literature 2: Proceedings of the 9th Meeting of the Japan Society of Applied Physics, pp. 23-31 (2001)
Non-Patent Literature 3: Appl. Phys. Lett., 98, 083302 (2011)
Non-Patent Literature 4: Proceedings of the 50th Meeting of the Japan Society of Applied Physics and Related Societies, 28p-A-6, p. 1413 (2003)
Non-Patent Literature 5: Journal of Molecular Electronics and Bioelectronics of the Japan Society of Applied Physics, Vol. 11, No. 1, pp. 13-19 (2000)
Non-Patent Literature 6: J. Org. chcm., 71, 1802 (2006)
Non-Patent Literature 7: J. Org. chcm., 79, 6310 (2014)

SUMMARY OF INVENTION

An object of the present invention is to provide, as a material for a highly efficient and highly durable organic EL element, an organic compound having excellent properties, including excellent electron-injecting/transporting capability, hole-blocking capability, and high stability in the form of a thin film. Furthermore, another object of the present invention is to provide a highly efficient and highly durable organic EL element by using this compound.

An organic compound to be provided by the present invention should have the following physical properties: (1) good electron-injecting properties, (2) high electron mobility, (3) excellent hole-blocking capability, (4) stability in the form of a thin film, and (5) excellent heat resistance. Moreover, an organic EL element to be provided by the present invention should have the following physical characteristics: (1) high luminous efficacy and high power efficiency, (2) a low voltage for the start of light emission, (3) a low driving voltage in actual use, and (4) a long lifespan.

To achieve the above-described objects, the inventors of the present invention have focused on the properties of the benzazole ring, which has affinity for electrons, and specifically focused on the capability of its nitrogen atom to coordinate to a metal and also on excellent heat resistance. The inventors have thus designed and chemically synthesized various compounds having a benzazole ring structure, and then experimentally produced organic EL elements including the compounds, followed by thoroughly evaluating the characteristics thereof, and thus, the present invention has been accomplished.

1) Specifically, the present invention is directed to a compound having a benzazole ring structure and represented by the general formula (a-1):

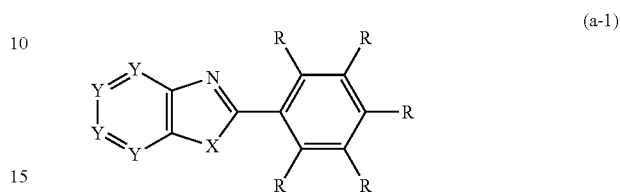

where a plurality of R are the same or different, and represent a group represented by the structural formula (b-1) below, a hydrogen atom, a deuterium atom, a fluorine atom, a chlorine atom, a cyano group, a nitro group, a trimethylsilyl group, a triphenylsilyl group, a diphenylphosphinyl group, a diphenylphosphine oxide group, a substituted or unsubstituted aromatic hydrocarbon group, a substituted or unsubstituted aromatic heterocyclic group, a substituted or unsubstituted fused polycyclic aromatic group, a linear or branched alkyl group having 1 to 6 carbon atoms and optionally having a substituent, a cycloalkyl group having 5 to 10 carbon atoms and optionally having a substituent, a linear or branched alkenyl group having 2 to 6 carbon atoms and optionally having a substituent, a linear or branched alkyloxy group having 1 to 6 carbon atoms and optionally having a substituent, or a cycloalkyloxy group having 5 to 10 carbon atoms and optionally having a substituent, X represents an oxygen atom or a sulfur atom, a plurality of Y are the same or different, and represent a carbon atom having R, or a nitrogen atom, and at least one R is a group represented by the structural formula (b-1):

where $L_1$ and $L_2$ are the same or different, and represent a single bond, a substituted or unsubstituted aromatic hydrocarbon group, a substituted or unsubstituted aromatic heterocyclic group, or a substituted or unsubstituted fused polycyclic aromatic group, n is an integer 1 or 2, and the dashed line indicates a binding site.

2) Furthermore, the present invention is directed to the compound having a benzazole ring structure as set forth in 1) above and represented by the general formula (a-2):

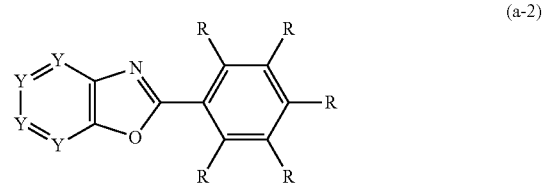

where R and Y are as defined in the general formula (a-1).

3) Furthermore, the present invention is directed to the compound having a benzazole ring structure as set forth in 2) above and represented by the general formula (a-3):

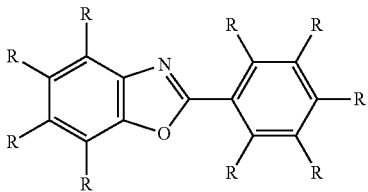

where R is as defined in the general formula (a-1).

4) Furthermore, the present invention is directed to the compound having a benzazole ring structure as set forth in 3) above and represented by the general formula (a-4):

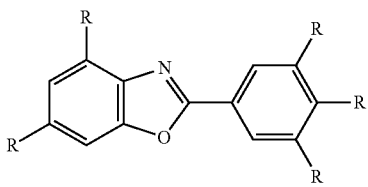

where R is as defined in the general formula (a-1).

5) Furthermore, the present invention is directed to the compound having a benzazole ring structure as set forth in 4) above and represented by the general formula (a-5):

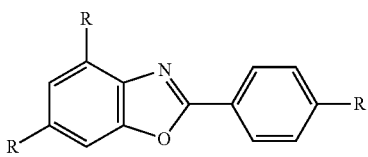

where R is as defined in the general formula (a-1).

6) Furthermore, the present invention is directed to the compound having a benzazole ring structure as set forth in 1) above and represented by the general formula (a-6):

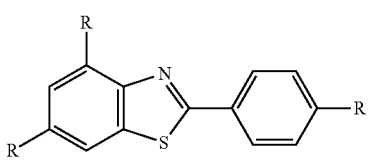

where R is as defined in the general formula (a-1).

7) Furthermore, the present invention is directed to the compound having a benzazole ring structure as set forth in 6) above and represented by the general formula (a-7):

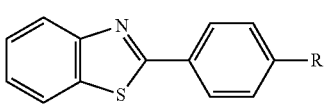

where R is as defined in the general formula (a-1).

8) Furthermore, the present invention is directed to the compound having a benzazole ring structure as set forth in any one of 1) to 7) above, wherein n in the structural formula (b-1) is an integer 1.

9) Furthermore, the present invention is directed to the compound having a benzazole ring structure as set forth in any one of 1) to 8) above, wherein $L_2$ in the structural formula (b-1) is a substituted or unsubstituted phenylene group or a substituted or unsubstituted biphenylene group.

10) Also, the present invention is directed to an organic EL element comprising a pair of electrodes and one or more organic layers sandwiched therebetween, wherein the compound having a benzazole ring structure as set forth in any one of 1) to 9) above is included in at least one of the organic layers.

11) Furthermore, the present invention is directed to the organic EL element as set forth in 10) above, wherein the organic layer including the compound having a benzazole ring structure is an electron-transporting layer.

12) Furthermore, the present invention is directed to the organic EL element as set forth in 10) above, wherein the organic layer including the compound having a benzazole ring structure is a hole-blocking layer.

13) Furthermore, the present invention is directed to the organic EL element as set forth in 10) above, wherein the organic layer including the compound having a benzazole ring structure is a light-emitting layer.

14) Furthermore, the present invention is directed to the organic EL element as set forth in 10) above, wherein the organic layer including the compound having a benzazole ring structure is an electron-injecting layer.

Specific examples of the "aromatic hydrocarbon group", the "aromatic heterocyclic group", and the "fused polycyclic aromatic group" of the "substituted or unsubstituted aromatic hydrocarbon group", the "substituted or unsubstituted aromatic heterocyclic group", and the "substituted or unsubstituted fused polycyclic aromatic group" represented by R in the general formula (a-1) include a phenyl group, a biphenylyl group, a terphenylyl group, a naphthyl group, an anthracenyl group, a phenanthrenyl group, a fluorenyl group, a spirobifluorenyl group, an indenyl group, a pyrenyl group, a perylenyl group, a fluoranthenyl group, a triphenylenyl group, a pyridyl group, a pyrimidinyl group, a triazinyl group, a furyl group, a pyrrolyl group, a thienyl group, a quinolyl group, an isoquinolyl group, a benzofuranyl group, a benzothienyl group, an indolyl group, a carbazolyl group, a benzooxazolyl group, a benzothiazolyl group, an azafluorenyl group, a diazafluorenyl group, an azaspirobifluorenyl group, a diazaspirobifluorenyl group, a quinoxalinyl group, a benzimidazolyl group, a pyrazolyl group, a dibenzofuranyl group, a dibenzothienyl group, a naphthyridinyl group, a phenanthrolinyl group, an acridinyl group, and a carbolinyl group; and also an aryl group having 6 to 30 carbon atoms and a heteroaryl group having 2 to 20 carbon atoms.

Specific examples of the "substituent" of the "substituted aromatic hydrocarbon group", the "substituted aromatic heterocyclic group", and the "substituted fused polycyclic aromatic group" represented by R in the general formula (a-1) include: a deuterium atom, a cyano group, and a nitro group; halogen atoms such as a fluorine atom, a chlorine atom, a bromine atom, and an iodine atom; silyl groups such as a trimethylsilyl group and a triphenylsilyl group; linear or branched alkyl groups having 1 to 6 carbon atoms, such as a methyl group, an ethyl group, and a propyl group; linear or branched alkyloxy groups having 1 to 6 carbon atoms such as a methyloxy group, an ethyloxy group, and a propyloxy group; alkenyl groups such as a vinyl group and an allyl group; aryloxy groups such as a phenyloxy group and a tolyloxy group; arylalkyloxy groups such as a benzyloxy group and a phenethyloxy group; aromatic hydrocarbon groups or fused polycyclic aromatic groups such as a phenyl group, a biphenylyl group, a terphenylyl group, a naphthyl group, an anthracenyl group, a phenanthrenyl group, a fluorenyl group, a spirobifluorenyl group, an indenyl group, a pyrenyl group, a perylenyl group, a fluoranthenyl group, and a triphenylenyl group; and aromatic heterocyclic groups such as a pyridyl group, a pyrimidinyl group, a triazinyl group, a thienyl group, a furyl group, a pyrrolyl group, a quinolyl group, an isoquinolyl group, a benzofuranyl group, a benzothienyl group, an indolyl group, a carbazolyl group, a benzooxazolyl group, a benzothiazolyl group, a quinoxalinyl group, a benzimidazolyl group, a pyrazolyl group, a dibenzofuranyl group, a dibenzothienyl group, and a carbolinyl group. These substituents may further be substituted by any of the substituents listed above as examples. Moreover, such a substituent and the benzene ring substituted therewith, or a plurality of the substituents that substitute the same benzene ring may be bonded to each other via a single bond, a substituted or unsubstituted methylene group, an oxygen atom, or a sulfur atom to form a ring.

Specific examples of the "carbon atom having a linear or branched alkyl group having 1 to 6 carbon atoms", the "carbon atom having a cycloalkyl group having 5 to 10 carbon atoms", and the "carbon atom having a linear or branched alkenyl group having 2 to 6 carbon atoms" of the "carbon atom having a linear or branched alkyl group having 1 to 6 carbon atoms and optionally having a substituent", the "carbon atom having a cycloalkyl group having 5 to 10 carbon atoms and optionally having a substituent", and the "carbon atom having a linear or branched alkenyl group having 2 to 6 carbon atoms and optionally having a substituent" represented by R in the general formula (a-1) include a methyl group, an ethyl group, an n-propyl group, an isopropyl group, an n-butyl group, an isobutyl group, a tert-butyl group, an n-pentyl group, an isopentyl group, a neopentyl group, an n-hexyl group, a cyclopentyl group, a cyclohexyl group, a 1-adamantyl group, a 2-adamantyl group, a vinyl group, an allyl group, an isopropenyl group, and a 2-butenyl group. Such a substituent and the benzene ring substituted therewith, or a plurality of the substituents that substitute the same benzene ring may be bonded to each other via a single bond, a substituted or unsubstituted methylene group, a substituted or unsubstituted amino group, an oxygen atom, or a sulfur atom to form a ring.

Examples of the "substituent" of the "linear or branched alkyl group having 1 to 6 carbon atoms and optionally having a substituent", the "cycloalkyl group having 5 to 10 carbon atoms and optionally having a substituent", and the "linear or branched alkenyl group having 2 to 6 carbon atoms and optionally having a substituent" represented by R in the general formula (a-1) include the same as those listed above as examples of the "substituent" of the "substituted aromatic hydrocarbon group", the "substituted aromatic heterocyclic group", and the "substituted fused polycyclic aromatic group" represented by R in the general formula (a-1). The same holds true for the form that the substituent may be in.

Specific examples of the "carbon atom having a linear or branched alkyloxy group having 1 to 6 carbon atoms" and the "carbon atom having a cycloalkyloxy group having 5 to 10 carbon atoms" of the "carbon atom having a linear or branched alkyloxy group having 1 to 6 carbon atoms and optionally having a substituent" and the "carbon atom having a cycloalkyloxy group having 5 to 10 carbon atoms and optionally having a substituent" represented by R in the general formula (a-1) include a methyloxy group, an ethyloxy group, an n-propyloxy group, an isopropyloxy group, an n-butyloxy group, a tert-butyloxy group, an n-pentyloxy group, an n-hexyloxy group, a cyclopentyloxy group, a cyclohexyloxy group, a cycloheptyloxy group, a cyclooctyloxy group, a 1-adamantyloxy group, and a 2-adamantyloxy group. Such a substituent and the benzene ring substituted therewith, or a plurality of the substituents that substitute the same benzene ring may be bonded to each other via a single bond, a substituted or unsubstituted methylene group, a substituted or unsubstituted amino group, an oxygen atom, or a sulfur atom to form a ring.

Examples of the "substituent" of the "linear or branched alkyloxy group having 1 to 6 carbon atoms and optionally having a substituent" and the "cycloalkyloxy group having 5 to 10 carbon atoms and optionally having a substituent" represented by R in the general formula (a-1) include the same as those listed above as examples of the "substituent" of the "substituted aromatic hydrocarbon group", the "substituted aromatic heterocyclic group", and the "substituted fused polycyclic aromatic group" represented by R in the general formula (a-1). The same holds true for the forms that the substituent may be in.

Examples of the "aromatic hydrocarbon group", the "aromatic heterocyclic group", and the "fused polycyclic aromatic group" of the "substituted or unsubstituted aromatic hydrocarbon group", the "substituted or unsubstituted aromatic heterocyclic group", and the "substituted or unsubstituted fused polycyclic aromatic group" represented by $L_1$ and $L_2$ in the structural formula (b-1) may be groups obtained by removing one hydrogen atom from those listed above as examples of the "aromatic hydrocarbon group", the "aromatic heterocyclic group", and the "fused polycyclic aromatic group" of the "substituted or unsubstituted aromatic hydrocarbon group", the "substituted or unsubstituted aromatic heterocyclic group", and the "substituted or unsubstituted fused polycyclic aromatic group" represented by R in the general formula (a-1). The same holds true for the forms that the substituent may be in.

Examples of the "substituent" of the "substituted aromatic hydrocarbon group", the "substituted aromatic heterocyclic group", and the "substituted fused polycyclic aromatic group" represented by $L_1$ and $L_2$ in the structural formula (b-1) include the same as those listed above as examples of the "substituent" of the "substituted aromatic hydrocarbon group", the "substituted aromatic heterocyclic group", and the "substituted fused polycyclic aromatic group" represented by R in the general formula (a-1). The same holds true for the forms that the substituent may be in.

The compound having a benzazole ring structure and represented by the general formula (a-1) above are suitable for use in the organic EL element of the present invention, and can be used as a constituent material for an electron-injecting layer, an electron-transporting layer, or a hole-blocking layer of the organic EL element. This compound is particularly preferable as a material for an electron-injecting layer or an electron-transporting layer due to its large electron mobility.

The organic EL element of the present invention includes an organic EL element material that has excellent electron-injecting/transporting capability, excellent stability in the form of a thin film, and durability. Therefore, compared with a conventional organic EL element, the organic EL element of the present invention has improved efficiency in terms of transporting electrons from the electron-transporting layer to the light-emitting layer and hence improved luminous efficacy, as well as a reduced driving voltage and hence improved durability of the organic EL element. Accordingly, the organic EL element of the present invention can achieve high efficiency, a low driving voltage, and a long lifespan.

The compound having a benzazole ring structure of the present invention has the properties including: (1) good electron-injecting properties, (2) high electron mobility, (3) excellent hole-blocking capability, (4) stability in the form of a thin film, and (5) excellent heat resistance. The organic EL element of the present invention has the properties including: (6) high luminous efficacy, (7) a low voltage for the start of light-emission, (8) a low driving voltage in actual use, and (9) a long lifespan.

The compound having a benzazole ring structure of the present invention has good electron-injecting properties and high electron mobility. Therefore, an organic EL element having an electron-injecting layer and/or an electron-transporting layer including the compound of the present invention as an electron-injecting material and/or an electron-transporting material has improved efficiency in terms of transporting electrons to the light-emitting layer and hence improved luminous efficacy, and also has a lower driving voltage and hence improved durability.

The compound having a benzazole ring structure of the present invention is characterized by excellent hole-blocking capability and electron-transporting capability, stability in the form of a thin film, and capability to confine excitons generated in a light-emitting layer. Accordingly, an organic EL element having a hole-blocking layer produced by using the compound as a hole blocking material has high luminous efficacy because the probability of recombination of holes and electrons is increased to thereby suppress the heat deactivation, and also has an increased maximum luminance because the driving voltage is reduced to thereby improve the current resistance.

The compound having a benzazole ring structure of the present invention has excellent electron-transporting capability and a wide band gap. Accordingly, an organic EL element having a light-emitting layer produced by using the compound of the present invention as a host material has a reduced driving voltage and hence improved luminous efficacy when the light-emitting layer also contains a fluorescent emitter, a phosphorescent emitter, or a delayed fluorescent body, which are called dopants.

Thus, the compound having a benzazole ring structure of the present invention is useful as a material for an electron-injecting layer, an electron-transporting layer, a hole-blocking layer, or a light-emitting layer of an organic EL element, and thus can improve the luminous efficacy, the driving voltage, and the durability of conventional organic EL elements.

DESCRIPTION OF EMBODIMENTS

Figure 1:
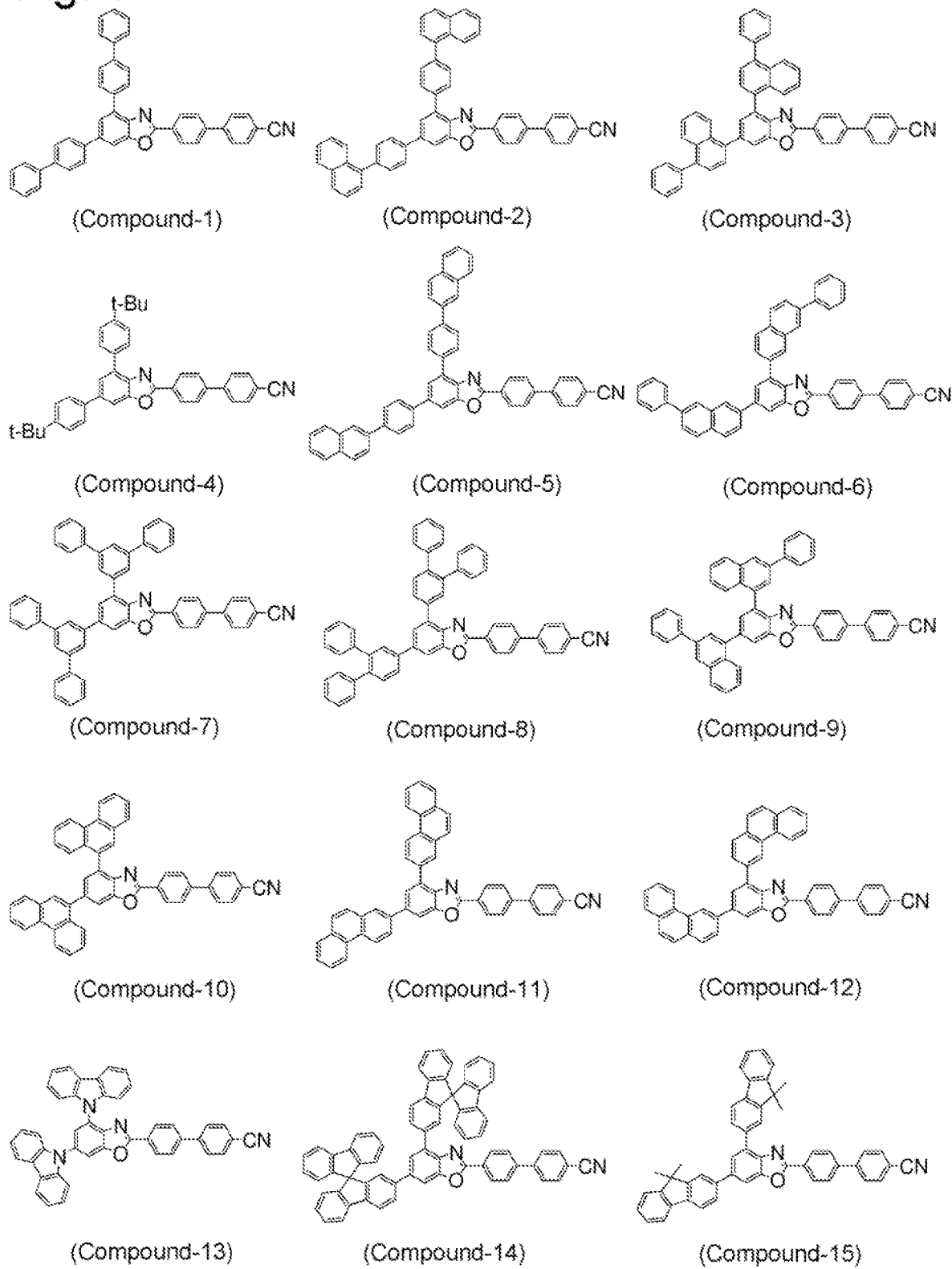
FIG. 1 shows the structures of Compounds 1 to 15 as examples of the compound having a benzazole ring structure represented by the general formula (a-1).
Figure 2:
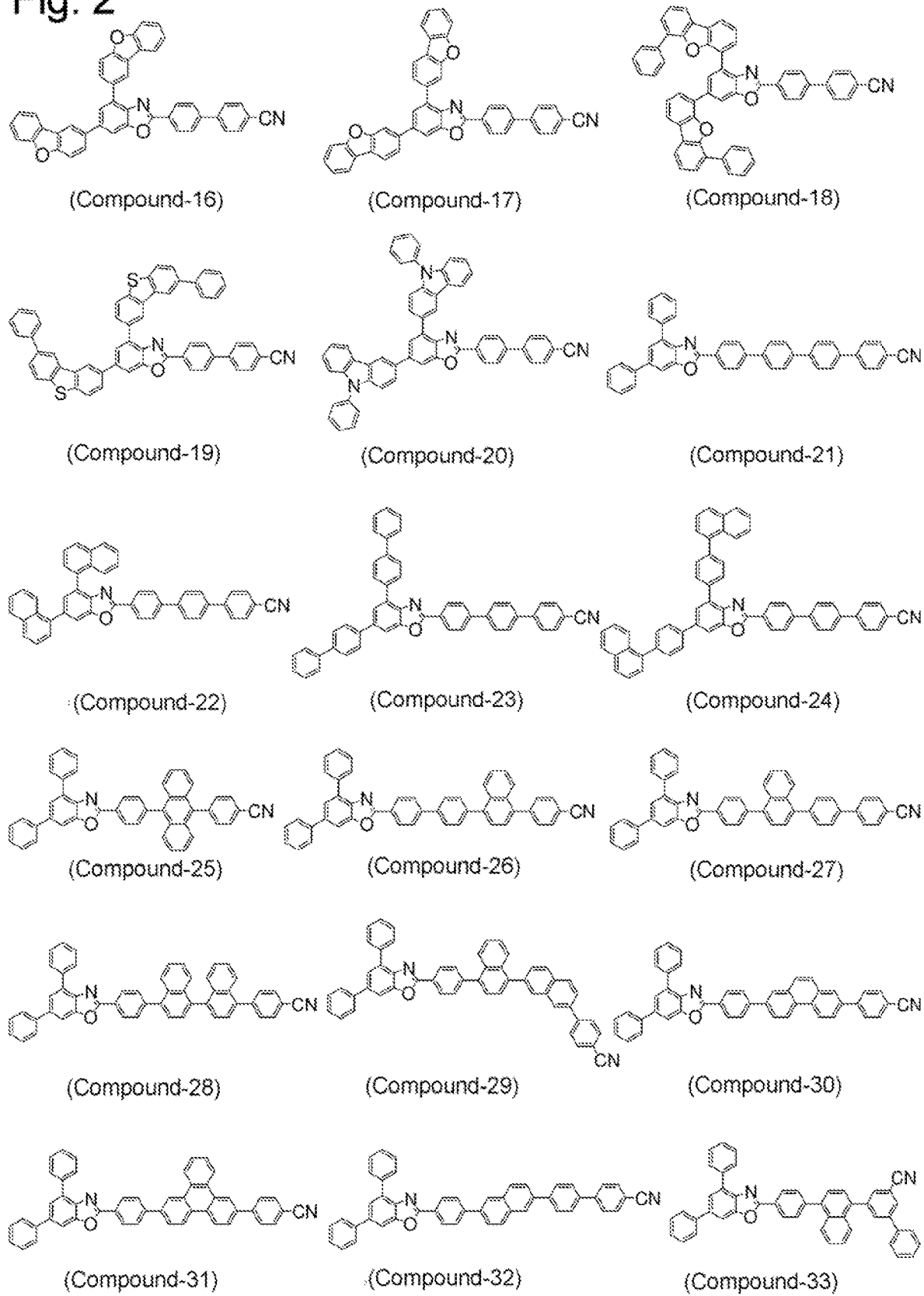
FIG. 2 shows the structures of Compounds 16 to 33 as examples of the compound having a benzazole ring structure represented by the general formula (a-1).
Figure 3:
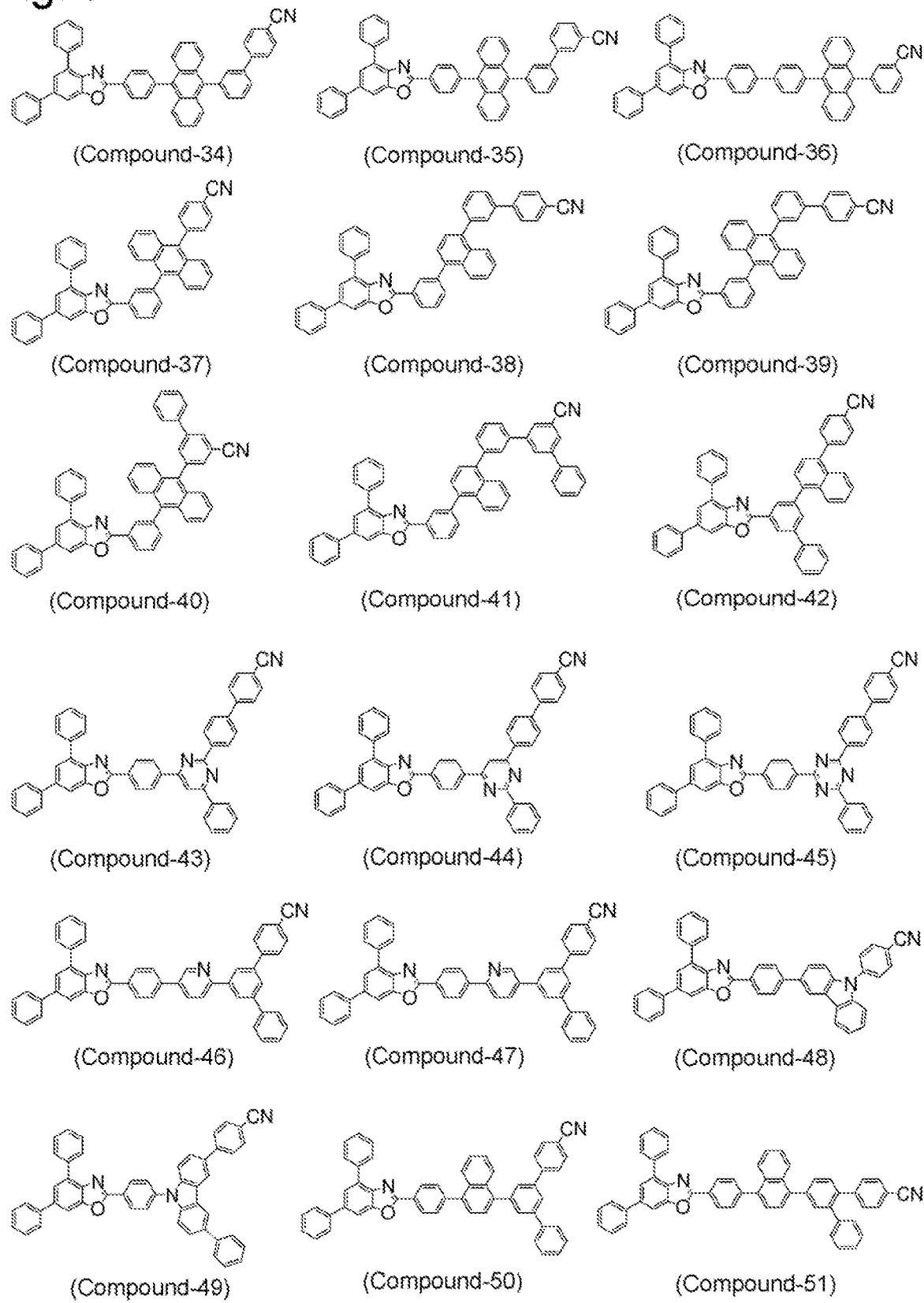
FIG. 3 shows the structures of Compounds 34 to 51 as examples of the compound having a benzazole ring structure represented by the general formula (a-1).
Figure 4:
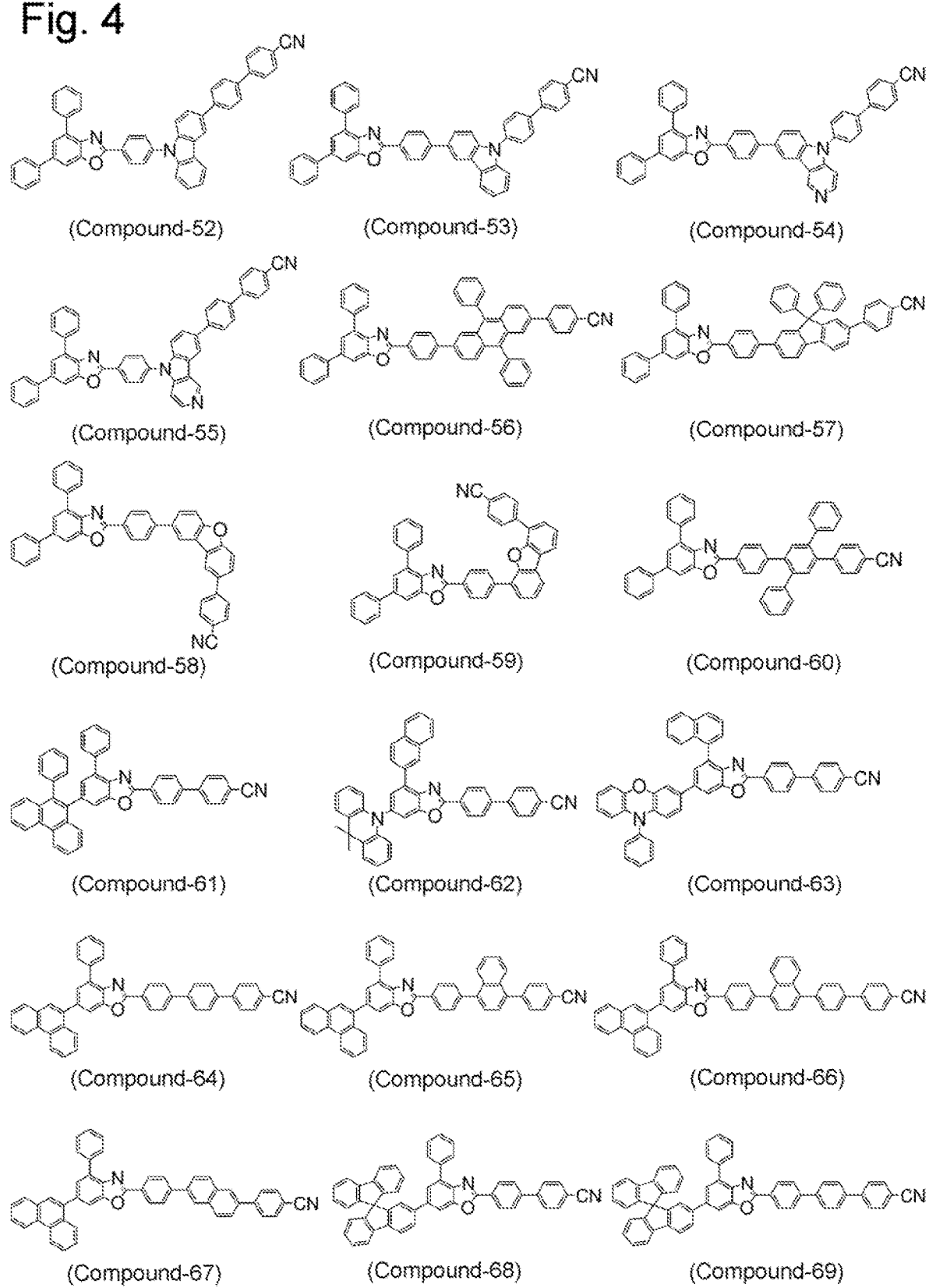
FIG. 4 shows the structures of Compounds 52 to 69 as examples of the compound having a benzazole ring structure represented by the general formula (a-1).
Figure 5:
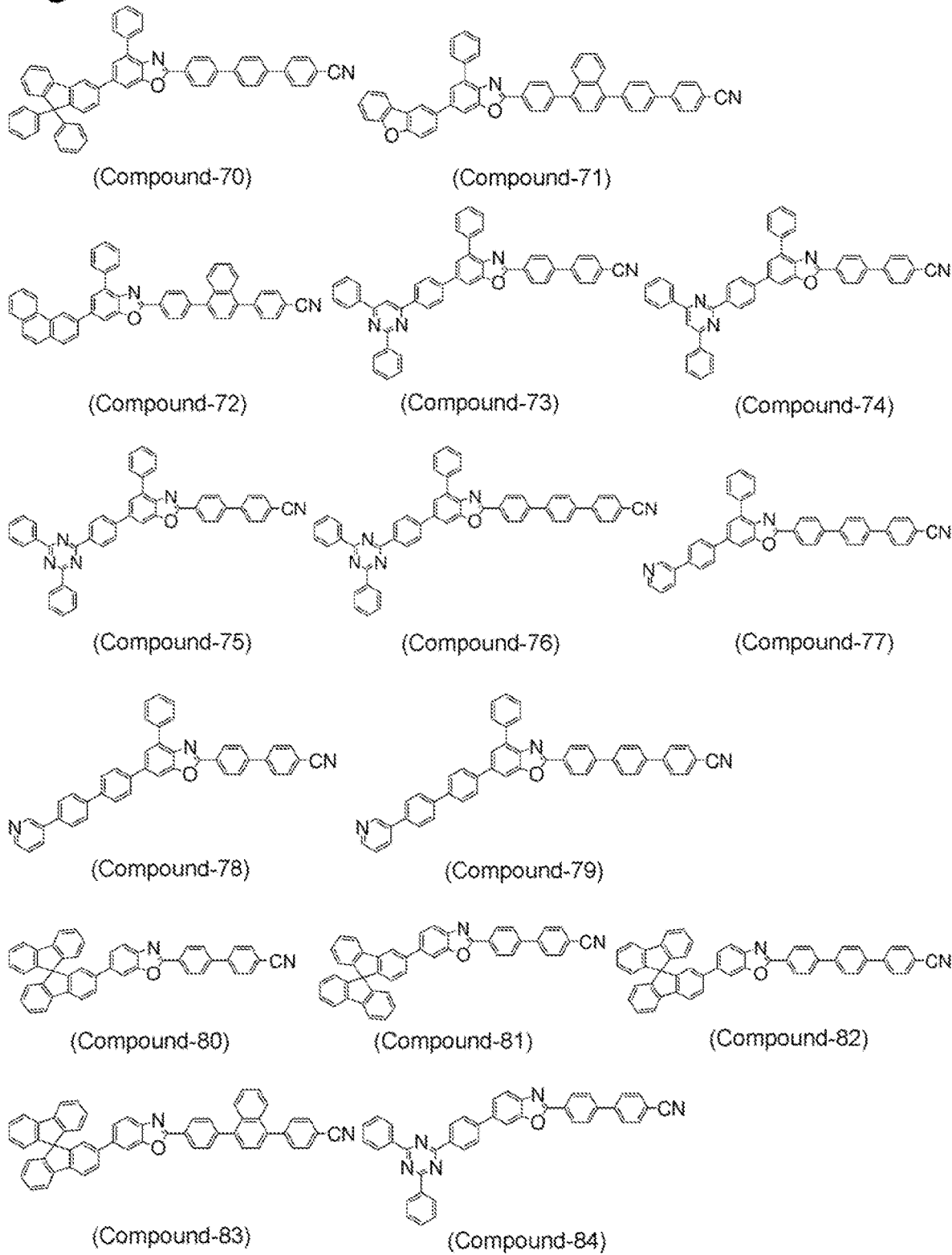
FIG. 5 shows the structures of Compounds 70 to 84 as examples of the compound having a benzazole ring structure represented by the general formula (a-1).
Figure 6:
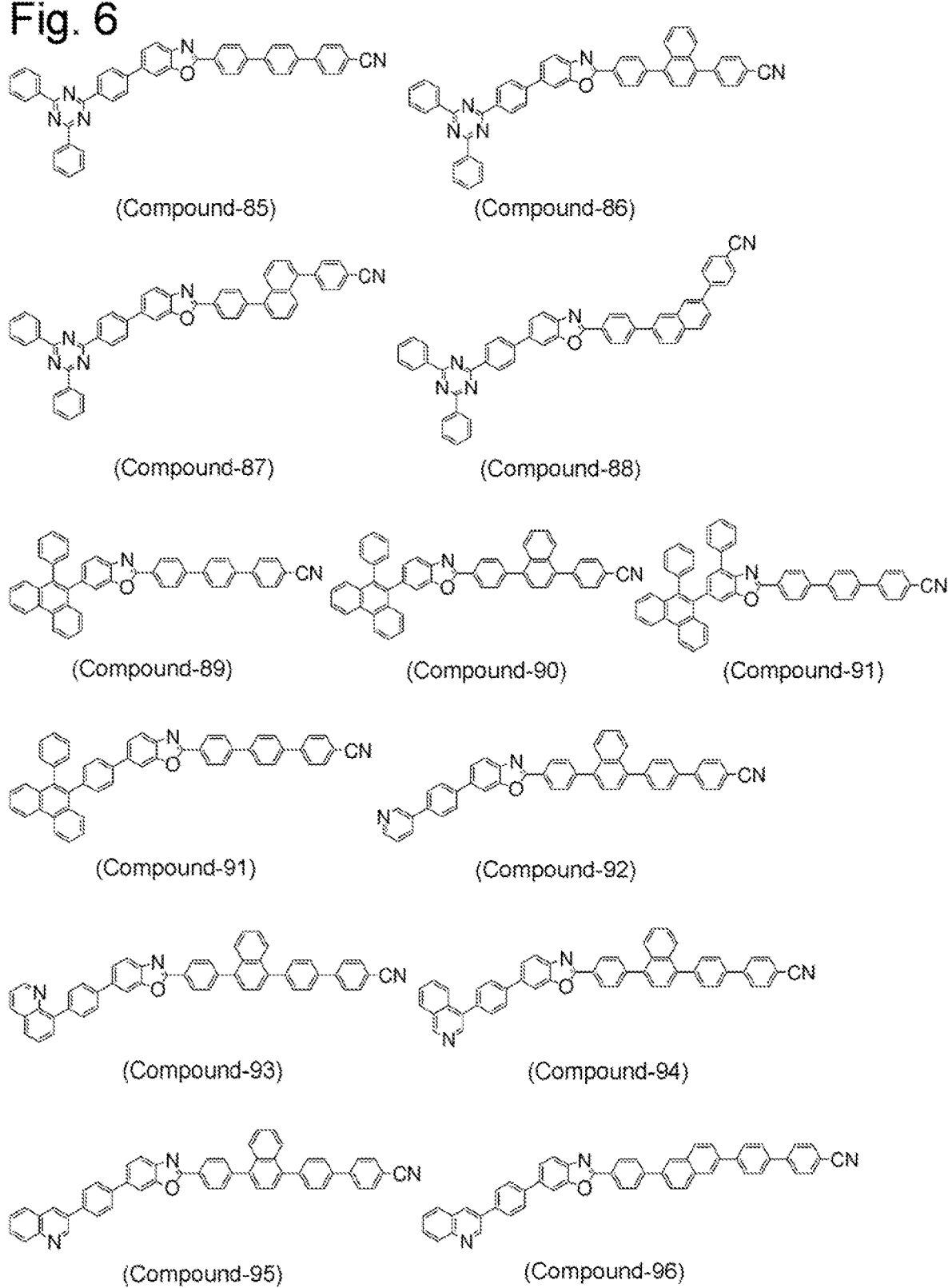
FIG. 6 shows the structures of Compounds 85 to 96 as examples of the compound having a benzazole ring structure represented by the general formula (a-1).
Figure 7:
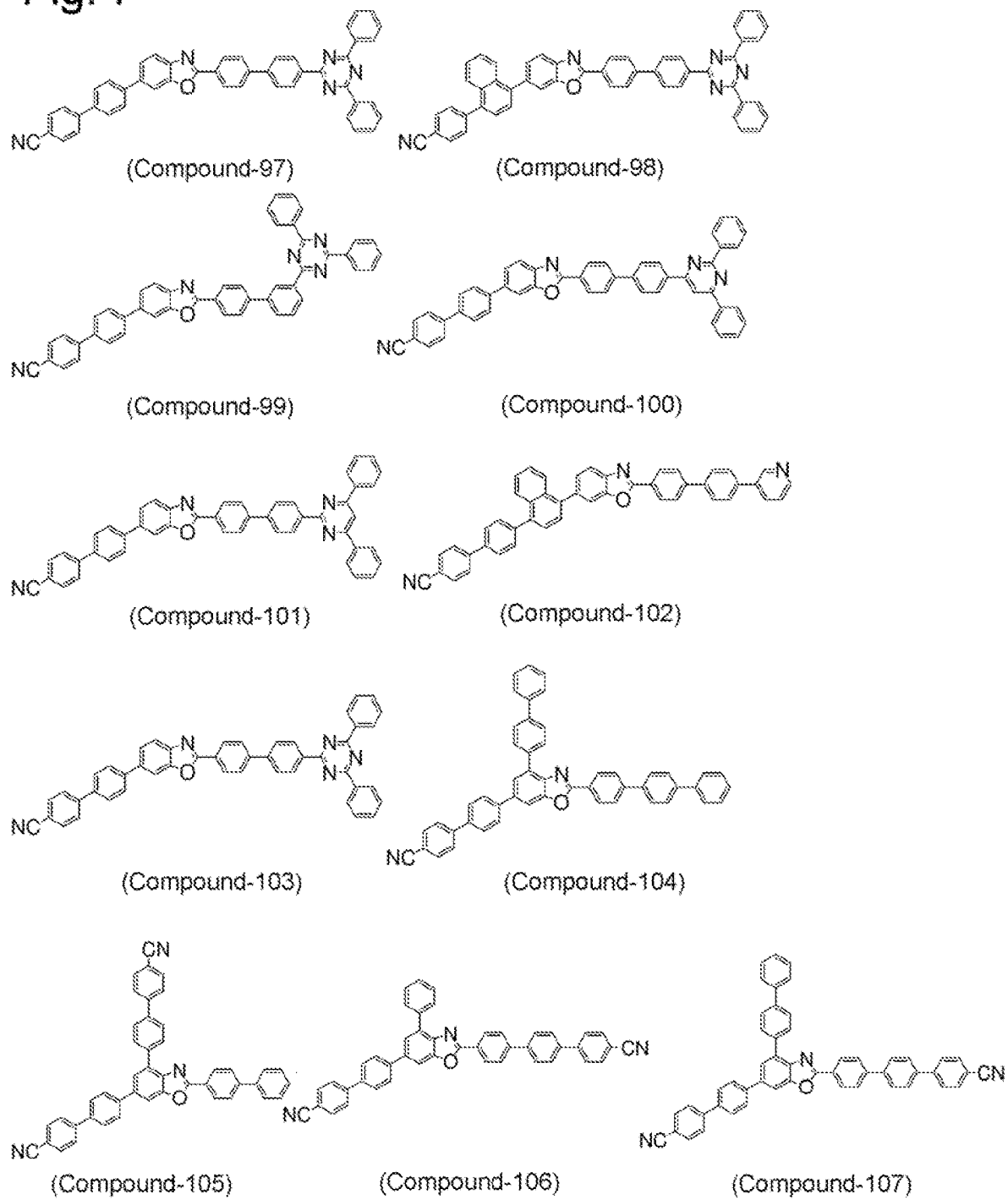
FIG. 7 shows the structures of Compounds 97 to 107 as examples of the compound having a benzazole ring structure represented by the general formula (a-1).
Figure 8:
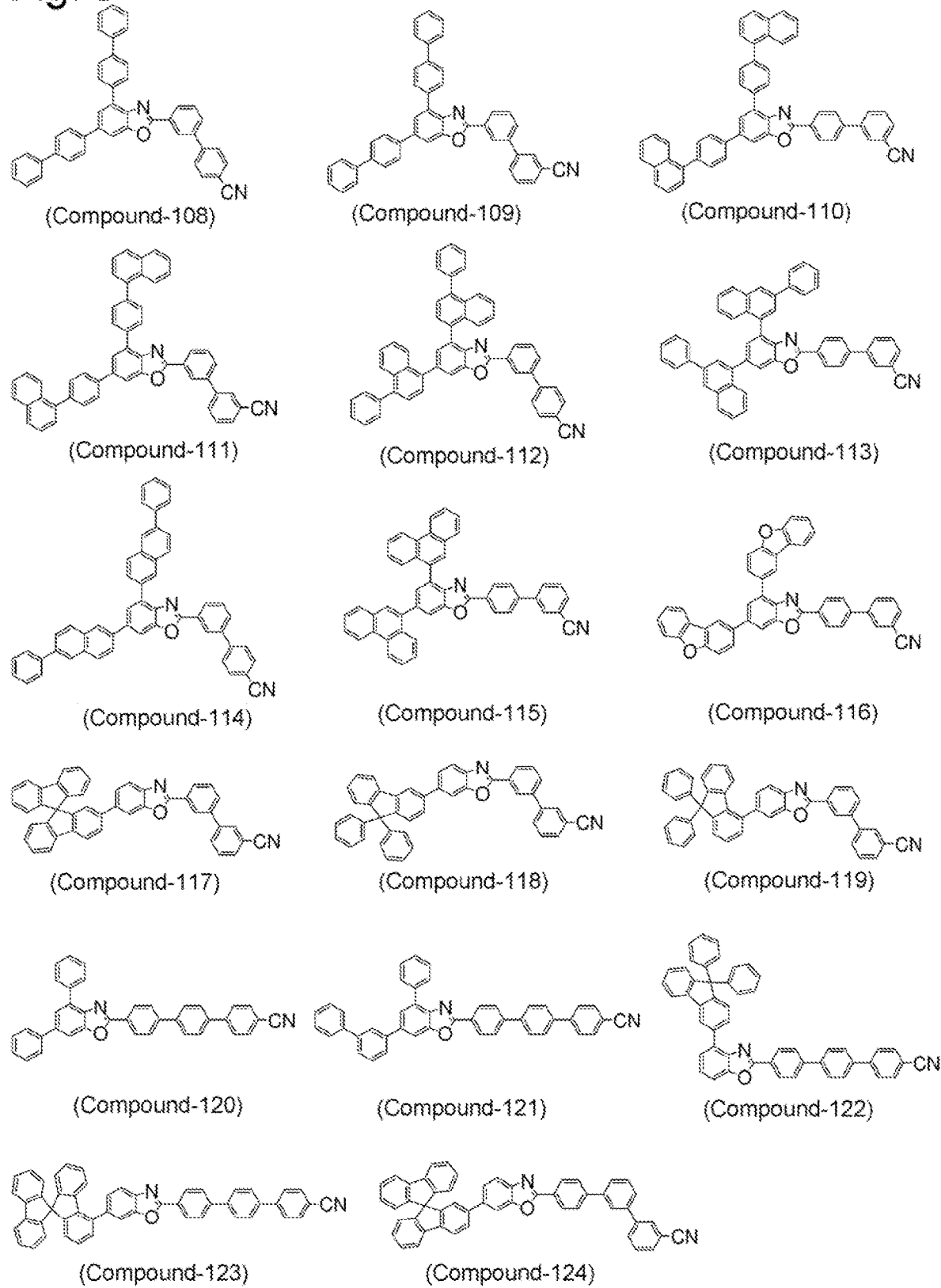
FIG. 8 shows the structures of Compounds 108 to 124 as examples of the compound having a benzazole ring structure represented by the general formula (a-1).
Figure 9:
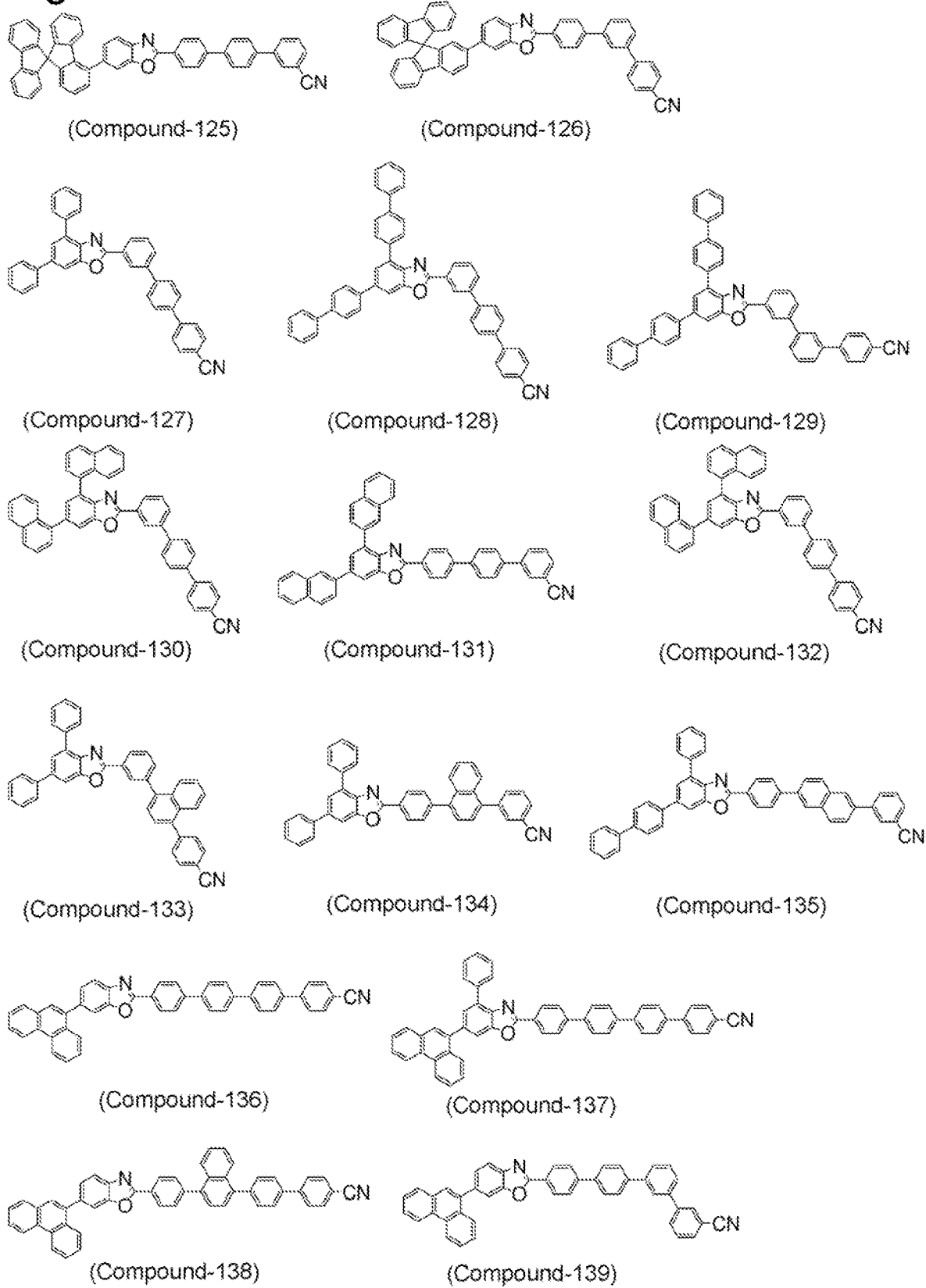
FIG. 9 shows the structures of Compounds 125 to 139 as examples of the compound having a benzazole ring structure represented by the general formula (a-1).
Figure 10:
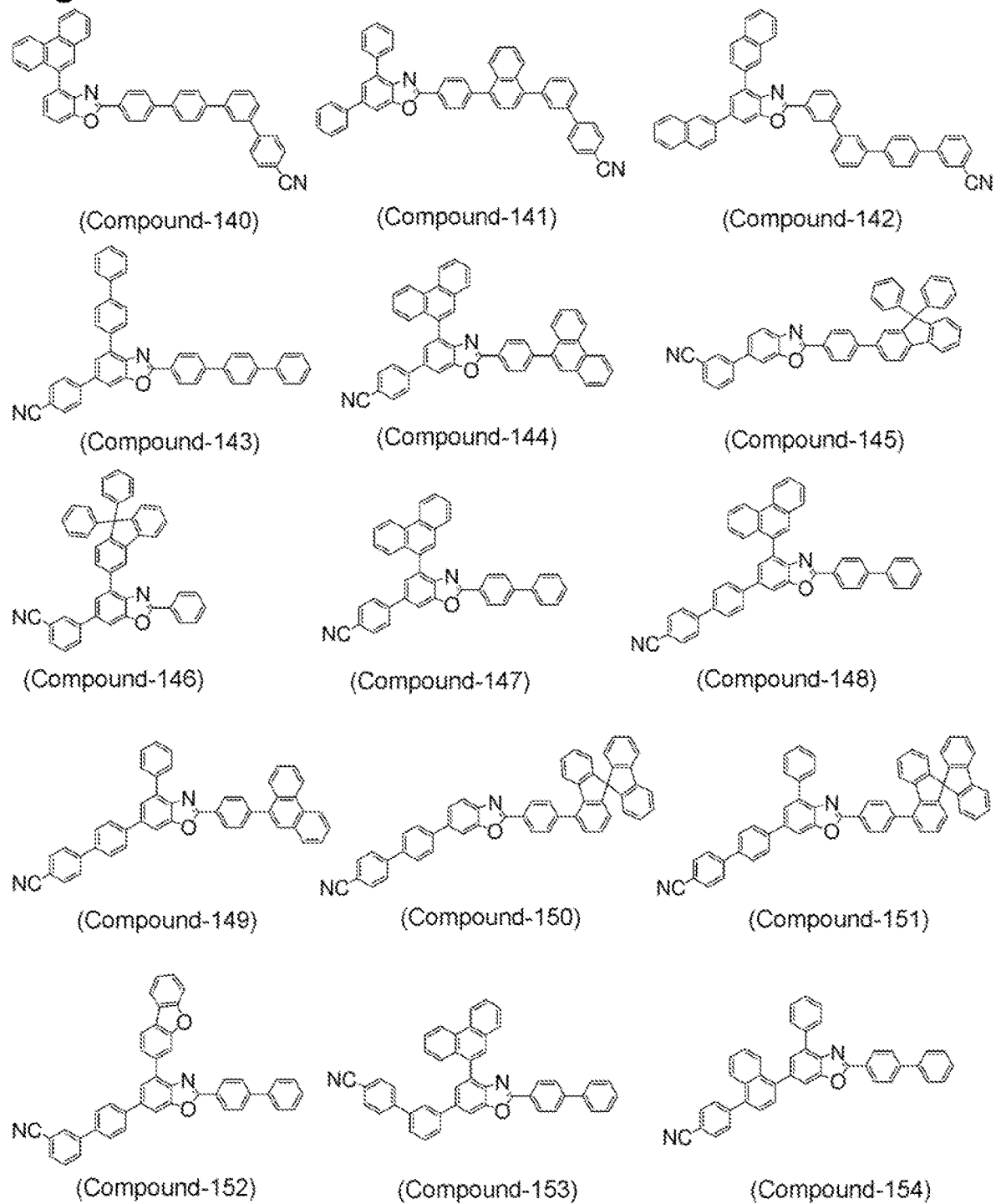
FIG. 10 shows the structures of Compounds 140 to 154 as examples of the compound having a benzazole ring structure represented by the general formula (a-1).
Figure 11:
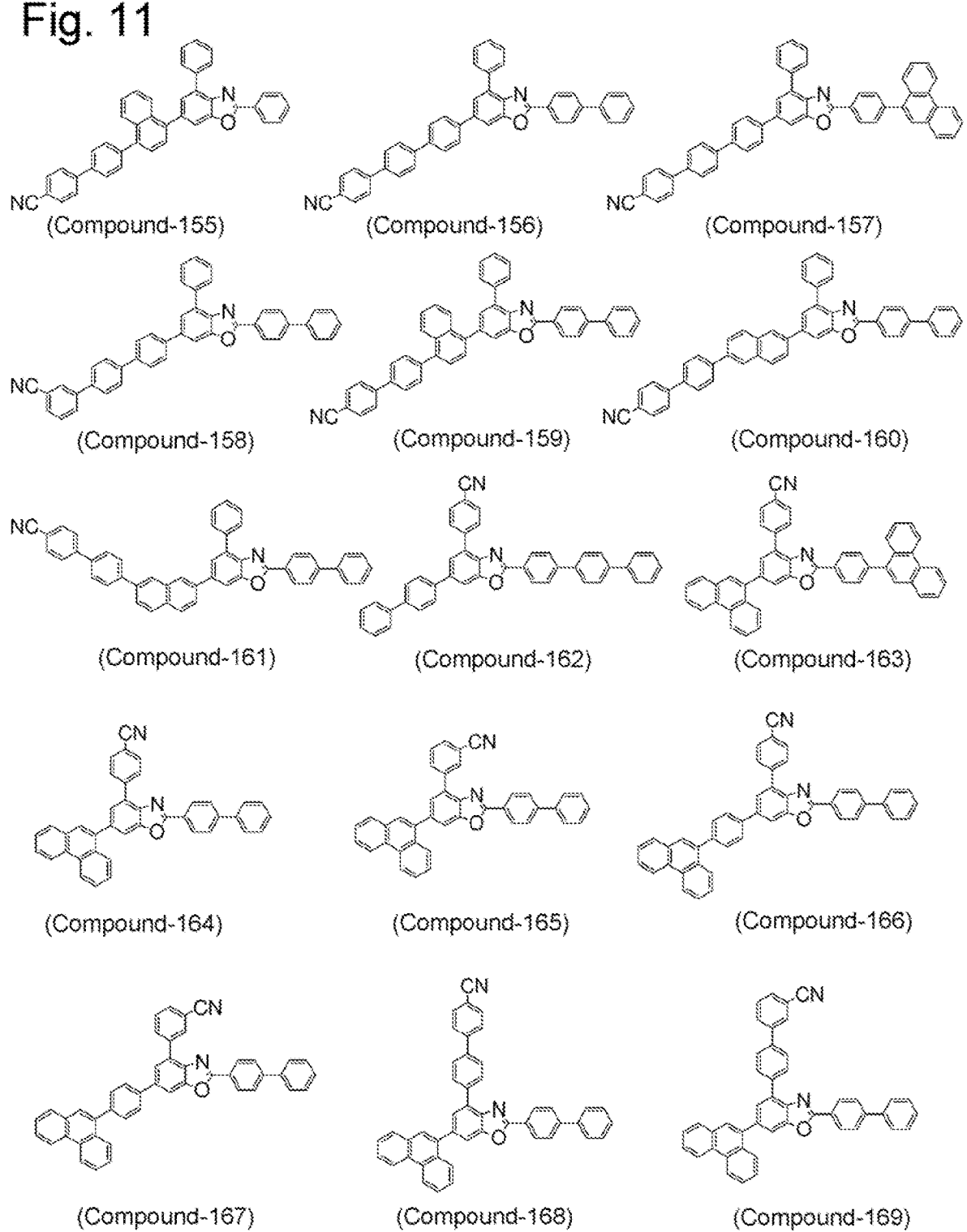
FIG. 11 shows the structures of Compounds 155 to 169 as examples of the compound having a benzazole ring structure represented by the general formula (a-1).
Figure 12:
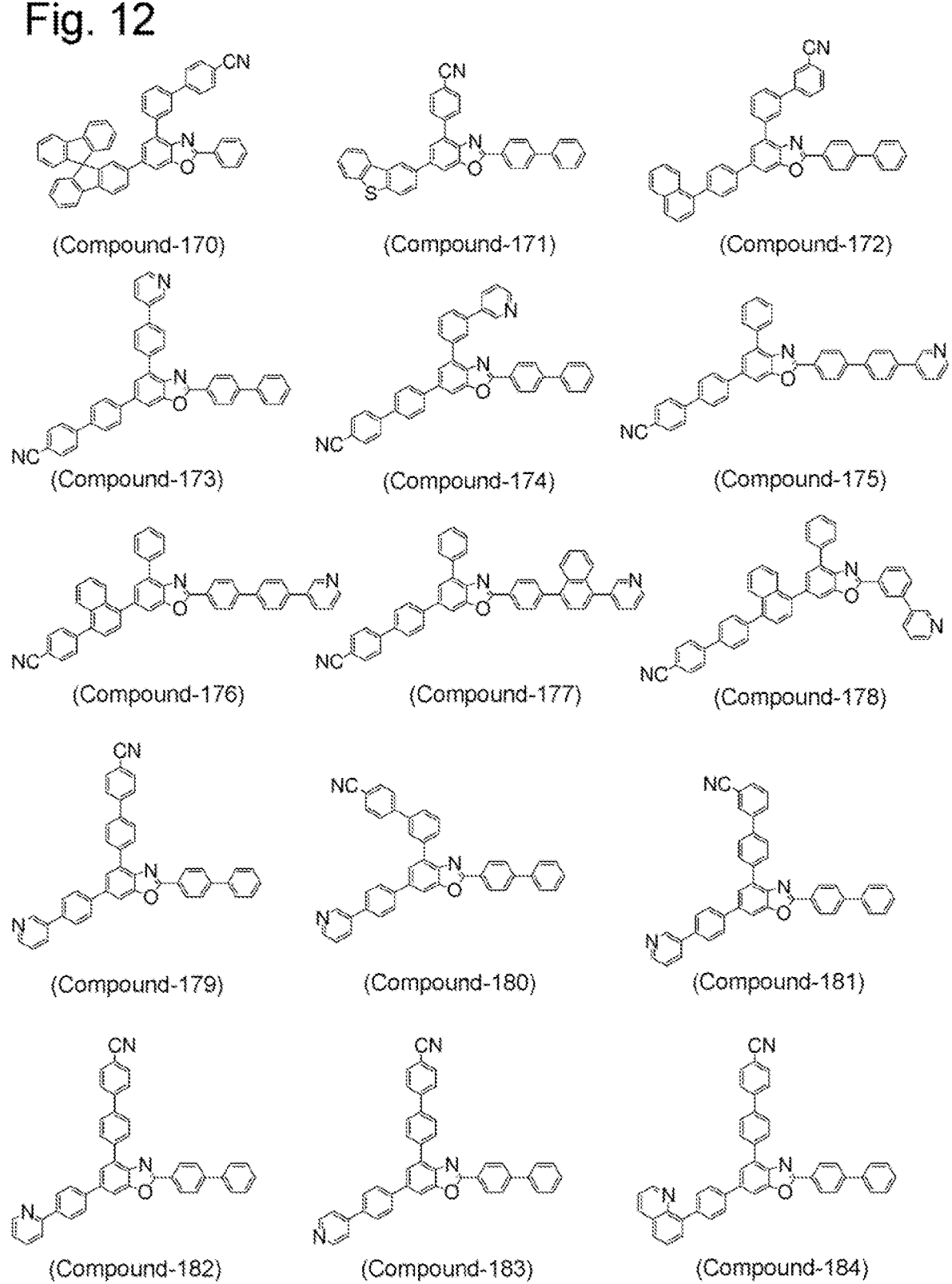
FIG. 12 shows the structures of Compounds 170 to 184 as examples of the compound having a benzazole ring structure represented by the general formula (a-1).
Figure 13:
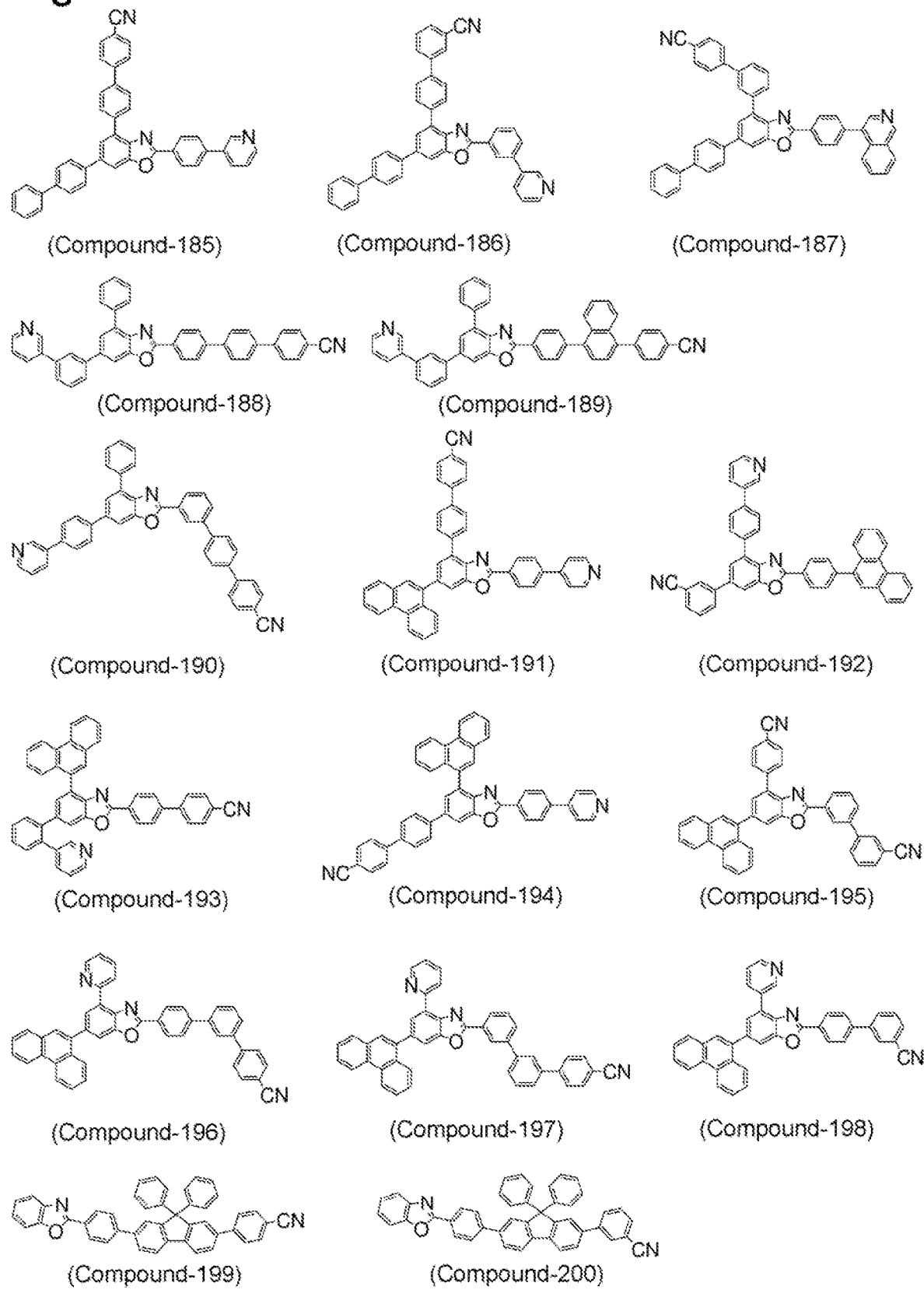
FIG. 13 shows the structures of Compounds 185 to 200 as examples of the compound having a benzazole ring structure represented by the general formula (a-1).
Figure 14:
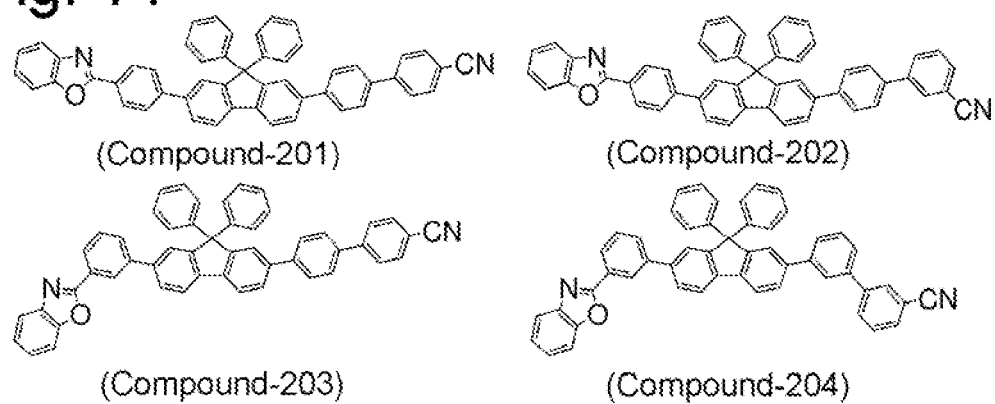
FIG. 14 shows the structures of Compounds 201 to 204 as examples of the compound having a benzazole ring structure represented by the general formula (a-1).

In the present invention, X in the general formula (a-1) above is preferably an oxygen atom in view of hole-blocking capability and electron-transporting capability. That is to say, the compound of the present invention is preferably the compound having a benzazole ring structure and represented by the general formula (a-2) above.

Furthermore, Y is preferably a carbon atom having R. In other words, the compound of the present invention is more preferably the compound having a benzazole ring structure and represented by the general formula (a-3) above.

In view of stability in the form of a thin film, R in the general formula (a-1) above is preferably a hydrogen atom, a substituted or unsubstituted aromatic hydrocarbon group, a substituted or unsubstituted aromatic heterocyclic group, a substituted or unsubstituted fused polycyclic aromatic group, or a group represented by the structural formula (b-1) above.

Specifically, the compound of the present invention is preferably the compound having a benzazole ring structure and represented by the general formula (a-4) above, and more preferably the compound having a benzazole ring structure represented by the general formula (a-5) above.

In view of hole-blocking capability and electron-transporting capability, $L_1$ and $L_2$ in the structural formula (b-1) above are preferably a group selected from a substituted or unsubstituted phenylene group, a substituted or unsubstituted biphenylene group, a substituted or unsubstituted terphenylene group, a substituted or unsubstituted naphthylene group, and a substituted or unsubstituted fluorenylene group. Furthermore, $L_2$ in the structural formula (b-1) above is preferably a substituted or unsubstituted phenylene group, or a substituted or unsubstituted biphenylene group.

Preferable examples of the group represented by the structural formula (b-1) above include groups represented by the structural formulae below:

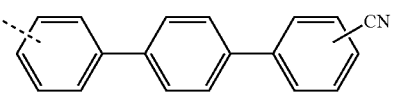

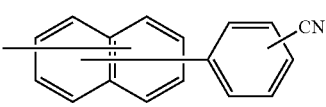

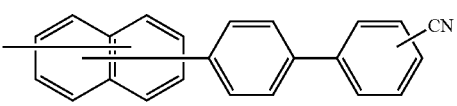

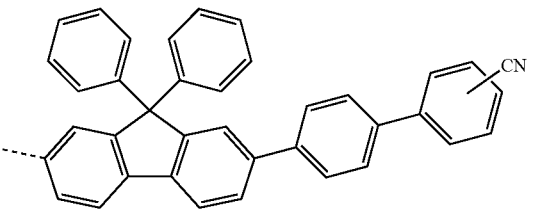

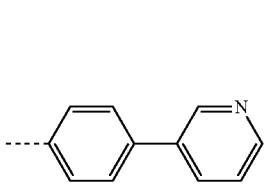

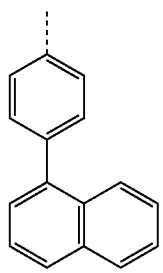

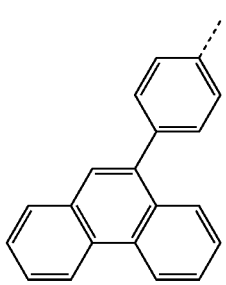

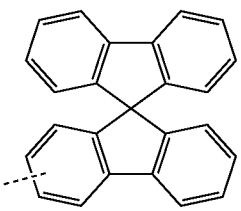

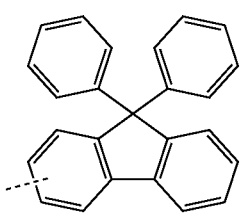

where the dashed lines each indicate a binding site.

In view of hole-blocking capability and electron-transporting capability, the substituted or unsubstituted aromatic hydrocarbon group, the substituted or unsubstituted aromatic heterocyclic group, and the substituted or unsubstituted fused polycyclic aromatic group represented by R in the general formula (a-1) are preferably a phenyl group, a naphthyl group, a phenanthrenyl group, a spirobifluorenyl group, a pyridyl group, a substituted or unsubstituted fluorenyl group, or a substituted or unsubstituted triazinyl group, or a group obtained by combining any of these groups with a phenylene group.

Preferable examples of the group represented by R in the general formula (a-1) include groups represented by the structural formulae below:

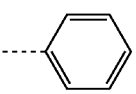
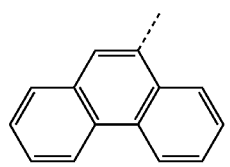
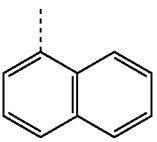
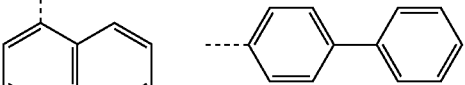

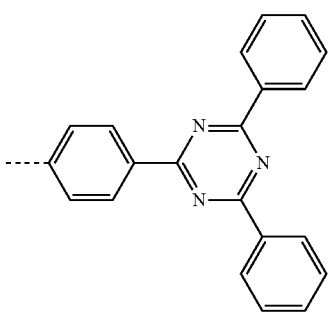

where the dashed lines each indicate a binding site.

Specific preferred examples of the compound having a benzazole ring structure represented by the general formula (a-1) above, which is favorably used for the organic EL element of the present invention, are shown in FIGS. 1 to 14, but the present invention is not limited to these compounds.

The compound having a benzazole ring structure of the present invention is a novel compound. These compounds can be synthesized, for example, according to known methods as in the following manner (see Patent Literatures 5 and 6, and Non-Patent Literatures 6 and 7, for example).

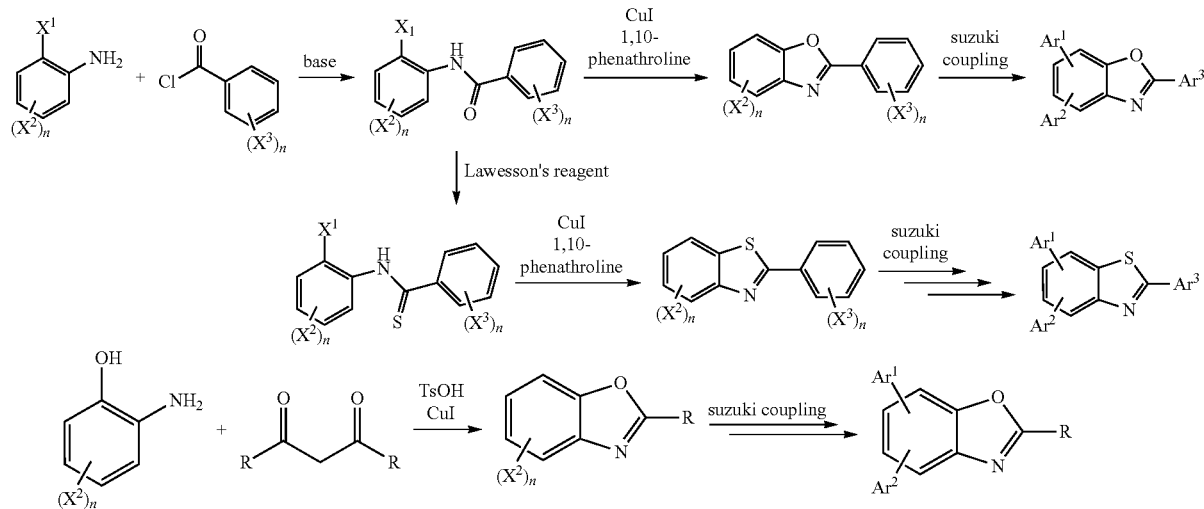

The compounds having a benzazole ring structure represented by the general formulae (a-1) to (a-7) can be purified using a purification method such as column chromatography, adsorption using silica gel, activated carbon, activated clay, or others, recrystallization or crystallization from a solvent; or sublimation. The compound can be identified by NMR analysis. The physical properties can be measured in terms of melting point, glass transition point (Tg), work function, and the like. The melting point is a measure of vapor deposition properties, the glass transition point (Tg) is a measure of stability in the form of a thin film, and the work function is a measure of hole-transporting capability and hole-blocking capability.

The melting point and the glass transition point (Tg) can be measured on the compound in the form of a powder using a high-sensitivity differential scanning calorimeter (DSC3100SA manufactured by Bruker AXS K.K.), for example.

The work function can be measured on the compound in the form of a thin film with a thickness of 100 nm formed on an ITO substrate using an ionization potential measuring device (PYS-202 manufactured by Sumitomo Heavy Industries, Ltd.), for example.

The organic EL element of the present invention may have a structure in which an anode, a hole-injecting layer, a hole-transporting layer, a light-emitting layer, an electron-transporting layer, an electron-injecting layer, and a cathode sequentially are sequentially provided on a substrate; and the structure may further include an electron-blocking layer between the hole-transporting layer and the light-emitting layer; and also may further include a hole-blocking layer between the light-emitting layer and the electron-transporting layer. In these multilayer structures, a single organic layer may perform the functions of some layers. For example, a single organic layer may serve as both the hole-injecting layer and the hole-transporting layer, and a single organic layer may serve as both the electron-injecting layer and the electron-transporting layer. Moreover, it is possible to stack two or more organic layers having the same function. Specifically, two hole-transporting layers may be stacked; two light-emitting layers may be stacked; and two electron-transporting layers may be stacked.

An electrode material having a high work function, such as ITO or gold, is used for the anode of the organic EL element of the present invention.

Examples of a material used for the hole-injecting layer of the organic EL element of the present invention include porphyrin compounds typified by copper phthalocyanine, starburst triphenylamine derivatives; arylamine compounds having a structure containing two or more triphenylamine structures or carbazolyl structures in the molecule, the triphenylamine or carbazolyl structures being linked to each other via a single bond or a divalent group having no heteroatom; heterocyclic compounds of acceptor type, such as hexacyanoazatriphenylene; and polymer materials of coating type.

Examples of a material used for the hole-transporting layer of the organic EL element of the present invention include benzidine derivatives such as N,N'-diphenyl-N,N'-di(m-tolyl)-benzidine (hereinafter abbreviated as "TPD"), N,N'-diphenyl-N,N'-di(α-naphthyl)-benzidine (hereinafter abbreviated as "NPD"), and N,N,N',N'-tetrabiphenylyl benzidine, 1,1-bis[(di-4-tolylamino)phenyl] cyclohexane (hereinafter abbreviated as "TAPC"); and arylamine compounds having a structure containing two or more triphenylamine structures or carbazolyl structures in the molecule, the triphenylamine or carbazolyl structures being linked to each other via a single bond or a divalent group containing no heteroatom.

It is also possible to use, as a material for the hole-injecting layer or the hole-transporting layer, polymer materials of coating type, such as poly(3,4-ethylenedioxythiophene) (hereinafter abbreviated as "PEDOT")/poly(styrene sulfonate) (hereinafter abbreviated as "PSS").

Furthermore, other examples of the material used for the hole-injecting layer or the hole-transporting layer include those obtained by p-doping a material normally used for these layers with trisbromophenylamine hexachloroantimony or a radialene derivative (see Patent Literature 7, for example); and a polymer compound having the structure of a benzidine derivative, such as TPD, as a partial structure thereof.

Examples of a material used for the electron-blocking layer of the organic EL element of the present invention include compounds having an electron blocking effect, such as carbazole derivatives such as 4,4',4"-tri(N-carbazolyl) triphenylamine (hereinafter abbreviated as "TCTA"), 9,9-bis[4-(carbazole-9-yl)phenyl]fluorene, 1,3-bis(carbazole-9-yl)benzene (hereinafter abbreviate as "mCP"), and 2,2-bis (4-carbazole-9-ylphenyl)adamantane (hereinafter abbreviate as "Ad-Cz"), and compounds having a triphenylsilyl group and a triarylamine structure and typified by 9-[4-(carbazole-9-yl)phenyl]-9-[4-(triphenylsilyl)phenyl]-9H-fluorene.

Examples of a material used for the light-emitting layer of the organic EL element of the present invention include the compound having a benzazole ring structure of the present invention, and also metal complexes of quinolinol derivatives such as Alq$_3$, various types of metal complexes, an anthracene derivative, a bisstyrylbenzene derivative, a pyrene derivative, an oxazole derivative, and a poly(p-phenylene vinylene) derivative. The light-emitting layer may include a host material and a dopant material. As the host material, an anthracene derivative is preferably used. Other examples of the host material include the above-listed light emitting materials including the compound having a benzazole ring structure of the present invention, and also a heterocyclic compound having an indole ring as a partial structure of a fused ring; a heterocyclic compound having a carbazole ring as a partial structure of a fused ring; a carbazole derivative; a thiazole derivative; a benzimidazole derivative; and a polydialkylfluorene derivative. Examples of the dopant material include quinacridone, coumarin, rubrene, perylene, and derivatives thereof, a benzopyran derivative; a rhodamine derivative; and an aminostyryl derivative.

A phosphorescent emitter can also be used as the material for the light-emitting layer. The phosphorescent emitter may be a metal complex of iridium, platinum, or the like, and examples thereof include a green phosphorescent emitter such as Ir(ppy)$_3$, a blue phosphorescent emitter such as FIrpic or FIr6, and a red phosphorescent emitter such as Btp$_2$Ir (acac). As a host material in this case, a host material having hole-injecting/transporting capability may be used, including carbazole derivatives such as 4,4'-di(N-carbazolyl)biphenyl (hereinafter abbreviated as "CBP"), TCTA, and mCP, and also the compound having a benzazole ring structure of the present invention, and also, a host material having electron-transporting capability may be used, including p-bis(triphenylsilyl)benzene (hereinafter abbreviated as "UGH2") and 2,2',2"-(1,3,5-phenylene)-tris(1-phenyl-1H-benzimidazole) (hereinafter abbreviated as "TPBI"). Use of these materials enables production of a high-performance organic EL element.

In order to avoid concentration quenching, doping of the host material with a phosphorescent material is preferably performed by co-deposition in an amount within a range of 1 to 30 wt % based on the entire light-emitting layer.

As the light emitting material, a material that emits delayed fluorescence can also be used, including CDCB derivatives such as PIC-TRZ, CC2TA, PXZ-TRZ, and 4CzIPN (see Non-Patent Literature 3, for example).

Examples of a material used for the hole-blocking layer of the organic EL element of the present invention include the compound having a benzazole ring structure of the present invention, and also compounds exhibiting a hole-blocking effect, including a phenanthroline derivative, such as bathocuproine (hereinafter abbreviated as "BCP"); a metal complex of a quinolinol derivative, such as BAlq; various types of rare-earth complexes; an oxazole derivative; a triazole derivative; and a triazine derivative. These materials may also serve as the material for the electron-transporting layer.

Examples of a material used for the electron-transporting layer of the organic EL element of the present invention include the compound having a benzazole ring structure of the present invention, and also metal complexes of quinolinol derivatives, such as Alq$_3$ and BAlq; various types of metal complexes; a triazole derivative; a triazine derivative; an oxadiazole derivative; a pyridine derivative; a benzimidazole derivative; a thiadiazole derivative; an anthracene derivative; a carbodiimide derivative; a quinoxaline derivative; a pyridoindole derivative; a phenanthroline derivative; a silole derivative.

Examples of a material used for the electron-injecting layer of the organic EL element of the present invention include the compound having a benzazole ring structure of the present invention, and also alkali metal salts such as lithium fluoride and cesium fluoride; alkaline earth metal salts such as magnesium fluoride; metal complexes of quinolinol derivatives such as lithium quinolinol; metal oxides such as aluminum oxide; and metals such as ytterbium (Yb), samarium (Sm), calcium (Ca), strontium (Sr), and cesium (Cs). The electron-injecting layer can however be omitted when the electron-transporting layer and a cathode are suitably selected.

Furthermore, a material obtained by n-doping a material normally used for an electron-injecting layer or an electron-transporting layer with a metal such as cesium can be used as the material for the electron-injecting layer or the electron-transporting layer.

Examples of an electrode material used for the cathode of the organic EL element of the present invention include an electrode material having a low work function, such as aluminum; and an alloy having an even lower work function, such as a magnesium-silver alloy, a magnesium-indium alloy, and an aluminum-magnesium alloy.

The above-described materials for the layers constituting the organic EL element can be formed into a thin film using a known method such as vapor deposition, spin coating, or inkjet printing.

These materials may be used singly for film formation, or two or more of these materials may be mixed and used for film formation. In each case, a single layer may be formed. Any layer may have a layered structure composed of different layers each formed of a single kind of material, a layered structure composed of different layers each formed of a mixture of materials, or a layered structure composed of a layer formed of a single kind of material and a layer formed of a mixture of two or more of materials.

EXAMPLES

Hereinafter, embodiments of the present invention will be described in greater detail by way of examples. However, the present invention is not limited to Examples below unless the gist thereof is exceeded.

Example 1

Synthesis of 4,6-bis(4-naphthalene-1-yl-phenyl)-2-(4'-cyano-biphenyl-4-yl)-benzoxazole (Compound-2)

First, 8.8 g of 2-(4-chlorophenyl)-4,6-bis(4-naphthalene-1-yl-phenyl)-benzoxazole, 3.2 g of 4-cyanophenylboronic acid, 0.3 g of tris(dibenzylideneacetone)dipalladium(0), 0.4 g of tricyclohexylphosphine, and 5.4 g of tripotassium phosphate were place in a reaction vessel, and stirred in a mixed solvent of 1,4-dioxane/H$_2$O under reflux overnight. After allowing to cool, methanol was added to the system for dispersing and washing, and the resulting system was filtered to obtain a crude product. The obtained crude product was purified through crystallization from a mixed solvent of monochlorobenzene/acetone to thereby obtain 7.2 g (yield:

83%) of a pale yellow powder of 4,6-bis(4-naphthalene-1-yl-phenyl)-2-(4'-cyano-biphenyl-4-yl)-benzoxazole (Compound-2).

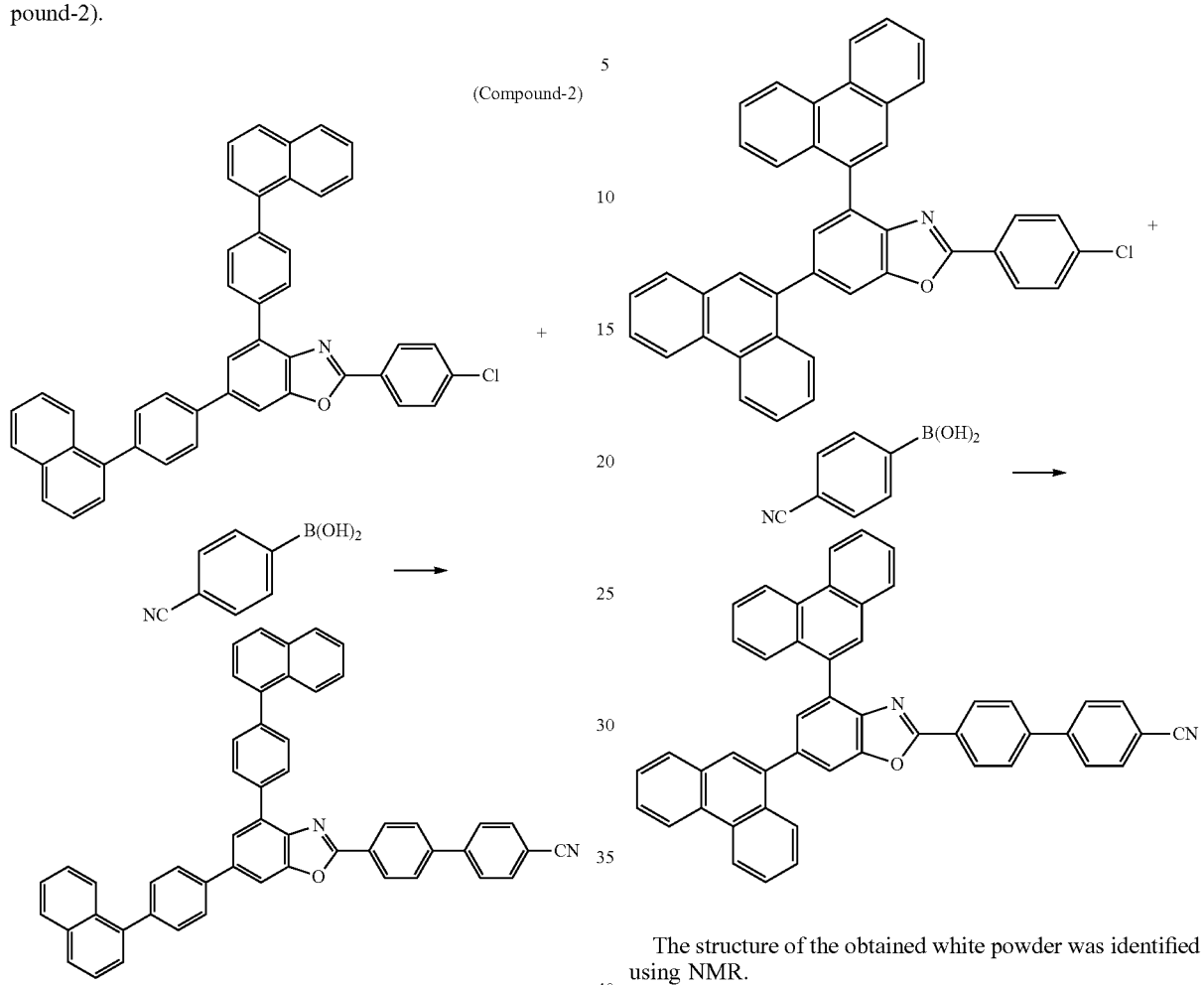

The structure of the obtained pale yellow powder was identified using NMR.

In $^1$H-NMR (CDCl$_3$), the following signals of 32 hydrogens were detected.

δ (ppm)=8.52 (2H), 8.33 (2H), 8.13 (1H), 8.05 (1H), 8.04 (1H), 8.01-7.88 (7H), 7.85-7.78 (6H), 7.75 (2H), 7.70 (2H), 7.65-7.47 (8H)

Example 2

Synthesis of 4,6-bis(phenanthrene-9-yl)-2-(4'-cyano-biphenyl-4-yl)-benzoxazole (Compound-10)

First, 10.0 g of 2-(4-chloro-phenyl)-4,6-bis(phenanthrene-9-yl)-benzoxazole, 3.0 g of 4-cyanophenylboronic acid, 0.5 g of tris(dibenzylideneacetone)dipalladium (0), 0.5 g of tricyclohexylphosphine, and 7.3 g of tripotassium phosphate were placed in a reaction vessel, and stirred in a mixed solvent of 1,4-dioxane/H$_2$O under reflux overnight. After allowing to cool, methanol was added to the system for dispersing and washing, and the resulting system was filtered to obtain a crude product. The obtained crude product was purified through recrystallization from monochlorobenzene as solvent to thereby obtain 4.0 g (yield: 36%) of a white powder of 4,6-bis(phenanthrene-9-yl)-2-(4'-cyano-biphenyl-4-yl)-benzoxazole (Compound-10).

The structure of the obtained white powder was identified using NMR.

In $^1$H-NMR (CDCl$_3$), the following signals of 28 hydrogens were detected.

δ (ppm)=8.85 (2H), 8.79 (2H), 8.35 (2H), 8.17 (1H), 8.05 (1H), 8.04 (1H), 7.98 (2H), 7.91 (2H), 7.80-7.58 (12H), 7.65 (2H), 7.59 (1H)

Example 3

Synthesis of 2-(4"-cyano-[1,1';4',1"]terphenyl-4-yl)-4,6-di(naphthalene-1-yl)-benzoxazole (Compound-22)

First, 8.0 g of 4,6-bis(naphthalene-1-yl)-2-(4-chloro-phenyl)-benzoxazole, 6.1 g of 4'-(4,4,5,5-tetramethyl-[1,3,2]dioxaborolane-2-yl)biphenyl-4-carbonitrile, 0.8 g of tris(dibenzylideneacetone)dipalladium(0), 0.9 g of tricyclohexylphosphine, and 10.6 g of tripotassium phosphate were placed in a reaction vessel, and stirred in a mixed solvent of 1,4-dioxane/H$_2$O under reflux overnight. After allowing to cool, water was added to the system for dispersing and washing, and the resulting system was filtered to obtain a crude product. The obtained crude product was purified through recrystallization from monochlorobenzene as solvent to thereby obtain 9.3 g (yield: 90%) of a white powder of 4,6-bis(naphthalene-1-yl)-2-(4"-cyano-[1,1';4',1"]terphenyl-4-yl)-benzoxazole (Compound-22).

(Compound-22)

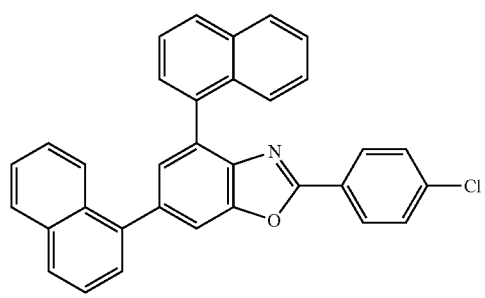

The structure of the obtained white powder was identified using NMR.

In ¹H-NMR (CDCl₃), the following signals of 28 hydrogens were detected.

δ (ppm)=8.36 (2H), 8.14 (1H), 8.03 (1H), 7.98 (3H), 7.94 (1H), 7.85 (1H), 7.84-7.69 (11H), 7.68 (2H), 7.61 (2H), 7.54 (3H), 7.48 (1H)

Example 4

Synthesis of 4,6-bis(biphenyl-4-yl)-2-(4"-cyano-[1,1';4',1" ]terphenyl-4-yl)-benzoxazole (Compound-23)

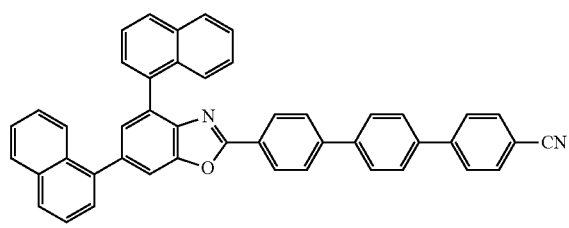

First, 11.4 g of 4,6-bis(biphenyl-4-yl)-2-(4-chloro-phenyl)-benzoxazole, 7.8 g of 4'-(4,4,5,5-tetramethyl-[1,3,2]dioxaborolane-2-yl)biphenyl-4-carbonitrile, 1.0 g of tris(dibenzylideneacetone)dipalladium(0), 1.2 g of tricyclohexylphosphine, and 13.6 g of tripotassium phosphate were placed in a reaction vessel, and stirred in a mixed solvent of 1,4-dioxane/H₂O under reflux overnight. After allowing to cool, methanol and water were added to the system for dispersing and washing, and the resulting system was filtered to obtain a crude product. The obtained crude product was purified through recrystallization from 1,2-dichlorobenzene as solvent to thereby obtain 13.7 g (yield: 95%) of a yellow powder of 4,6-bis(biphenyl-4-yl)-2-(4"-cyano-[1,1';4',1" ]terphenyl-4-yl)-benzoxazole (Compound-23).

(Compound-23)

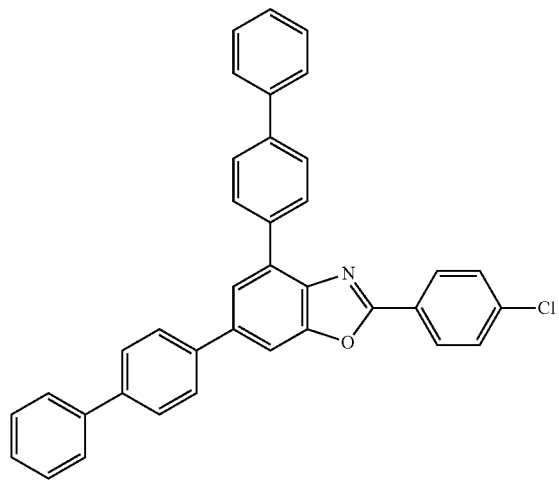

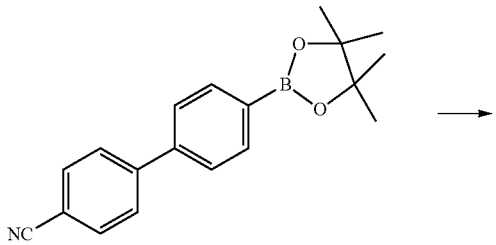

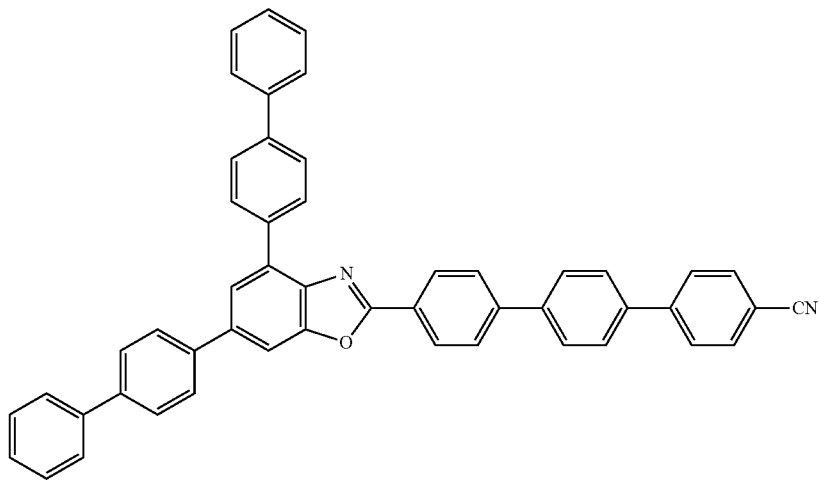

The structure of the obtained yellow powder was identified using NMR.

In $^1$H-NMR (CDCl$_3$), the following signals of 32 hydrogens were detected.

δ (ppm)=8.45 (2H), 8.26 (2H), 7.92 (1H), 7.90-7.67 (21H), 7.52 (4H), 7.42 (2H)

Example 5

Synthesis of 4,6-bis(4-naphthalene-1-yl-phenyl)-2-(4″-cyano-[1,1′,4′,1″]terphenyl-4-yl)-benzoxazole (Compound-24)

First, 8.0 g of 2-(4-chlorophenyl)-4,6-bis(4-naphthalene-1-yl-phenyl)-benzoxazole, 4.6 g of 4′-(4,4,5,5-tetramethyl-[1,3,2]dioxaborolane-2-yl)biphenyl-4-carbonitrile, 0.3 g of tris(dibenzylideneacetone)dipalladium(0), 0.4 g of tricyclohexylphosphine, and 5.4 g of tripotassium phosphate were placed in a reaction vessel, and stirred in a mixed solvent of 1,4-dioxane/H$_2$O under reflux overnight. After allowing to cool, methanol was added to the system for dispersing and washing, and the resulting system was filtered to obtain a crude product. The obtained crude product was purified through recrystallization from monochlorobenzene to thereby obtain 3.2 g (yield: 32%) of a pale yellow powder of 4,6-bis(4-naphthalene-1-yl-phenyl)-2-(4″-cyano-[1,1′,4′,1″]terphenyl-4-yl)-benzoxazole (Compound-24).

(Compound-24)

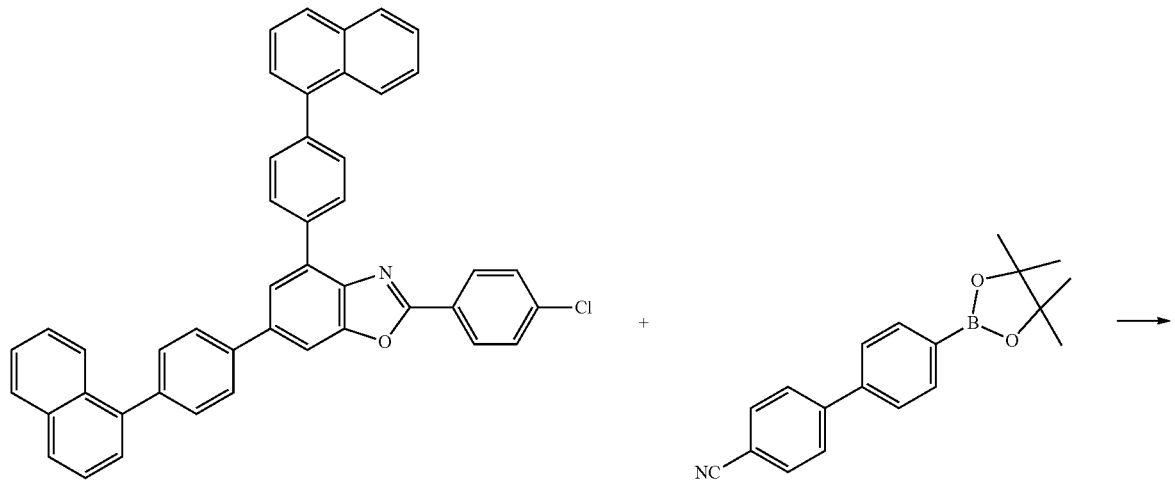

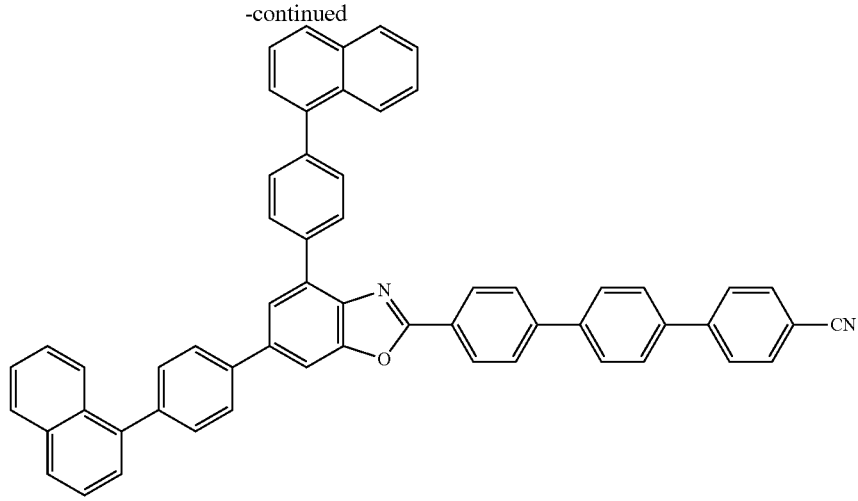

The structure of the obtained pale yellow powder was identified using NMR.

In $^1$H-NMR (CDCl$_3$), the following signals of 36 hydrogens were detected.

δ (ppm)=8.50 (2H), 8.34 (2H), 8.13 (1H), 8.06 (2H), 8.02-7.91 (7H), 7.89 (2H), 7.84 (4H), 7.81-7.72 (6H), 7.70 (2H), 7.65-7.47 (8H)

Example 6

Synthesis of 2-[4-{4-(4'-cyano-biphenyl-4-yl)-naphthalene-1-yl}-phenyl]-4,6-diphenyl-benzoxazole (Compound-27)

First, 6.8 g of 2-(4-chloro-phenyl)-4, 6-diphenyl-benzoxazole, 8.1 g of 4'-{4-(4,4,5,5-tetramethyl-[1,3,2]dioxaborolane-2-yl)-naphthalene-1-yl}-biphenyl-4-carbonitrile, 0.5 g of tris(dibenzylideneacetone)dipalladium(0), 0.5 g of tricyclohexylphosphine, and 7.6 g of tripotassium phosphate were placed in a reaction vessel, and stirred in a mixed solvent of 1,4-dioxane/H$_2$O under reflux overnight. After allowing to cool, dichloromethane and water were added to the system, followed by extraction and separation to obtain an organic layer, and the organic layer was concentrated. The obtained concentrate was purified through column chromatography (carrier: silica gel, eluent: dichloromethane/n-heptane) to thereby obtain 7.3 g (yield: 63%) of a pale yellow powder of 2-[4-{4-(4'-cyano-biphenyl-4-yl)-naphthalene-1-yl}-phenyl]-4,6-diphenyl-benzoxazole (Compound-27).

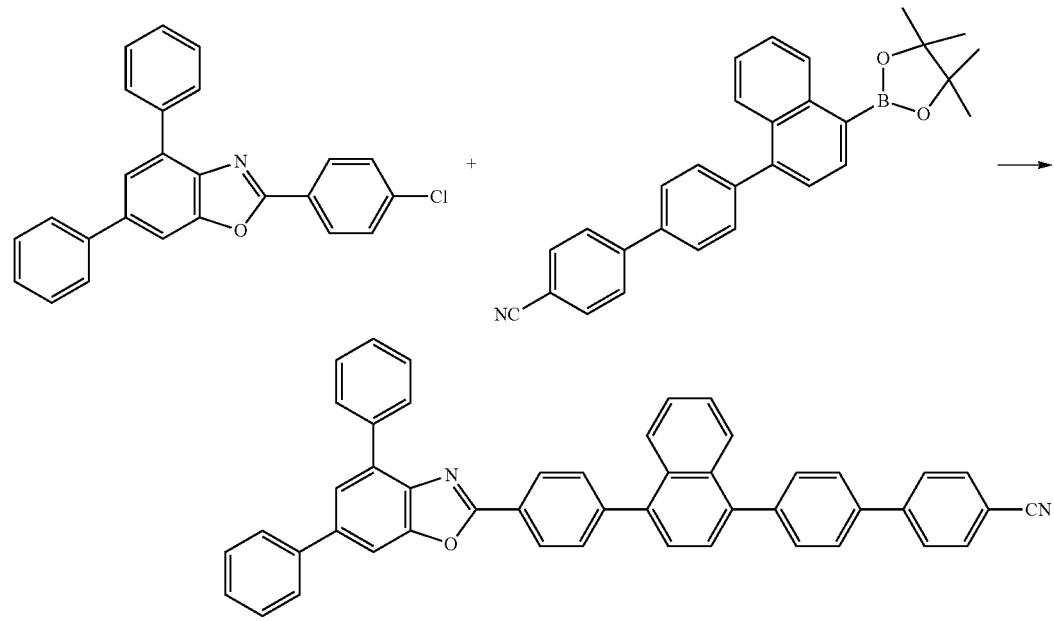

(Compound-27)

The structure of the obtained pale yellow powder was identified using NMR.

In $^1$H-NMR (CDCl$_3$), the following signals of 30 hydrogens were detected.

δ (ppm)=8.50 (2H), 8.17 (2H), 8.06 (2H), 7.88-7.66 (14H), 7.64-7.41 (10H)

Example 7

Synthesis of 2-(4'-cyano-biphenyl-4-yl)-6-{4-(4,6-diphenyl-[1,3,5]triazine-2-yl)-phenyl}-4-phenyl-benzoxazole (Compound-75)

First, 10.0 g of 2-(4-chlorophenyl)-6-{4-(4,6-diphenyl-[1,3,5]triazine-2-yl)-phenyl}-4-phenyl-benzoxazole, 2.6 g of 4-cyanophenylboronic acid, 0.8 g of tris(dibenzylideneacetone)dipalladium(0), 0.9 g of tricyclohexylphosphine, and 10.4 g of tripotassium phosphate were placed in a reaction vessel, and stirred in a mixed solvent of 1,4-dioxane/H$_2$O under reflux overnight. After allowing to cool, H$_2$O was added for dispersing and washing, and the resulting system was filtered to obtain a crude product. The obtained crude product was purified through column chromatography (carrier: silica gel, eluent: dichloromethane/ethyl acetate) to thereby obtain 7.0 g (yield: 63%) of a pale yellow powder of 2-(4'-cyano-biphenyl-4-yl)-6-{4-(4,6-diphenyl-[1,3,5]triazine-2-yl)-phenyl}-4-phenyl-benzoxazole (Compound-75).

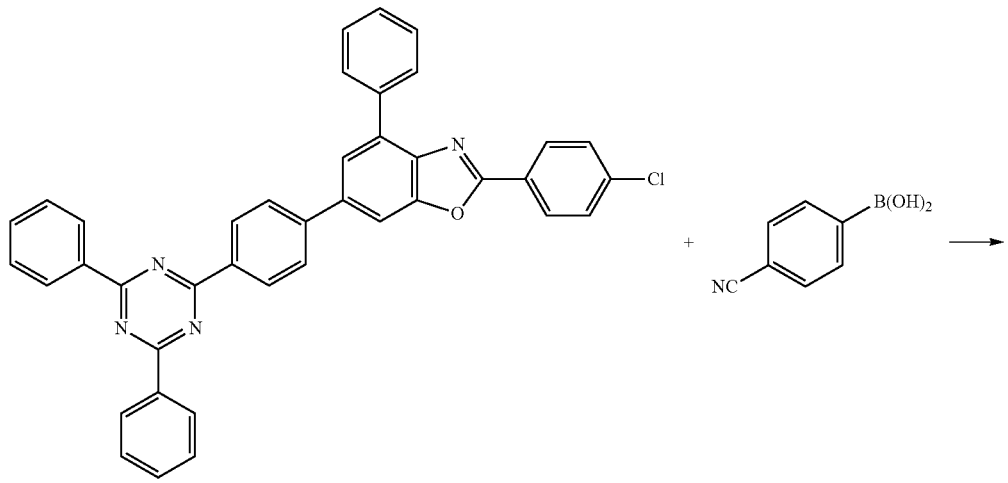

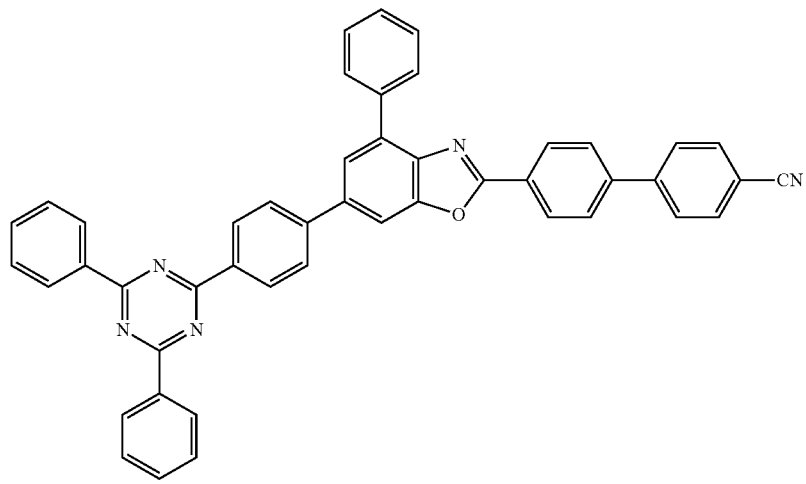

(Compound-75)

The structure of the obtained pale yellow powder was identified using NMR.

In $^1$H-NMR (CDCl$_3$), the following signals of 29 hydrogens were detected.

δ (ppm)=8.91 (2H), 8.83 (4H), 8.45 (2H), 8.17 (2H), 7.93 (2H), 7.91 (2H), 7.79 (4H), 7.77 (2H), 7.70-7.57 (8H), 7.51 (1H)

Example 8

Synthesis of 2-(4'-cyano-[1,1';4',1"]terphenyl-4-yl)-4-phenyl-6-{4-(pyridine-3-yl)-phenyl}-benzoxazole (Compound-77)

First, 10.6 g of 2-(4-chloro-phenyl)-4-phenyl-6-{4-(pyridine-3-yl)-phenyl}-benzoxazole, 7.4 g of 4'-(4,4,5,5-tetramethyl-[1,3,2]dioxaborolane-2-yl)biphenyl-4-carbonitrile, 0.6 g of tris(dibenzylideneacetone)dipalladium(0), 0.4 g of tricyclohexylphosphine, and 9.8 g of tripotassium phosphate were placed in a reaction vessel, and stirred in a mixed solvent of 1,4-dioxane/H$_2$O under reflux overnight. After allowing to cool, ethyl acetate and water were added to the system, followed by extraction and separation to obtain an organic layer, and the organic layer was concentrated. The obtained concentrate was purified through column chromatography (carrier: silica gel, eluent: dichloromethane/ethyl acetate) to thereby obtain 2.1 g (yield: 15%) of a pale yellow powder of 2-(4'-cyano-[1,1';4',1"]terphenyl-4-yl)-4-phenyl-6-{4-(pyridine-3-yl)-phenyl}-benzoxazole (Compound-77).

The structure of the obtained pale yellow powder was identified using NMR.

In $^1$H-NMR (CDCl$_3$), the following signals of 27 hydrogens were detected.

δ (ppm)=8.97 (1H), 8.66 (1H), 8.44 (2H), 8.16 (2H), 7.98 (1H), 7.90-7.71 (16H), 7.61 (2H), 7.49 (1H), 7.44 (1H)

Example 9

Synthesis of 2-(4'-cyano-biphenyl-4-yl)-6-{4-(4,6-diphenyl-[1,3,5]triazine-2-yl)-phenyl}-benzoxazole (Compound-84)

First, 15.0 g of 2-(4-chloro-phenyl)-6-{4-(4,6-diphenyl-[1,3,5]triazine-2-yl)-phenyl}-benzoxazole, 4.5 g of 4-cyanophenylboronic acid, 1.3 g of tris(dibenzylideneacetone)dipalladium(0), 1.6 g of tricyclohexylphosphine, and 17.8 g of tripotassium phosphate were placed in a reaction vessel, and stirred in a mixed solvent of 1,4-dioxane/H$_2$O under reflux overnight. After allowing to cool, methanol and water were added to the system for dispersing and washing, and the resulting system was filtered to obtain a crude product. The obtained crude product was purified through recrystallization from 1,2-dichlorobenzene as solvent to thereby obtain 5.3 g (yield: 31%) of a yellow powder of 2-(4'-cyano-biphenyl-4-yl)-6-{4-(4,6-diphenyl-[1,3,5] triazine-2-yl)-phenyl}-benzoxazole (Compound-84).

(Compound-77)

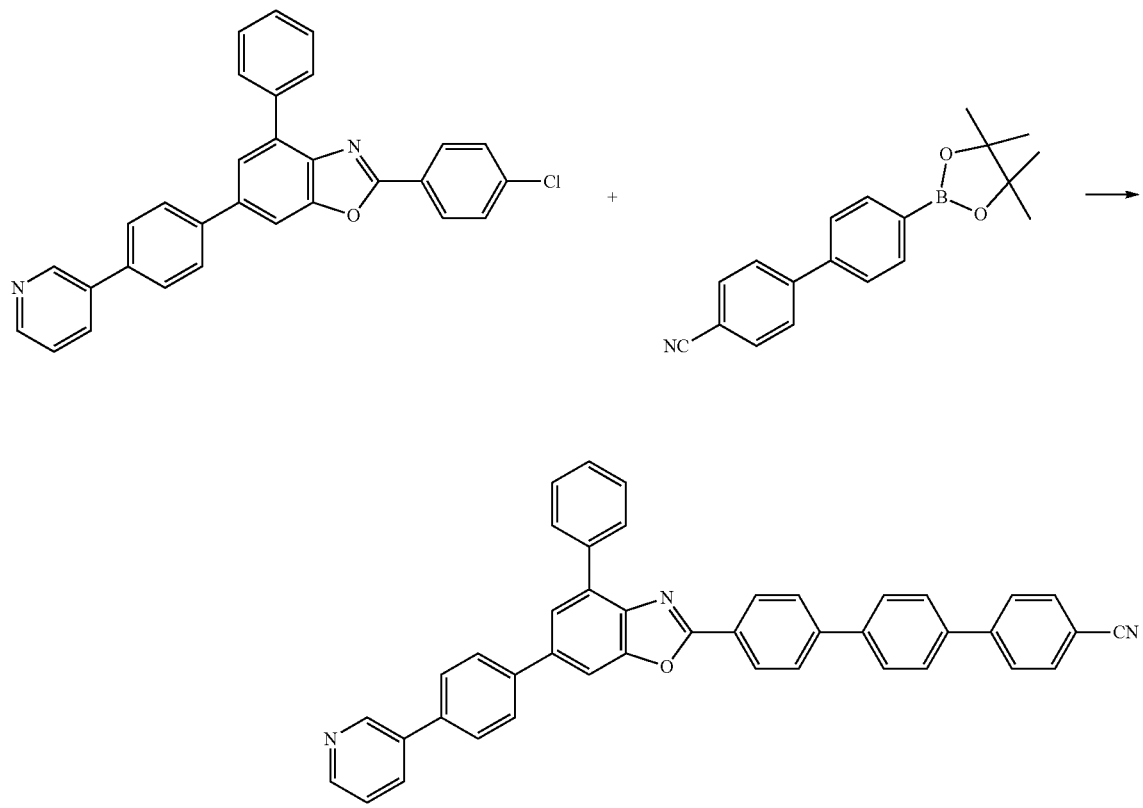

(Compound-84)

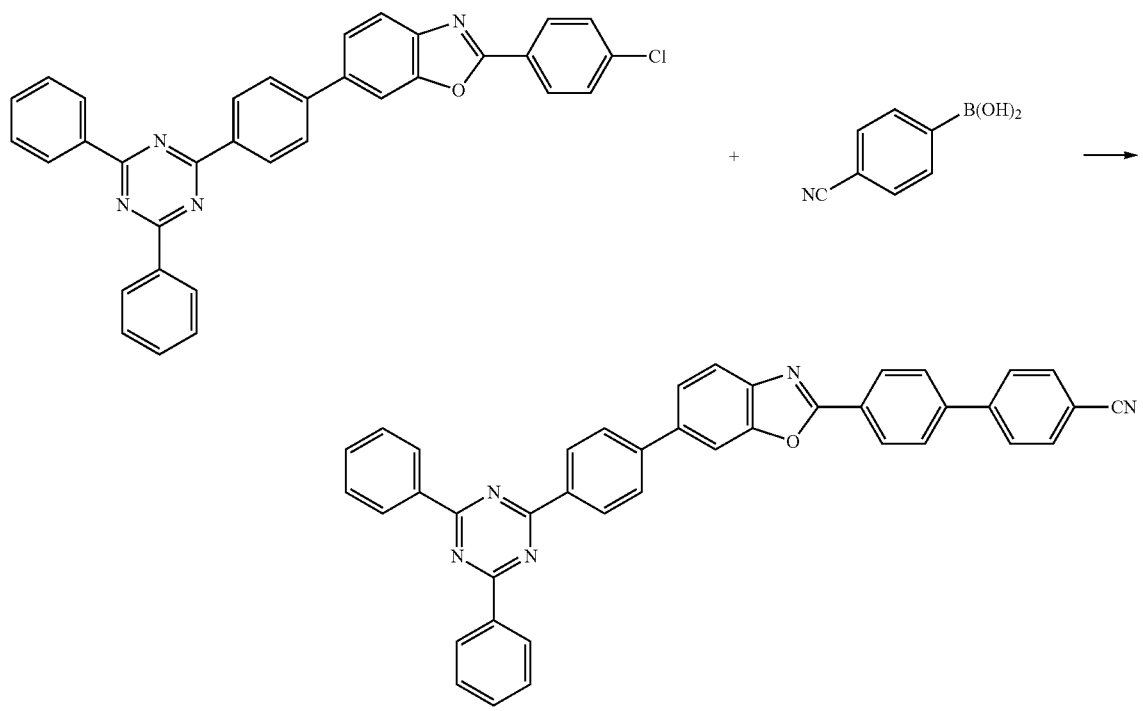

The structure of the obtained yellow powder was identified using NMR.

In $^1$H-NMR (CDCl$_3$), the following signals of 25 hydrogens were detected.

δ (ppm)=8.93 (2H), 8.84 (4H), 8.44 (2H), 7.97 (1H), 7.92 (3H), 7.85-7.75 (7H), 7.68-7.59 (6H)

Example 10

Synthesis of 4-(biphenyl-4-yl)-6-(4'-cyano-biphenyl-4-yl)-2-([1,1';4',1" ]terphenyl-4-yl)-benzoxazole (Compound-104)

First, 6.0 g of 6-chloro-4-(biphenyl-4-yl)-6-([1,1';4',1" ]terphenyl-4-yl)-benzoxazole, 4.1 g of 4'-(4,4,5,5-tetramethyl-[1,3,2]dioxaborolane-2-yl)biphenyl-4-carbonitrile, 0.3 g of tris(dibenzylideneacetone)dipalladium(0), 0.3 g of tricyclohexylphosphine, and 4.8 g of tripotassium phosphate were placed in a reaction vessel, and stirred in a mixed solvent of 1,4-dioxane/H$_2$O under reflux overnight. After allowing to cool, water was added to the system for dispersing and washing, and the resulting system was filtered to obtain a crude product. The obtained crude product was purified through crystallization from mixed a solvent of monochlorobenzene/acetone to thereby obtain 2.1 g (yield: 28%) of a pale yellow powder of 4-(biphenyl-4-yl)-6-(4'-cyano-biphenyl-4-yl)-2-([1,1';4',1" ]terphenyl-4-yl)-benzoxazole (Compound-104).

(Compound-104)

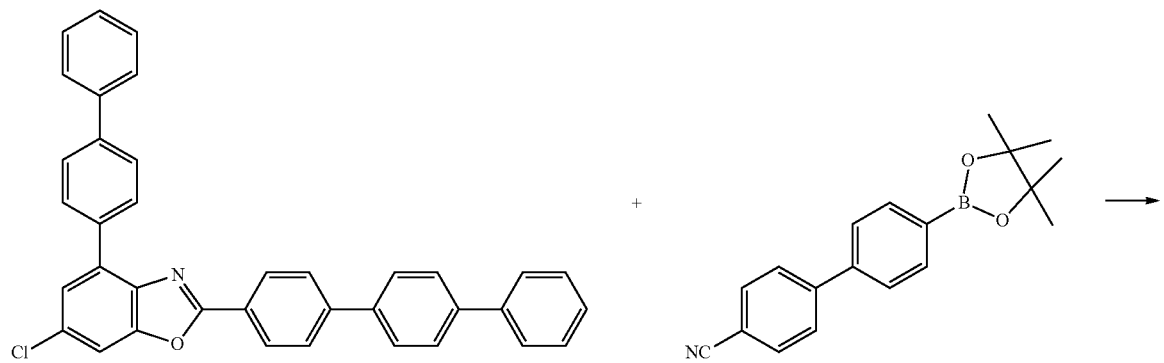

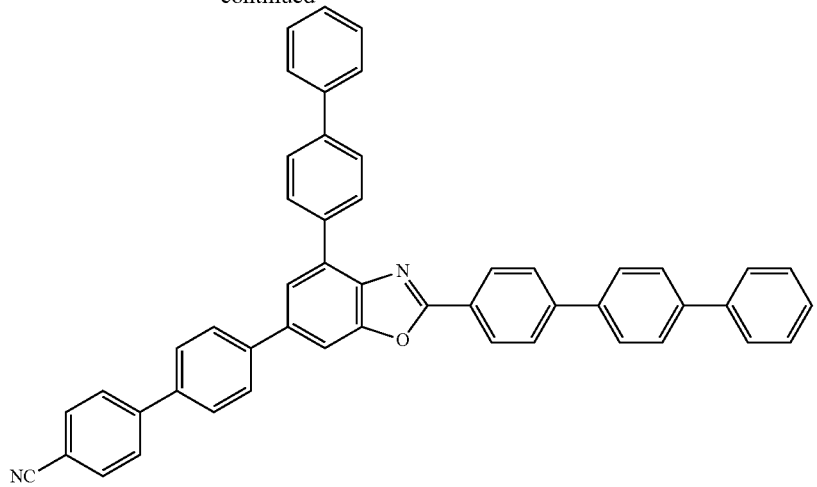

The structure of the obtained pale yellow powder was identified using NMR.

In $^1$H-NMR (CDCl$_3$), the following signals of 32 hydrogens were detected.

δ (ppm)=8.44 (2H), 8.26 (2H), 7.91-7.66 (22H), 7.52 (4H), 7.42 (2H)

Example 11

Synthesis of 4,6-bis(4'-cyano-biphenyl-4-yl)-2-(biphenyl-4-yl)-benzoxazole (Compound-105)

First, 6.0 g of 4-bromo-6-chloro-2-(biphenyl-4-yl)-benzoxazole, 8.0 g of 4'-(4,4,5,5-tetramethyl-[1,3,2]dioxaborolane-2-yl)biphenyl-4-carbonitrile, 0.7 g of tris(dibenzylideneacetone)dipalladium(0), 0.7 g of tricyclohexylphosphine, and 10.6 g of tripotassium phosphate were placed in a reaction vessel, and stirred in a mixed solvent of 1,4-dioxane/H$_2$O under reflux overnight. After allowing to cool, methanol was added to the system for dispersing and washing, and the resulting system was filtered to obtain a crude product. The obtained crude product was purified through recrystallization from monochlorobenzene as solvent to thereby obtain 4.5 g (yield: 58%) of a pale yellow powder of 4,6-bis(4'-cyano-biphenyl-4-yl)-2-(biphenyl-4-yl)-benzoxazole (Compound-105).

(Compound-105)

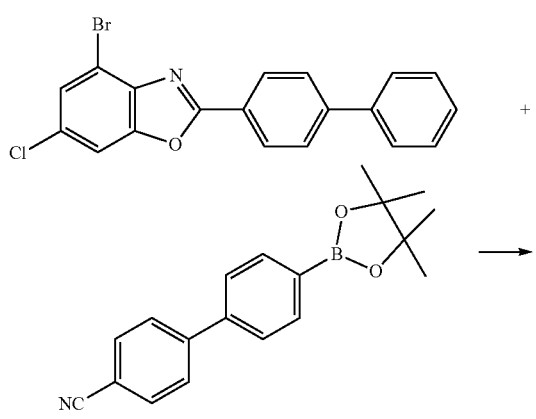

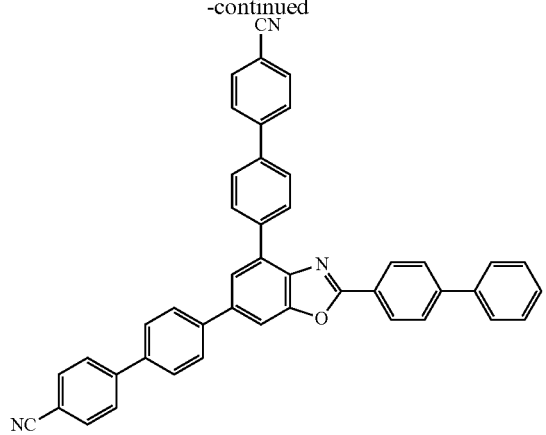

The structure of the obtained pale yellow powder was identified using NMR.

In $^1$H-NMR (CDCl$_3$), the following signals of 27 hydrogens were detected.

δ (ppm)=8.41 (2H), 8.29 (2H), 7.90-7.67 (20H), 7.52 (2H), 7.45 (1H)

Example 12

Synthesis of 6-(4'-cyano-biphenyl-4-yl)-2-(4'-cyano-[1,1';4',1"]terphenyl-4-yl)-4-phenyl-benzoxazole (Compound-106)

First, 14.0 g of 6-chloro-2-(4-chloro-phenyl)-4-phenyl-benzoxazole, 23.3 g of 4'-(4,4,5,5-tetramethyl-[1,3,2]dioxaborolane-2-yl)biphenyl-4-carbonitrile, 2.0 g of tris(dibenzylideneacetone)dipalladium(0), 2.0 g of tricyclohexylphosphine, and 23.2 g of tripotassium phosphate were placed in a reaction vessel, and stirred in a mixed solvent of 1,4-dioxane/H$_2$O under reflux overnight. After allowing to cool, ethyl acetate and water were added to the system, followed by extraction and separation to obtain an organic layer, and the organic layer was concentrated. The obtained concentrate was purified through column chromatography (carrier: silica gel, eluent: dichloromethane/ethyl acetate) to thereby obtain 4.6 g (yield: 20%) of a pale yellow powder of 6-(4'-cyano-biphenyl-4-yl)-2-(4'-cyano-[1,1';4',1"]terphenyl-4-yl)-4-phenyl-benzoxazole (Compound-106).

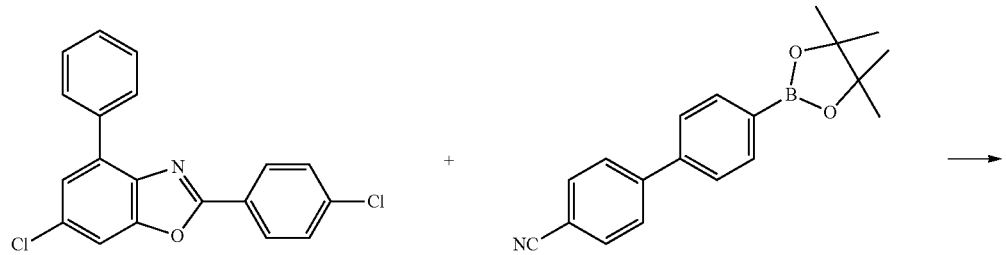
(Compound-106)

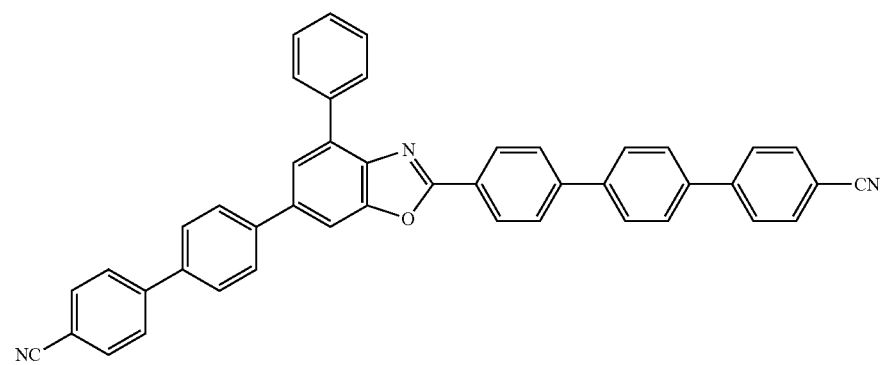

The structure of the obtained pale yellow powder was identified using NMR.

In $^1$H-NMR (CDCl$_3$), the following signals of 27 hydrogens were detected.

δ (ppm)=8.46 (2H), 8.15 (2H), 7.90-7.72 (20H), 7.61 (2H), 7.50 (1H)

Example 13

Synthesis of 4,6-bis(biphenyl-4-yl)-2-(4'-cyano-biphenyl-3-yl)-benzoxazole (Compound-108)

First, 10.5 g of 4,6-bis(biphenyl-4-yl)-2-(3-chloro-phenyl)-benzoxazole, 3.0 g of 4-cyanophenylboronic acid, 0.5 g of tris(dibenzylideneacetone)dipalladium(0), 0.6 g of tricyclohexylphosphine, and 8.3 g of tripotassium phosphate were placed in a reaction vessel, and stirred in a mixed solvent of 1,4-dioxane/H$_2$O under reflux overnight. After allowing to cool, methanol was added to the system for dispersing and washing, and the resulting system was filtered to obtain a crude product. The obtained crude product was purified through recrystallization from monochlorobenzene as solvent to thereby obtain 9.6 g (yield: 81%) of a white powder of 4,6-bis(biphenyl-4-yl)-2-(4'-cyano-biphenyl-3-yl)-benzoxazole (Compound-108).

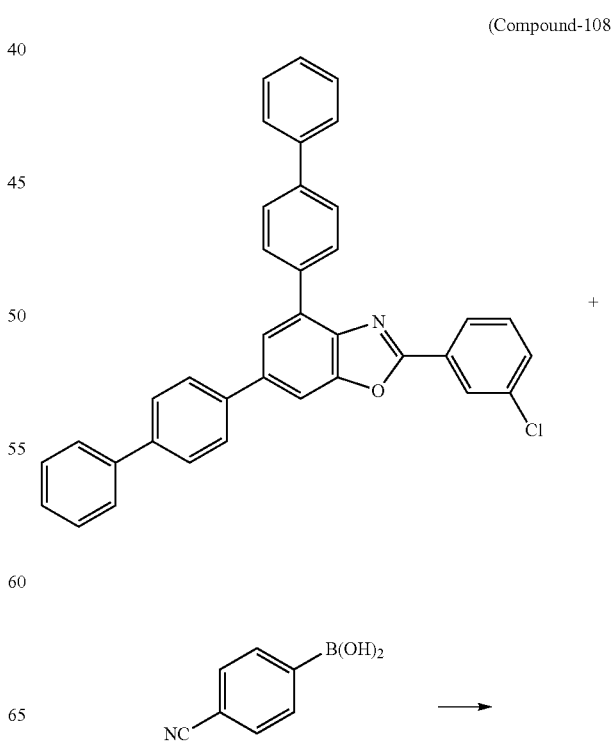
(Compound-108)

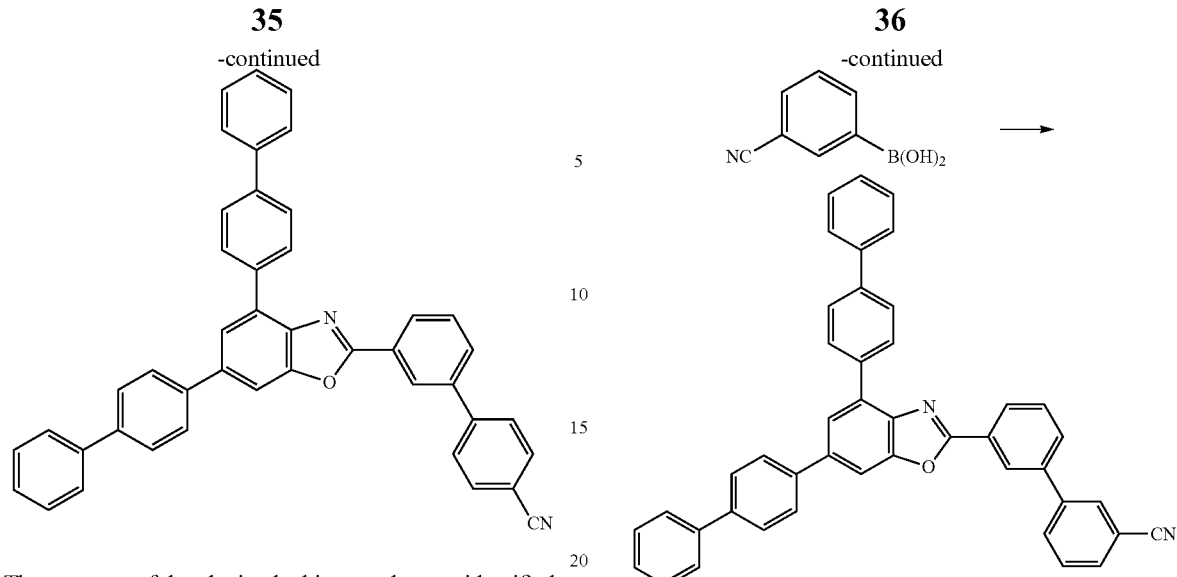

The structure of the obtained white powder was identified using NMR.

In $^1$H-NMR (CDCl$_3$), the following signals of 28 hydrogens were detected.

δ (ppm)=8.57 (1H), 8.41 (1H), 8.23 (2H), 7.92 (1H), 7.88-7.65 (17H), 7.52 (4H), 7.42 (2H)

Example 14

Synthesis of 4,6-bis(biphenyl-4-yl)-2-(3'-cyano-biphenyl-3-yl)-benzoxazole (Compound-109)

First, 9.6 g of 4,6-bis(biphenyl-4-yl)-2-(3-chloro-phenyl)-benzoxazole, 5.3 g of 3-cyanophenylboronic acid, 0.5 g of tris(dibenzylideneacetone)dipalladium(0), 0.5 g of tricyclohexylphosphine, and 7.6 g of tripotassium phosphate were placed in a reaction vessel, and stirred in a mixed solvent of 1,4-dioxane/H$_2$O under reflux overnight. After allowing to cool, methanol was added to the system for dispersing and washing, and the resulting system was filtered to obtain a crude product. The obtained crude product was purified through recrystallization from monochlorobenzene as solvent to thereby obtain 2.6 g (yield: 24%) of a white powder of 4,6-bis(biphenyl-4-yl)-2-(3'-cyano-biphenyl-3-yl)-benzoxazole (Compound-109).

(Compound-109)

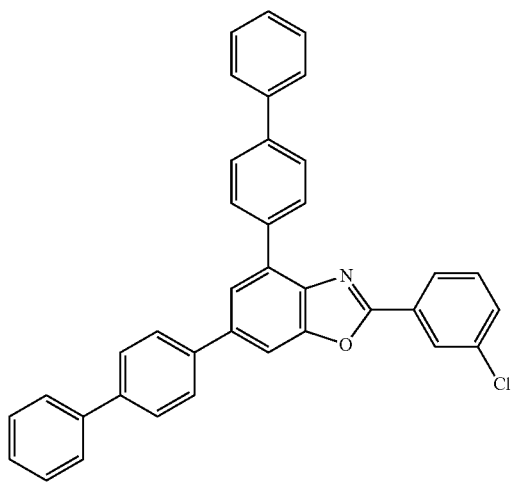

+

The structure of the obtained white powder was identified using NMR.

In $^1$H-NMR (CDCl$_3$), the following signals of 28 hydrogens were detected.

δ (ppm)=8.55 (1H), 8.41 (1H), 8.24 (2H), 8.02 (1H), 7.96 (1H), 7.92 (1H), 7.88 (1H), 7.86-7.60 (14H), 7.52 (4H), 7.42 (2H)

Example 15

Synthesis of 4,6-bis(4-naphthalene-1-yl-phenyl)-2-(3'-cyano-biphenyl-4-yl)-benzoxazole (Compound-110)

First, 7.0 g of 4,6-bis(4-naphthalene-1-yl-phenyl)-2-(4-chloro-phenyl)-benzoxazole, 1.8 g of 3-cyanophenylboronic acid, 0.3 g of tris(dibenzylideneacetone)dipalladium(0), 0.3 g of tricyclohexylphosphine, and 7.0 g of tripotassium phosphate were placed in a reaction vessel, and stirred in a mixed solvent of 1,4-dioxane/H$_2$O under reflux overnight. After allowing to cool, toluene and water were added to the system, followed by extraction and separation to obtain an organic layer, and the organic layer was concentrated. The obtained concentrate was purified through column chromatography (carrier: silica gel, eluent: toluene/n-heptane) to thereby obtain 5.5 g (yield: 71%) of a pale yellow powder of 4,6-bis(4-naphthalene-1-yl-phenyl)-2-(3'-cyano-biphenyl-4-yl)-benzoxazole (Compound-110).

(Compound-110)

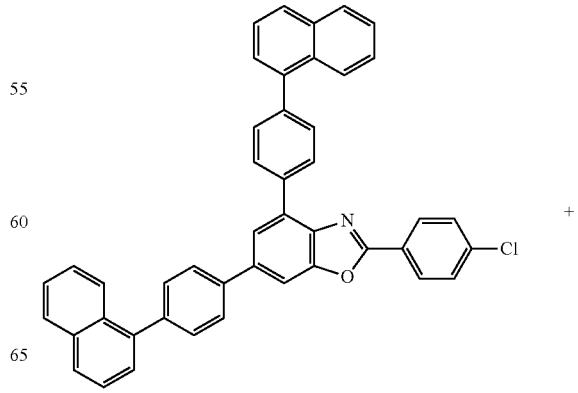

+

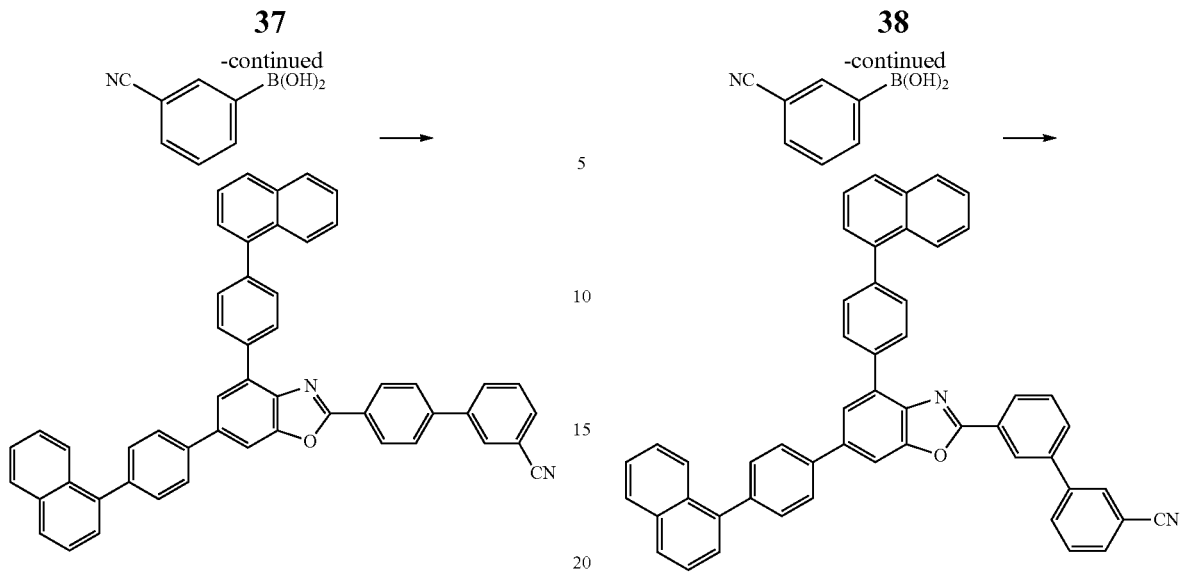

The structure of the obtained pale yellow powder was identified using NMR.

In $^1$H-NMR (CDCl$_3$), the following signals of 32 hydrogens were detected.

δ (ppm)=8.51 (2H), 8.33 (2H), 8.13 (1H), 8.06 (1H), 8.04 (1H), 8.01-7.84 (9H), 7.77 (3H), 7.71 (3H), 7.66-7.41 (10H)

Example 16

Synthesis of 4,6-bis(4-naphthalene-1-yl-phenyl)-2-(3'-cyano-biphenyl-3-yl)-benzoxazole (Compound-111)

First, 12.0 g of 4,6-bis(4-naphthalene-1-yl-phenyl)-2-(3-chloro-phenyl)-benzoxazole, 3.3 g of 3-cyanophenylboronic acid, 0.5 g of tris(dibenzylideneacetone)dipalladium(0), 0.5 g of tricyclohexylphosphine, and 8.0 g of tripotassium phosphate were placed in a reaction vessel, and stirred in a mixed solvent of 1,4-dioxane/H$_2$O under reflux overnight. After allowing to cool, methanol was added to the system for dispersing and washing, and the resulting system was filtered to obtain a crude product. The obtained crude product was purified through recrystallization from toluene as solvent to thereby obtain 10.0 g (yield: 76%) of a white powder of 4,6-bis(4-naphthalene-1-yl-phenyl)-2-(3'-cyano-biphenyl-3-yl)-benzoxazole (Compound-111).

The structure of the obtained white powder was identified using NMR.

In $^1$H-NMR (CDCl$_3$), the following signals of 32 hydrogens were detected.

δ (ppm)=8.58 (1H), 8.45 (1H), 8.32 (2H), 8.13 (1H), 8.05 (1H), 8.04 (2H), 7.98 (3H), 7.95 (2H), 7.91 (3H), 7.81-7.65 (8H), 7.62 (2H), 7.59-7.48 (6H)

Example 17

Synthesis of 4,6-bis(phenanthrene-9-yl)-2-(3'-cyano-biphenyl-4-yl)-benzoxazole (Compound-115)

First, 10.0 g of 2-(4-chloro-phenyl)-4,6-bis(phenanthrene-9-yl)-benzoxazole, 3.0 g of 3-cyanophenylboronic acid, 0.5 g of tris(dibenzylideneacetone)dipalladium (0), 0.5 g of tricyclohexylphosphine, and 7.3 g of tripotassium phosphate were placed in a reaction vessel, and stirred in a mixed solvent of 1,4-dioxane/H$_2$O under reflux overnight. After allowing to cool, methanol was added to the system for dispersing and washing, and the resulting system was filtered to obtain a crude product. The obtained crude product was purified through recrystallization from toluene as solvent to thereby obtain 8.4 g (yield: 75%) of a white powder of 4,6-bis(phenanthrene-9-yl)-2-(3'-cyano-biphenyl-4-yl)-benzoxazole (Compound-115).

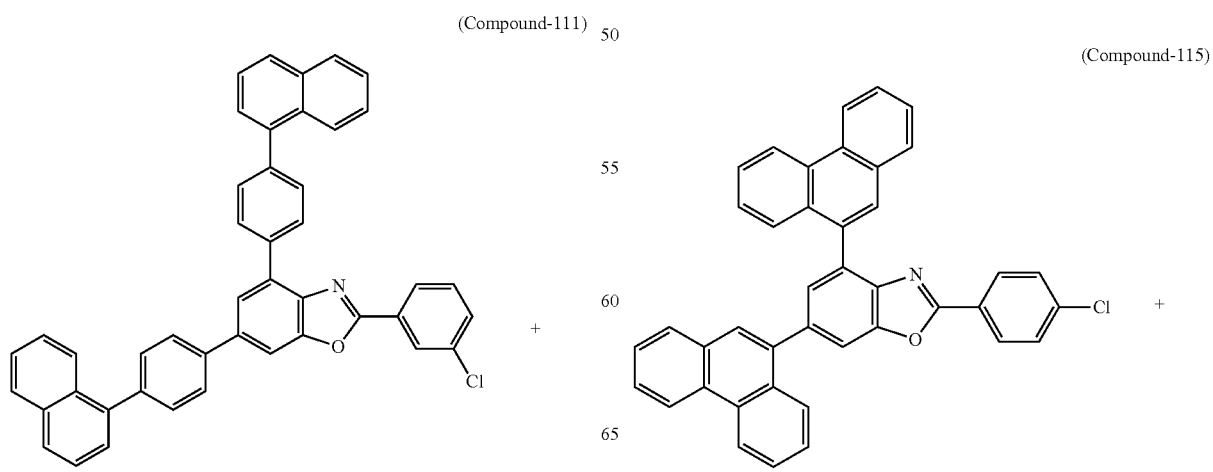

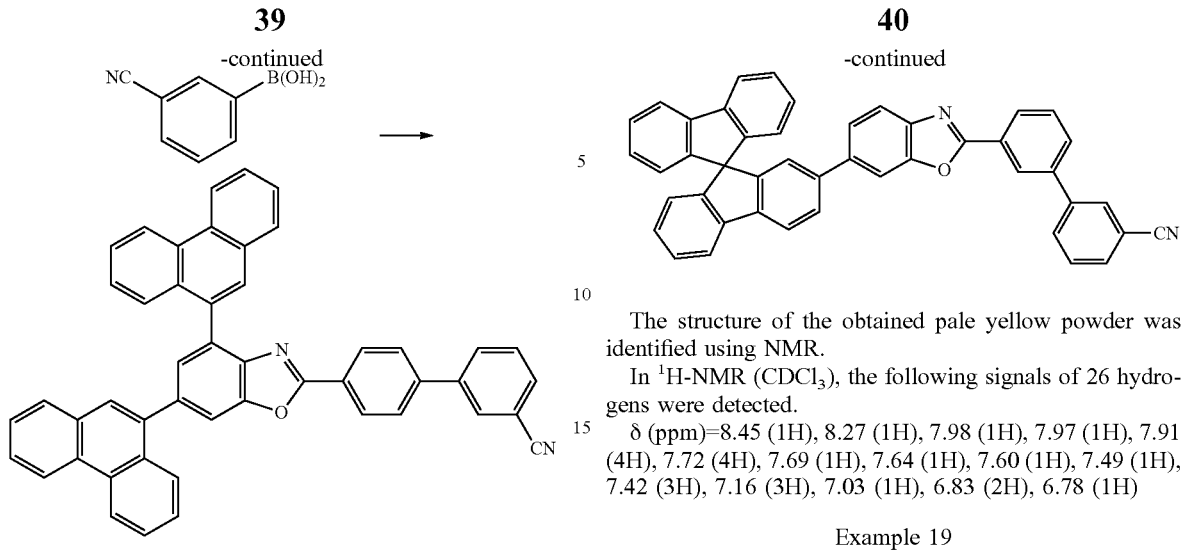

The structure of the obtained white powder was identified using NMR.

In $^1$H-NMR (CDCl$_3$), the following signals of 28 hydrogens were detected.

δ (ppm)=8.84 (2H), 8.79 (2H), 8.35 (2H), 8.18 (1H), 8.06 (1H), 8.05 (1H), 7.98 (2H), 7.92 (3H), 7.86 (1H), 7.78 (1H), 7.77-7.65 (9H), 7.62 (2H), 7.58 (1H)

Example 18

Synthesis of 2-(3'-cyano-biphenyl-3-yl)-6-(9,9'-spirobi[9H]fluorene-2-yl)-benzoxazole (Compound-117)

First, 10.5 g of 2-(3-chloro-phenyl)-6-(9,9'-spirobi[9H]fluorene-2-yl)-benzoxazole, 3.0 g of 3-cyanophenylboronic acid, 0.5 g of tris(dibenzylideneacetone)dipalladium(0), 0.5 g of tricyclohexylphosphine, and 8.2 g of tripotassium phosphate were placed in a reaction vessel, and stirred in a mixed solvent of 1,4-dioxane/H$_2$O under reflux overnight. After allowing to cool, ethyl acetate and water were added to the system, followed by extraction and separation to obtain an organic layer, and the organic layer was concentrated. The obtained concentrate was purified through column chromatography (carrier: silica gel, eluent: dichloromethane/n-heptane) to thereby obtain 5.0 g (yield: 48%) of a pale yellow powder of 2-(3'-cyano-biphenyl-3-yl)-6-(9, 9'-spirobi[9H]fluorene-2-yl)-benzoxazole (Compound-117).

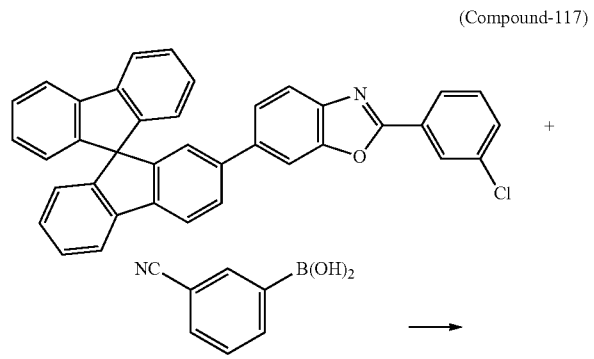

The structure of the obtained pale yellow powder was identified using NMR.

In $^1$H-NMR (CDCl$_3$), the following signals of 26 hydrogens were detected.

δ (ppm)=8.45 (1H), 8.27 (1H), 7.98 (1H), 7.97 (1H), 7.91 (4H), 7.72 (4H), 7.69 (1H), 7.64 (1H), 7.60 (1H), 7.49 (1H), 7.42 (3H), 7.16 (3H), 7.03 (1H), 6.83 (2H), 6.78 (1H)

Example 19

Synthesis of 6-(9,9-diphenyl-9H-fluorene-3-yl)-2-(3'-cyano-biphenyl-3-yl)-benzoxazole (Compound-118)

First, 10.5 g of 2-(3-chloro-phenyl)-6-(9,9-diphenyl-9H-fluorene-3-yl)-benzoxazole, 3.0 g of 3-cyanophenylboronic acid, 0.5 g of tris(dibenzylideneacetone)dipalladium(0), 0.5 g of tricyclohexylphosphine, and 8.2 g of tripotassium phosphate were placed in a reaction vessel, and stirred in a mixed solvent of 1,4-dioxane/H$_2$O under reflux overnight. After allowing to cool, methanol was added to the system for dispersing and washing, and the resulting system was filtered to obtain a crude product. The obtained crude product was purified through recrystallization from monochlorobenzene as solvent to thereby obtain 6.4 g (yield: 54%) of a white powder of 6-(9,9-diphenyl-9H-fluorene-3-yl)-2-(3'-cyano-biphenyl-3-yl)-benzoxazole (Compound-118).

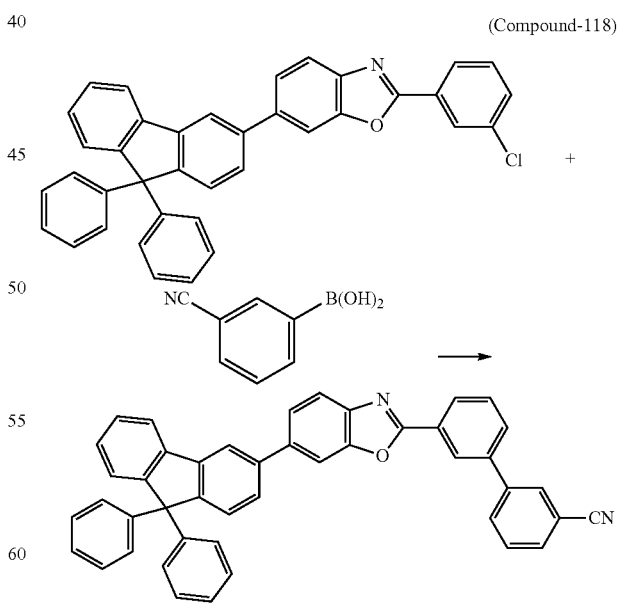

The structure of the obtained white powder was identified using NMR.

In $^1$H-NMR (CDCl$_3$), the following signals of 28 hydrogens were detected.

δ (ppm)=8.53 (1H), 8.35 (1H), 8.03 (2H), 7.97 (1H), 7.90 (2H), 7.88 (1H), 7.76 (2H), 7.72 (2H), 7.65 (1H), 7.56 (2H), 7.45 (2H), 7.38-7.22 (11H)

Example 20

Synthesis of 6-(9,9-diphenyl-9H-fluorene-4-yl)-2-(3'-cyano-biphenyl-3-yl)-benzoxazole (Compound-119)

First, 10.5 g of 2-(3-chloro-phenyl)-6-(9,9-diphenyl-9H-fluorene-4-yl)-benzoxazole, 3.0 g of 3-cyanophenylboronic acid, 0.5 g of tris(dibenzylideneacetone)dipalladium(0), 0.5 g of tricyclohexylphosphine, and 8.2 g of tripotassium phosphate were placed in a reaction vessel, and stirred in a mixed solvent of 1,4-dioxane/H$_2$O under reflux overnight. After allowing to cool, methanol was added to the system for dispersing and washing, and the resulting system was filtered to obtain a crude product. The obtained crude product was purified through crystallization from a mixed solvent of toluene/acetone to thereby obtain 6.4 g (yield: 54%) of a white powder of 6-(9,9-diphenyl-9H-fluorene-4-yl)-2-(3'-cyano-biphenyl-3-yl)-benzoxazole (Compound-119).

(Compound-119)

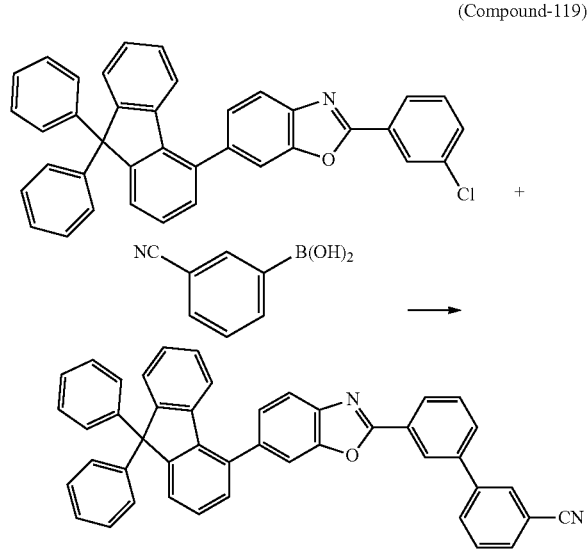

The structure of the obtained white powder was identified using NMR.

In $^1$H-NMR (CDCl$_3$), the following signals of 28 hydrogens were detected.

δ (ppm)=8.55 (1H), 8.38 (1H), 8.03 (1H), 7.98 (1H), 7.94 (1H), 7.79 (2H), 7.74 (1H), 7.72 (1H), 7.65 (1H), 7.58 (1H), 7.50 (1H), 7.42 (1H), 7.35 (2H), 7.32-7.23 (10H), 7.20 (1H), 7.03 (1H), 6.92 (1H)

Example 21

Synthesis of 2-(4"-cyano-[1,1';4',1"]terphenyl-4-yl)-4,6-diphenyl-benzoxazole (Compound-120)

First, 8.8 g of 2-(4-chloro-phenyl)-4,6-diphenyl-benzoxazole, 8.4 g of 4'-(4,4,5,5-tetramethyl-[1,3,2]dioxaborolane-2-yl)biphenyl-4-carbonitrile, 1.1 g of tris(dibenzylideneacetone)dipalladium(0), 1.3 g of tricyclohexylphosphine, and 14.7 g of tripotassium phosphate were placed in a reaction vessel, and stirred in a mixed solvent of 1,4-dioxane/H$_2$O under reflux overnight. After allowing to cool, water was added to the system for dispersing and washing, and the resulting system was filtered to obtain a crude product. The obtained crude product was purified through recrystallization from monochlorobenzene as solvent to thereby obtain 11.5 g (yield: 95%) of a pale yellow powder of 2-(4"-cyano-[1,1';4',1"]terphenyl-4-yl)-4,6-diphenyl-benzoxazole (Compound-120).

(Compound-120)

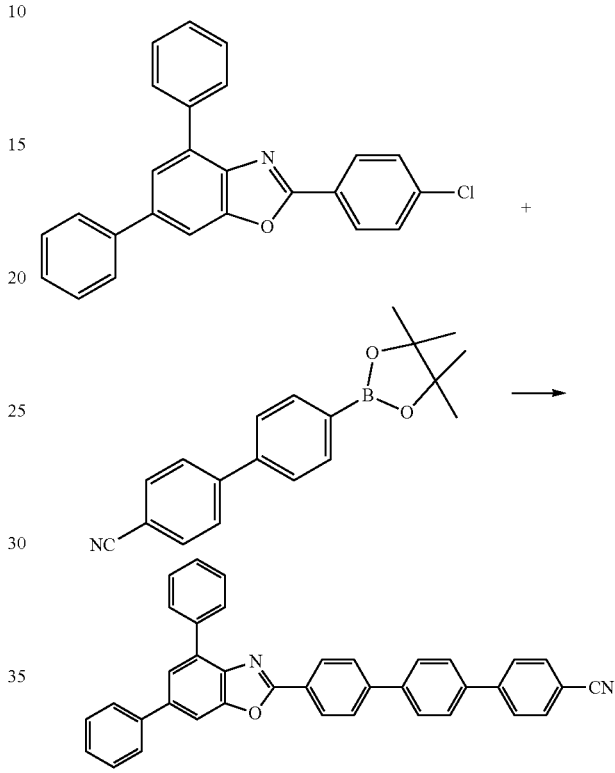

The structure of the obtained pale yellow powder was identified using NMR.

In $^1$H-NMR (CDCl$_3$), the following signals of 24 hydrogens were detected.

δ (ppm)=8.41 (2H), 8.16 (2H), 7.89-7.67 (14H), 7.65-7.38 (6H)

Example 22

Synthesis of 2-(4"-cyano-[1,1';4',1"]terphenyl-4-yl)-6-(9,9'-spirobi[9H]fluorene-4-yl)-benzoxazole (Compound-123)

First, 6.5 g of 2-(4-chloro-phenyl)-6-(9,9'-spirobi[9H]fluorene-4-yl)-benzoxazole, 4.0 g of 4'-(4,4,5,5-tetramethyl-[1,3,2]dioxaborolane-2-yl)biphenyl-4-carbonitrile, 0.3 g of tris(dibenzylideneacetone)dipalladium(0), 0.3 g of tricyclohexylphosphine, and 7.6 g of tripotassium phosphate were placed in a reaction vessel, and stirred in a mixed solvent of 1,4-dioxane/H$_2$O under reflux overnight. After allowing to cool, water was added to the system for dispersing and washing, and the resulting system was filtered to obtain a crude product. The obtained crude product was purified through crystallization from a mixed solvent of monochlorobenzene/acetone to thereby obtain 7.5 g (yield: 91%) of a pale yellow powder of 2-(4"-cyano-[1,1';4',1"]terphenyl-4-yl)-6-(9,9'-spirobi[9H]fluorene-4-yl)-benzoxazole (Compound-123).

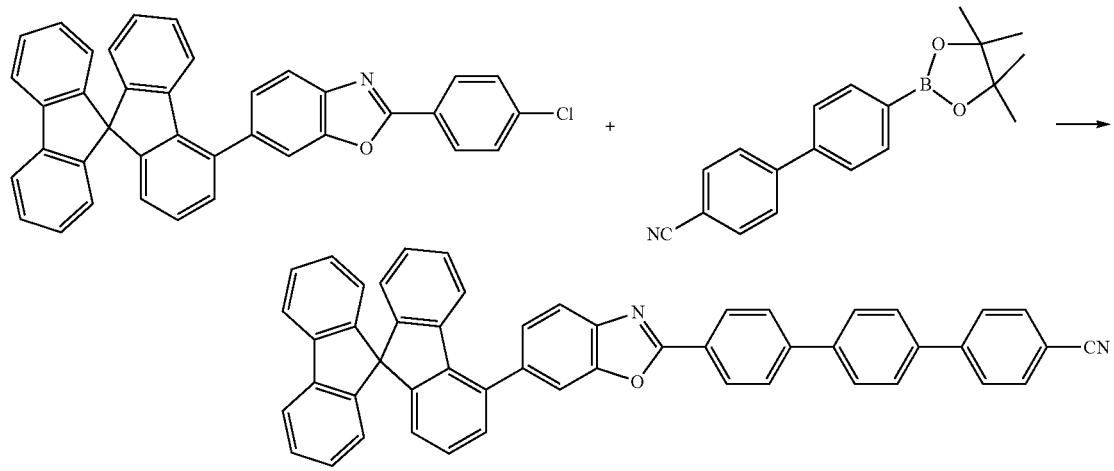
(Compound-123)

The structure of the obtained pale yellow powder was identified using NMR.

In $^1$H-NMR (CDCl$_3$), the following signals of 30 hydrogens were detected.

δ (ppm)=8.46 (2H), 8.00 (1H), 7.90 (2H), 7.89 (2H), 7.85 (3H), 7.80 (4H), 7.76 (2H), 7.68 (1H), 7.42 (2H), 7.30 (1H), 7.19 (3H), 7.05 (3H), 6.86 (2H), 6.79 (1H), 6.74 (1H)

Example 23

Synthesis of 2-(4"-cyano-[1,1';4',1"]terphenyl-3-yl)-4,6-diphenyl-benzoxazole (Compound-127)

First, 7.1 g of 2-(3-chloro-phenyl)-4,6-diphenyl-benzoxazole, 6.2 g of 4'-(4,4,5,5-tetramethyl-[1,3,2]dioxaborolane-2-yl)biphenyl-4-carbonitrile, 0.5 g of tris(dibenzylideneacetone)dipalladium(0), 0.5 g of tricyclohexylphosphine, and 7.9 g of tripotassium phosphate were placed in a reaction vessel, and stirred in a mixed solvent of 1,4-dioxane/H$_2$O under reflux overnight. After allowing to cool, methanol was added to the system for dispersing and washing, and the resulting system was filtered to obtain a crude product. The obtained crude product was purified through recrystallization from 1,2-dichlorobenzene as solvent to thereby obtain 5.3 g (yield: 54%) of a white powder of 2-(4"-cyano-[1,1'; 4',1"]terphenyl-3-yl)-4,6-diphenyl-benzoxazole (Compound-127).

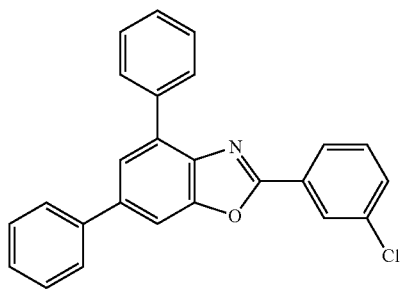
(Compound-127)

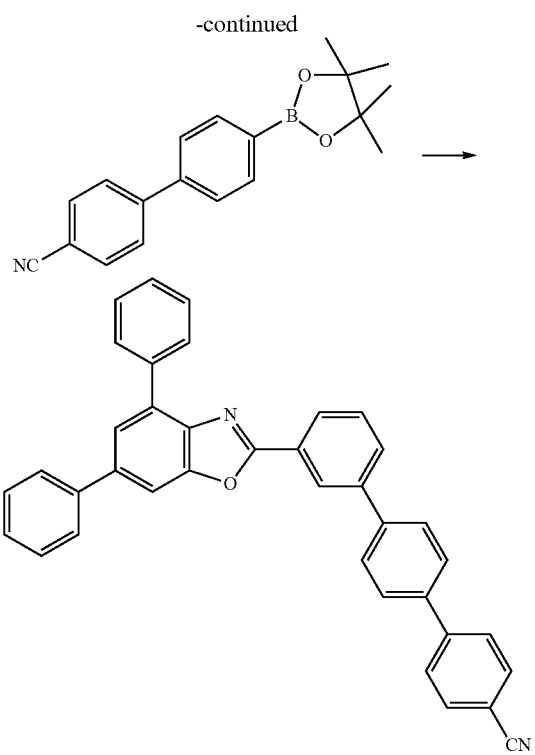
-continued

The structure of the obtained white powder was identified using NMR.

In $^1$H-NMR (CDCl$_3$), the following signals of 24 hydrogens were detected.

δ (ppm)=8.60 (1H), 8.36 (1H), 8.14 (2H), 7.89-7.71 (13H), 7.67 (1H), 7.63-7.40 (6H)

Example 24

Synthesis of 4,6-bis(biphenyl-4-yl)-2-(4"-cyano-[1,1';4',1"]terphenyl-3-yl)-benzoxazole (Compound-128)

First, 8.0 g of 4,6-bis(biphenyl-4-yl)-2-(3-chloro-phenyl)-benzoxazole, 4.8 g of 4'-(4,4,5,5-tetramethyl-[1,3,2]dioxaborolane-2-yl)biphenyl-4-carbonitrile, 0.4 g of tris(dibenzylideneacetone)dipalladium(0), 0.4 g of tricyclohexylphosphine, and 6.4 g of tripotassium phosphate were placed in a reaction vessel, and stirred in a mixed solvent of 1,4-dioxane/H$_2$O under reflux overnight. After allowing to cool, methanol was added to the system for dispersing and washing, and the resulting system was filtered to obtain a crude product. The obtained crude product was purified through recrystallization from 1,2-dichlorobenzene as solvent to thereby obtain 7.2 g (yield: 71%) of a white powder of 4,6-bis(biphenyl-4-yl)-2-(4"-cyano-[1,1';4',1"]terphenyl-3-yl)-benzoxazole (Compound-128).

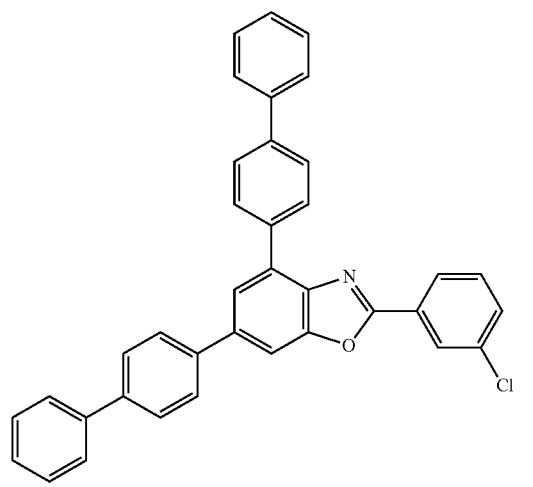

The structure of the obtained white powder was identified using NMR.

In $^1$H-NMR (CDCl$_3$), the following signals of 32 hydrogens were detected.

δ (ppm)=8.64 (1H), 8.38 (1H), 8.25 (2H), 7.92 (1H), 7.89-7.81 (8H), 7.81-7.64 (13H), 7.52 (4H), 7.42 (2H)

Example 25

Synthesis of 2-(4"-cyano-[1,1';4',1"]terphenyl-3-yl)-4,6-di(naphthalene-1-yl)-benzoxazole (Compound-130)

First, 9.1 g of 2-(3-chloro-phenyl)-4,6-di(naphthalene-1-yl)-benzoxazole, 6.1 g of 4'-(4,4,5,5-tetramethyl-[1,3,2]dioxaborolane-2-yl)biphenyl-4-carbonitrile, 0.5 g of tris(dibenzylideneacetone)dipalladium(0), 0.5 g of tricyclohexylphosphine, and 8.0 g of tripotassium phosphate were placed in a reaction vessel, and stirred in a mixed solvent of 1,4-dioxane/H$_2$O under reflux overnight. After allowing to cool, methanol was added to the system for dispersing and washing, and the resulting system was filtered to obtain a crude product. The obtained crude product was purified through recrystallization from monochlorobenzene as solvent to thereby obtain 1.8 g (yield: 15%) of a white powder of 2-(4"-cyano-[1,1';4',1"]terphenyl-3-yl)-4,6-di(naphthalene-1-yl)-benzoxazole (Compound-130).

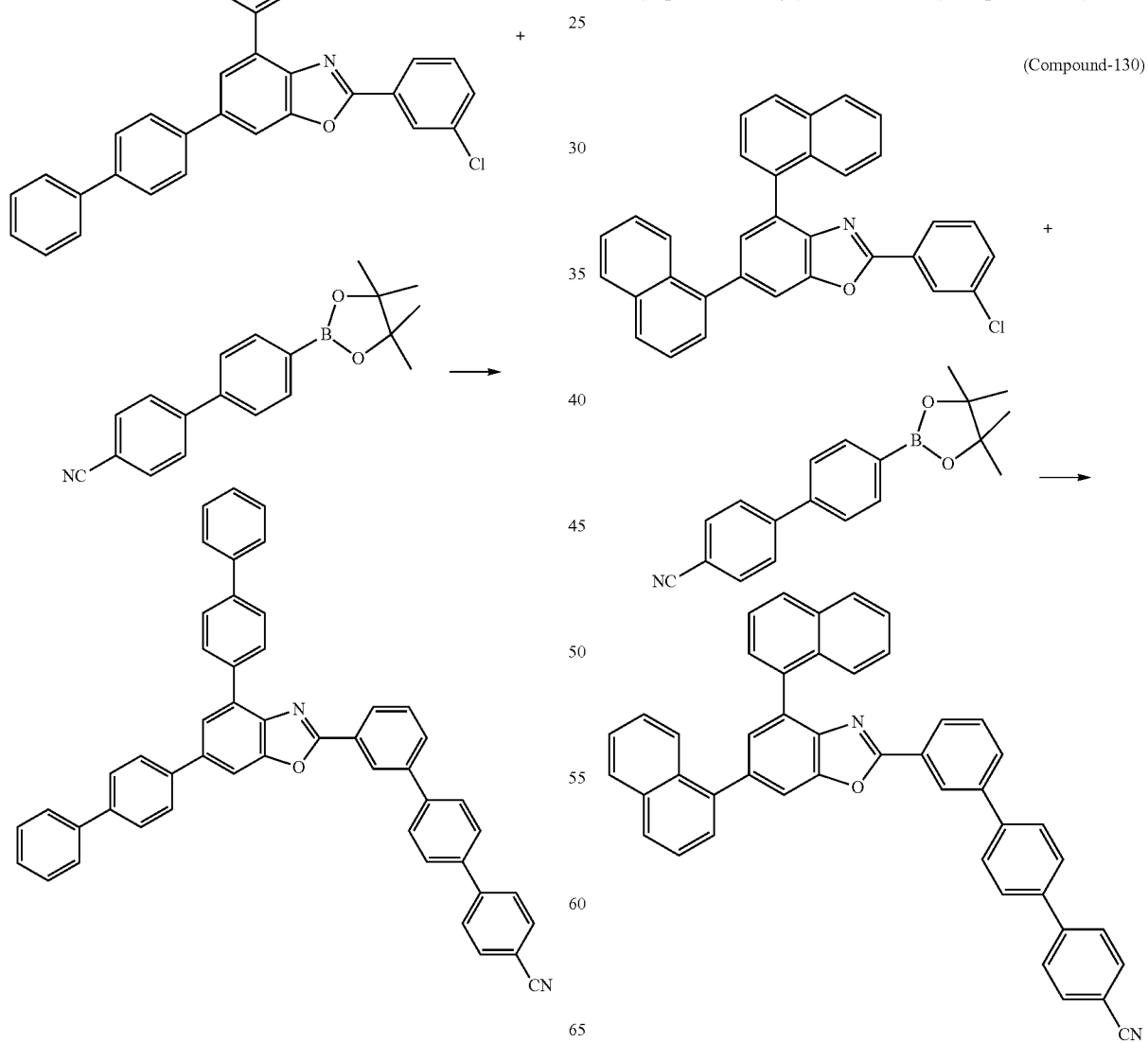

The structure of the obtained white powder was identified using NMR.

In $^1$H-NMR (CDCl$_3$), the following signals of 28 hydrogens were detected.

δ (ppm)=8.53 (1H), 8.28 (1H), 8.15 (1H), 8.03 (1H), 7.97 (3H), 7.94 (1H), 7.86 (1H), 7.84-7.73 (8H), 7.68 (4H), 7.65-7.42 (7H)

The structure of the obtained yellow powder was identified using NMR.

In $^1$H-NMR (CDCl$_3$), the following signals of 28 hydrogens were detected.

δ (ppm)=8.84 (1H), 8.79 (1H), 8.44 (2H), 7.97 (2H), 7.94 (1H), 7.88 (2H), 7.86-7.77 (12H), 7.75 (3H), 7.67 (2H), 7.60 (2H)

Example 26

Synthesis of 2-(4'''-cyano-[1,1';4',1'';4'',1''']quaterphenyl-4-yl)-6-(phenanthrene-9-yl)-benzoxazole (Compound-136)

First, 10.0 g of 2-(4-chloro-phenyl)-6-(phenanthrene-9-yl)-benzoxazole, 11.3 g of 4-(4-(4,4,5,5-tetramethyl-[1,3,2]dioxaborolane-2-yl)-[1,1';4',1'' ]terphenyl-4''-carbonitrile, 0.7 g of tris(dibenzylideneacetone)dipalladium(0), 0.7 g of tricyclohexylphosphine, and 10.5 g of tripotassium phosphate were placed in a reaction vessel, and stirred in a mixed solvent of 1,4-dioxane/H$_2$O under reflux overnight. After allowing to cool, methanol was added to the system for dispersing and washing, and the resulting system was filtered to obtain a crude product. The obtained crude product was purified through recrystallization from 1,2-dichlorobenzene as solvent to thereby obtain 13.1 g (yield: 85%) of a yellow powder of 6-(phenanthrene-9-yl)-2-(4'''-cyano-[1,1'; 4',1'';4'',1''']quaterphenyl-4-yl)-benzoxazole (Compound-136).

Example 27

Synthesis of 2-(4'''-cyano-[1,1';4',1'';4'',1''']quaterphenyl-4-yl)-6-(phenanthrene-9-yl)-4-phenyl-benzoxazole (Compound-137)

First, 10.0 g of 2-(4-chloro-phenyl)-6-(phenanthrene-9-yl)-4-phenyl-benzoxazole, 9.5 g of 4-(4-(4,4,5,5-tetramethyl-[1,3,2]dioxaborolane-2-yl)-[1,1';4',1'' ]terphenyl-4''-carbonitrile, 0.6 g of tris(dibenzylideneacetone)dipalladium (0), 0.6 g of tricyclohexylphosphine, and 8.8 g of tripotassium phosphate were placed in a reaction vessel, and stirred in a mixed solvent of 1,4-dioxane/H$_2$O under reflux overnight. After allowing to cool, methanol was added to the system for dispersing and washing, and the resulting system was filtered to obtain a crude product. The obtained crude product was purified through recrystallization from monochlorobenzene as solvent to thereby obtain 11.9 g (yield: 82%) of a yellow powder of 2-(4'''-cyano-[1,1';4',1'';4'',1''']quaterphenyl-4-yl)-6-(phenanthrene-9-yl)-4-phenyl-benzoxazole (Compound-137).

(Compound-136)

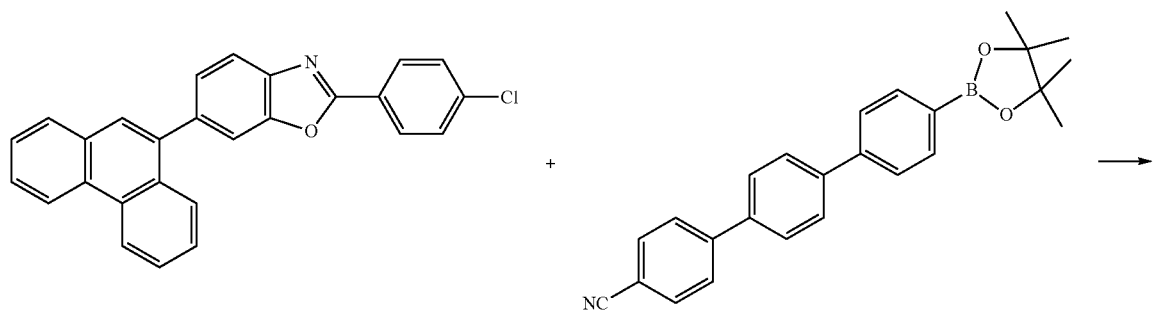

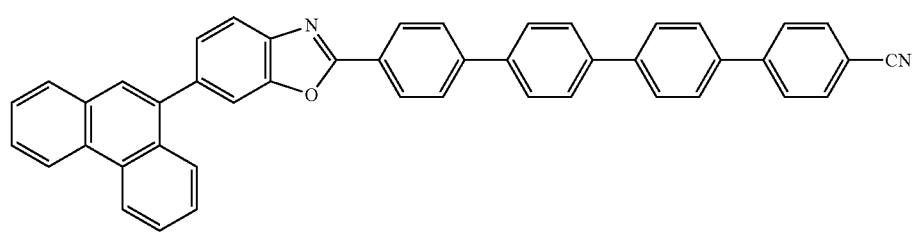

(Compound-137)

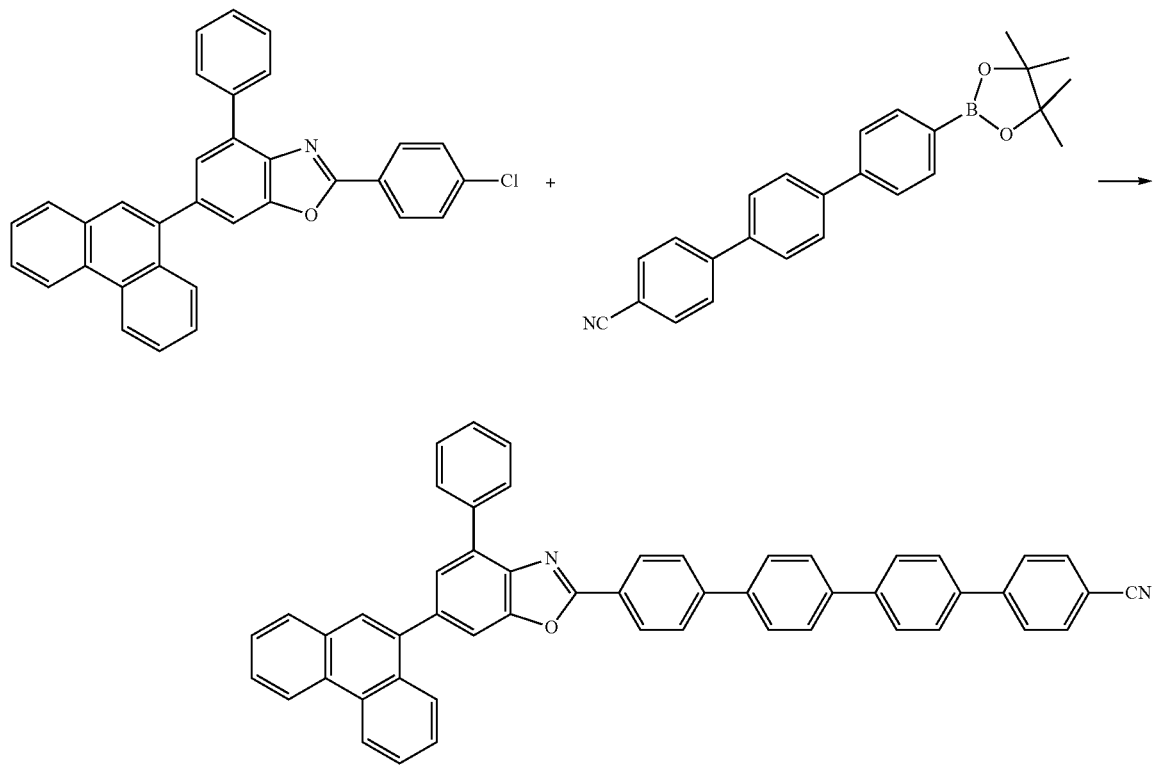

The structure of the obtained yellow powder was identified using NMR.
In ¹H-NMR (CDCl₃), the following signals of 32 hydrogens were detected.
δ (ppm)=8.85 (1H), 8.80 (1H), 8.48 (2H), 8.19 (2H), 8.07 (1H), 7.96 (1H), 7.86 (4H), 7.81 (6H), 7.78 (5H), 7.73 (4H), 7.69 (1H), 7.63 (1H), 7.58 (2H), 7.46 (1H)

Example 28

Synthesis of 2-[4-{4-(4'-cyano-biphenyl-4-yl)-naphthalene-1-yl}-phenyl]-6-(phenanthrene-9-yl)-benzoxazole (Compound-138)

First, 8.0 g of 2-(4-chloro-phenyl)-6-(phenanthrene-9-yl)-benzoxazole, 10.2 g of 4'-{4-(4,4,5,5-tetramethyl-[1,3,2]dioxaborolane-2-yl)-naphthalene-1-yl}1-biphenyl-4-carbonitrile, 0.5 g of tris(dibenzylideneacetone)dipalladium(0), 0.6 g of tricyclohexylphosphine, and 12.6 g of tripotassium phosphate were placed in a reaction vessel, and stirred in a mixed solvent of 1,4-dioxane/H₂O under reflux overnight. After allowing to cool, methanol was added to the system for dispersing and washing, and the resulting system was filtered to obtain a crude product. The obtained crude product was purified through recrystallization from monochlorobenzene as solvent to thereby obtain 11.3 g (yield: 85%) of a yellow powder of 2-[4-{4-(4'-cyano-biphenyl-4-yl)-naphthalene-1-yl}-phenyl]-6-(phenanthrene-9-yl)-benzoxazole (Compound-138).

(Compound-138)

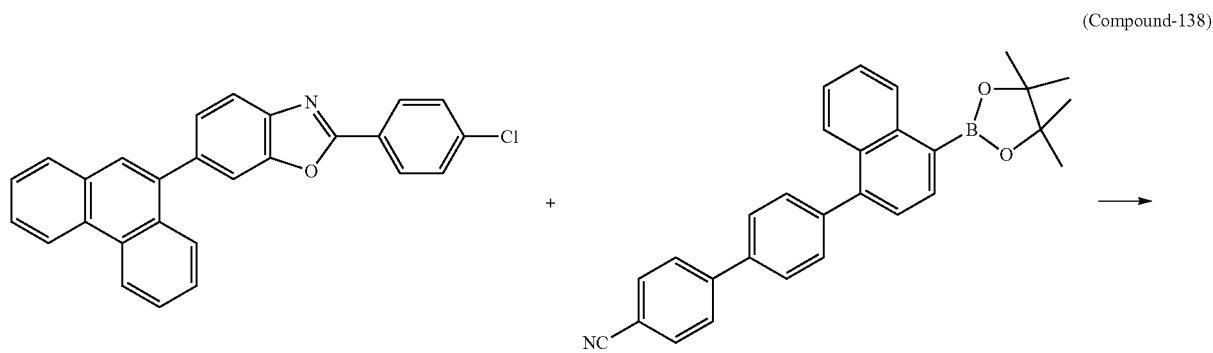

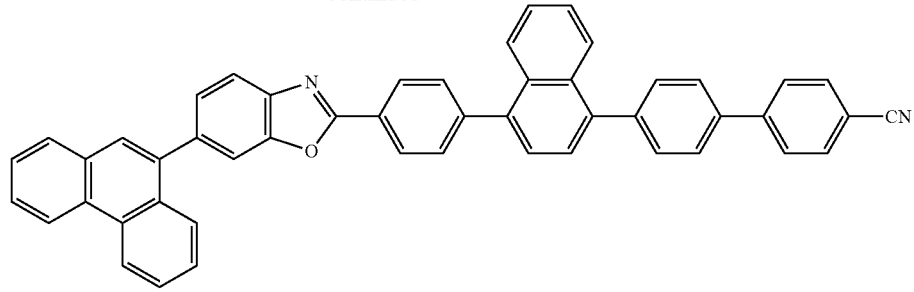

The structure of the obtained yellow powder was identified using NMR.

In ¹H-NMR (CDCl₃), the following signals of 30 hydrogens were detected.

δ (ppm)=8.85 (1H), 8.79 (1H), 8.50 (2H), 8.07 (2H), 8.01 (1H), 7.97 (2H), 7.87-7.75 (10H), 7.72 (4H), 7.67 (1H), 7.62 (2H), 7.59 (2H), 7.55 (2H)

Example 29

Synthesis of 4-(biphenyl-4-yl)-6-(4-cyano-phenyl)-2-([1,1';4',1" ]terphenyl-4-yl)-benzoxazole (Compound-143)

First, 6.0 g of 6-chloro-4-(biphenyl-4-yl)-6-([1,1';4',1" ]terphenyl-4-yl)-benzoxazole, 2.0 g of 4-cyanophenylboronic acid, 0.3 g of tris(dibenzylideneacetone)dipalladium (0), 0.3 g of tricyclohexylphosphine, and 4.8 g of tripotassium phosphate were placed in a reaction vessel, and stirred in a mixed solvent of 1,4-dioxane/H₂O under reflux overnight. After allowing to cool, methanol was added to the system for dispersing and washing, and the resulting system was filtered to obtain a crude product. The obtained crude product was purified through recrystallization from monochlorobenzene as solvent to thereby obtain 3.5 g (yield: 52%) of a pale yellow powder of 4-(biphenyl-4-yl)-6-(4-cyano-phenyl)-2-([1,1';4',1" ]terphenyl-4-yl)-benzoxazole (Compound-143).

(Compound-143)

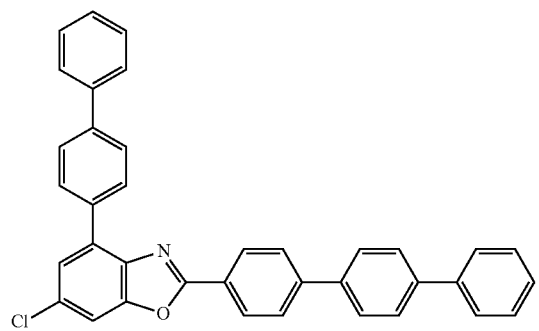

+

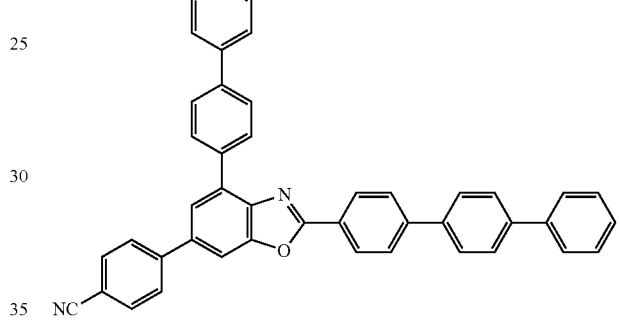

The structure of the obtained pale yellow powder was identified using NMR.

In ¹H-NMR (CDCl₃), the following signals of 28 hydrogens were detected.

δ (ppm)=8.44 (2H), 8.24 (2H), 7.89-7.65 (18H), 7.52 (4H), 7.42 (2H)

Example 30

Synthesis of 6-(4-cyano-phenyl)-4-(phenanthrene-9-yl)-2-{4-(phenanthrene-9-yl)-phenyl}-benzoxazole (Compound-144)

First, 15.7 g of 6-chloro-4-(phenanthrene-9-yl)-2-{4-(phenanthrene-9-yl)-phenyl}-benzoxazole, 4.2 g of 4-cyanophenylboronic acid, 0.7 g of tris(dibenzylideneacetone)dipalladium(0), 0.8 g of tricyclohexylphosphine, and 11.5 g of tripotassium phosphate were placed in a reaction vessel, and stirred in a mixed solvent of 1,4-dioxane/H₂O under reflux overnight. After allowing to cool, water was added to the system for dispersing and washing, and the resulting system was filtered to obtain a crude product. The obtained crude product was purified through recrystallization from monochlorobenzene as solvent to thereby obtain 12.6 g (yield: 72%) of a white powder of 6-(4-cyano-phenyl)-4-(phenanthrene-9-yl)-2-{4-(phenanthrene-9-yl)-phenyl}-benzoxazole (Compound-144).

(Compound-144)

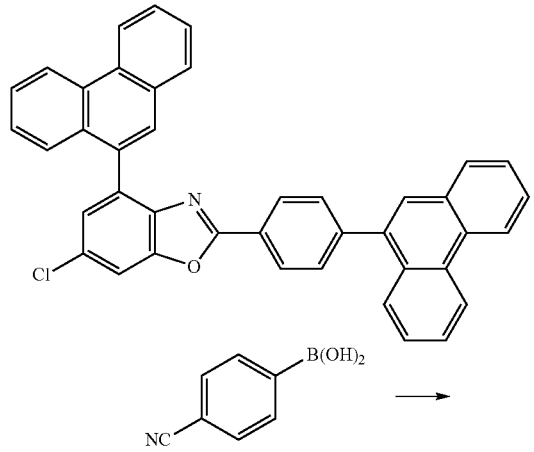

(Compound-147)

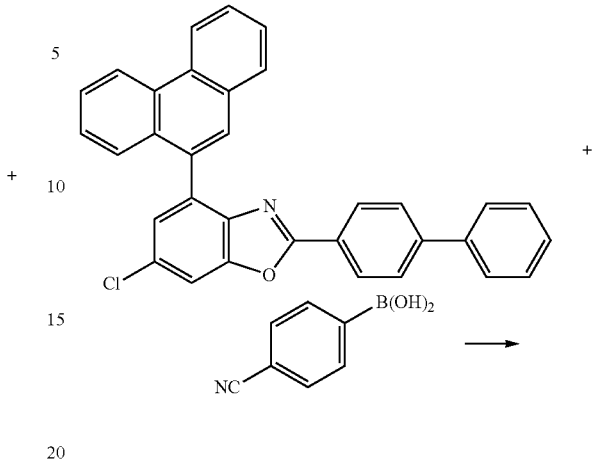

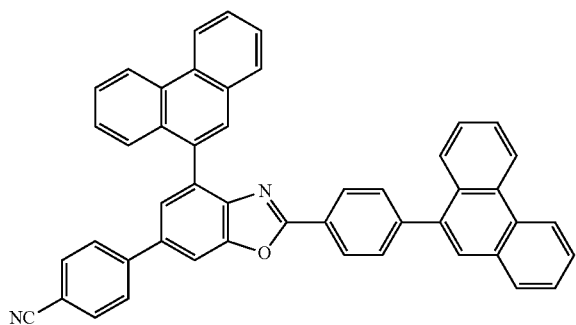

The structure of the obtained white powder was identified using NMR.

In $^1$H-NMR (CDCl$_3$), the following signals of 28 hydrogens were detected.

δ (ppm)=8.87 (1H), 8.81 (2H), 8.75 (1H), 8.37 (2H), 8.00 (1H), 7.99-7.60 (19H), 7.56 (2H)

Example 31

Synthesis of 2-(biphenyl-4-yl)-6-(4-cyano-phenyl)-4-(phenanthrene-9-yl)-benzoxazole (Compound-147)

First, 10.5 g of 2-(biphenyl-4-yl)-6-chloro-4-(phenanthrene-9-yl)-benzoxazole, 3.8 g of 4-cyanophenylboronic acid, 0.6 g of tris(dibenzylideneacetone)dipalladium (0), 0.6 g of tricyclohexylphosphine, and 9.2 g of tripotassium phosphate were placed in a reaction vessel, and stirred in a mixed solvent of 1,4-dioxane/H$_2$O under reflux overnight. After allowing to cool, methanol was added to the system for dispersing and washing, and the resulting system was filtered to obtain a crude product. The obtained crude product was purified through recrystallization from toluene as solvent to thereby obtain 7.2 g (yield: 60%) of a white powder of 2-(biphenyl-4-yl)-6-(4-cyano-phenyl)-4-(phenanthrene-9-yl)-benzoxazole (Compound-147).

The structure of the obtained white powder was identified using NMR.

In $^1$H-NMR (CDCl$_3$), the following signals of 24 hydrogens were detected.

δ (ppm)=8.86 (1H), 8.81 (1H), 8.28 (2H), 7.97 (2H), 7.93 (1H), 7.91-7.61 (13H), 7.54 (1H), 7.49 (2H), 7.41 (1H)

Example 32

Synthesis of 2-(biphenyl-4-yl)-6-(4'-cyano-biphenyl-4-yl)-4-(phenanthrene-9-yl)-benzoxazole (Compound-148)

First, 10.5 g of 2-(biphenyl-4-yl)-6-chloro-4-(phenanthrene-9-yl)-benzoxazole, 8.0 g of 4'-(4,4,5,5-tetramethyl-[1,3,2]dioxaborolane-2-yl)biphenyl-4-carbonitrile, 0.6 g of tris(dibenzylideneacetone)dipalladium(0), 0.6 g of tricyclohexylphosphine, and 9.2 g of tripotassium phosphate were placed in a reaction vessel, and stirred in a mixed solvent of 1,4-dioxane/H$_2$O under reflux overnight. After allowing to cool, methanol was added to the system for dispersing and washing, and the resulting system was filtered to obtain a crude product. The obtained crude product was purified through recrystallization from monochlorobenzene as solvent to thereby obtain 11.4 g (yield: 84%) of a white powder of 2-(biphenyl-4-yl)-6-(4'-cyano-biphenyl-4-yl)-4-(phenanthrene-9-yl)-benzoxazole (Compound-148).

(Compound-148)

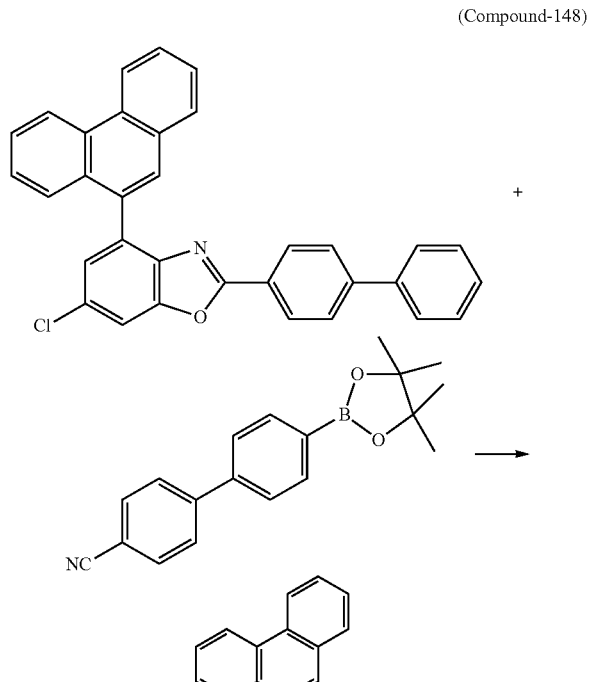

The structure of the obtained white powder was identified using NMR.

In $^1$H-NMR (CDCl$_3$), the following signals of 28 hydrogens were detected.

δ (ppm)=8.87 (1H), 8.82 (1H), 8.30 (2H), 8.00 (3H), 7.94 (1H), 7.88 (2H), 7.84 (1H), 7.78 (4H), 7.77-7.63 (9H), 7.55 (1H), 7.49 (2H), 7.41 (1H)

Example 33

Synthesis of 6-(4'-cyano-biphenyl-4-yl)-2-{4-(phenanthrene-9-yl)-phenyl}-4-phenyl-benzoxazole (Compound-149)

First, 13.0 g of 2-(4-chloro-phenyl)-6-(4'-cyano-biphenyl-4-yl)-4-phenyl-benzoxazole, 6.0 g of 9-phenanthreneboronic acid, 0.7 g of tris(dibenzylideneacetone)dipalladium (0), 0.8 g of tricyclohexylphosphine, and 11.4 g of tripotassium phosphate were placed in a reaction vessel, and stirred in a mixed solvent of 1,4-dioxane/H$_2$O under reflux overnight. After allowing to cool, methanol was added to the system for dispersing and washing, and the resulting system was filtered to obtain a crude product. The obtained crude product was purified through recrystallization from monochlorobenzene as solvent to thereby obtain 12.0 g (yield: 71%) of a white powder of 6-(4'-cyano-biphenyl-4-yl)-2-{4-(phenanthrene-9-yl)-phenyl}-4-phenyl-benzoxazole (Compound-149).

(Compound-149)

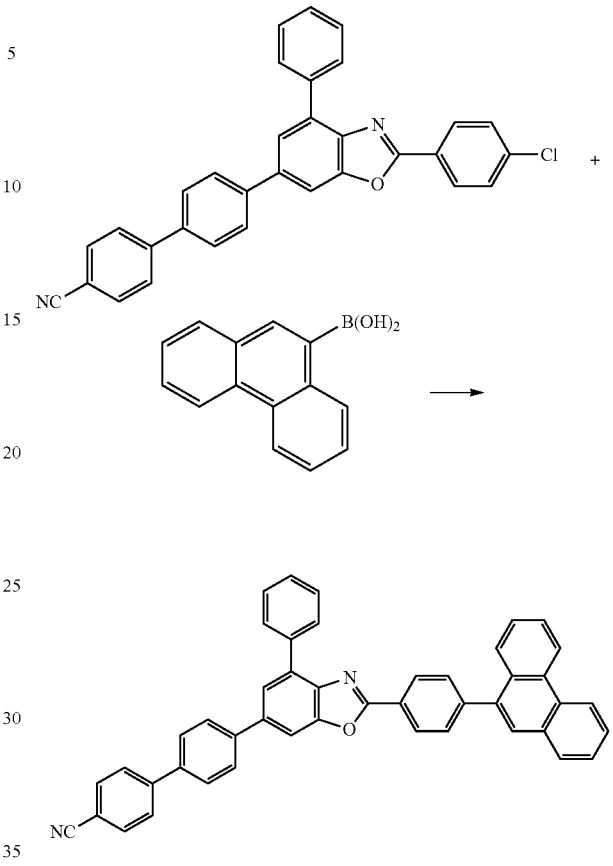

The structure of the obtained white powder was identified using NMR.

In $^1$H-NMR (CDCl$_3$), the following signals of 28 hydrogens were detected.

δ (ppm)=8.82 (1H), 8.78 (1H), 8.50 (2H), 8.18 (2H), 7.98 (1H), 7.95 (1H), 7.88 (4H), 7.81-7.71 (11H), 7.68 (1H), 7.64 (1H), 7.60 (2H), 7.50 (1H)

Example 34

Synthesis of 6-(4'-cyano-biphenyl-4-yl)-2-{4-(9,9'-spirobi[9H]fluorene-4-yl)-phenyl}-benzoxazole (Compound-150)

First, 11.3 g of 2-(4-chloro-phenyl)-6-(4'-cyano-biphenyl-4-yl)-benzoxazole, 11.0 g of 9,9'-spirobi[9H]fluorene-4-yl-boronic acid, 0.8 g of tris(dibenzylideneacetone)dipalladium (0), 0.8 g of tricyclohexylphosphine, and 11.8 g of tripotassium phosphate were placed in a reaction vessel, and stirred in a mixed solvent of 1,4-dioxane/H$_2$O under reflux overnight. After allowing to cool, methanol was added to the system for dispersing and washing, and the resulting system was filtered to obtain a crude product. The obtained crude product was purified through recrystallization from monochlorobenzene as solvent to thereby obtain 12.6 g (yield: 66%) of a pale yellow powder of 6-(4'-cyano-biphenyl-4-yl)-2-{4-(9,9'-spirobi[9H]fluorene-4-yl)-phenyl}-benzoxazole (Compound-150).

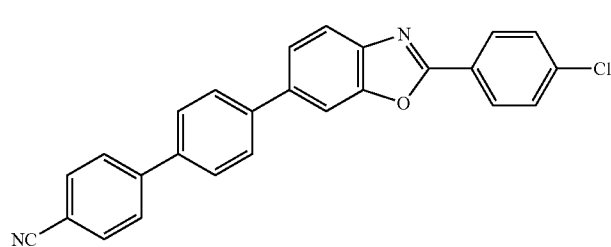
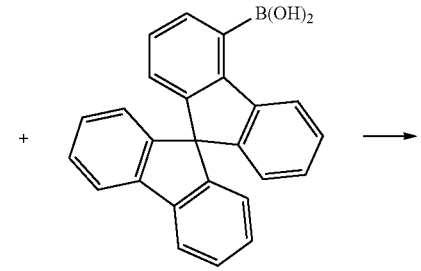

(Compound-150)

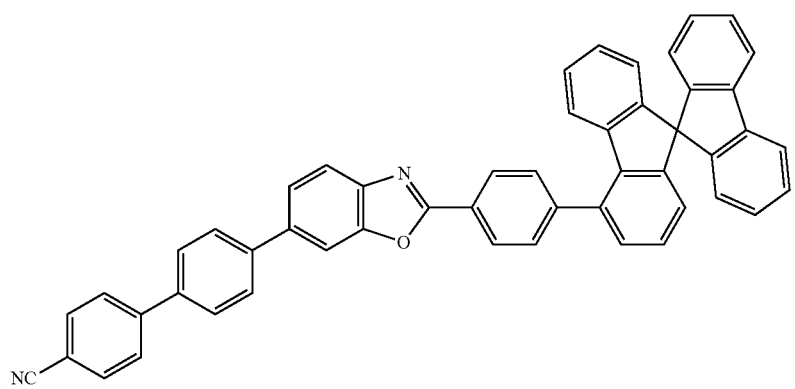

The structure of the obtained pale yellow powder was identified using NMR.

In ¹H-NMR (CDCl₃), the following signals of 30 hydrogens were detected.

δ (ppm)=8.51 (2H), 7.94 (1H), 7.92 (1H), 7.91 (1H), 7.88 (2H), 7.84 (3H), 7.80 (2H), 7.79 (3H), 7.75 (1H), 7.73 (1H), 7.42 (2H), 7.27 (1H), 7.22-7.14 (4H), 7.07 (2H), 6.85 (2H), 6.79 (1H), 6.74 (1H)

Example 35

Synthesis of 6-(4'-cyano-biphenyl-4-yl)-4-phenyl-2-{4-(9,9'-spirobi[9H]fluorene-4-yl)-phenyl}-benzoxazole (Compound-151)

First, 12.1 g of 2-(4-chloro-phenyl)-6-(4'-cyano-biphenyl-4-yl)-4-phenyl-benzoxazole, 6.0 g of 9,9'-spirobi[9H]fluorene-4-yl-boronic acid, 0.7 g of tris(dibenzylideneacetone)dipalladium(0), 0.7 g of tricyclohexylphosphine, and 10.6 g of tripotassium phosphate were placed in a reaction vessel, and stirred in a mixed solvent of 1,4-dioxane/H₂O under reflux overnight. After allowing to cool, methanol was added to the system for dispersing and washing, and the resulting system was filtered to obtain a crude product. The obtained crude product was purified through recrystallization from monochlorobenzene as solvent to thereby obtain 8.2 g (yield: 43%) of a pale yellow powder of 6-(4'-cyano-biphenyl-4-yl)-4-phenyl-2-{4-(9,9'-spirobi[9H]fluorene-4-yl)-phenyl}-benzoxazole (Compound-151).

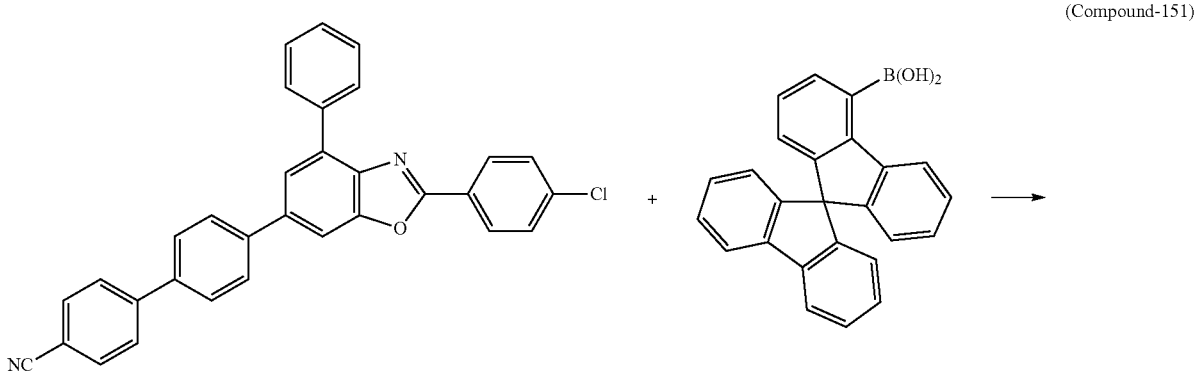

(Compound-151)

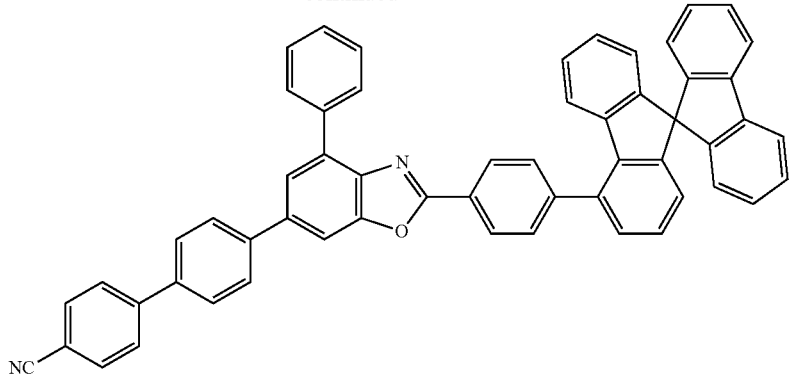

The structure of the obtained pale yellow powder was identified using NMR.

In $^1$H-NMR (CDCl$_3$), the following signals of 34 hydrogens were detected.

δ (ppm)=8.55 (2H), 8.19 (2H), 7.94-7.85 (7H), 7.85-7.74 (6H), 7.63 (2H), 7.51 (1H), 7.42 (2H), 7.27 (1H), 7.28 (1H), 7.18 (4H), 7.07 (2H), 6.86 (2H), 6.79 (1H), 6.75 (1H)

Example 36

Synthesis of 2-(biphenyl-4-yl)-6-{4-(4-cyano-phenyl)-naphthalene-1-yl}-4-phenyl-benzoxazole (Compound-154)

First, 13.2 g of 2-(biphenyl-4-yl)-6-bromo-4-phenyl-benzoxazole, 11.5 g of 4-{4-(4,4,5,5-tetramethyl-[1,3,2]dioxaborolane-2-yl)-naphthalene-1-yl}-phenyl-carbonitrile, 0.7 g of tetrakis(triphenylphosphine)dipalladium (0), and 7.3 g of potassium carbonate were placed in a reaction vessel, and stirred in a mixed solvent of toluene/ethanol/H$_2$O under reflux overnight. After allowing to cool, methanol was added to the system for dispersing and washing, and the resulting system was filtered to obtain a crude product. The obtained crude product was purified through crystallization from a mixed solvent of tetrahydrofuran/acetone to thereby obtain 15.8 g (yield: 89%) of a white powder of 2-(biphenyl-4-yl)-6-{4-(4-cyano-phenyl)-naphthalene-1-yl}-4-phenyl-benzoxazole (Compound-154).

(Compound-154)

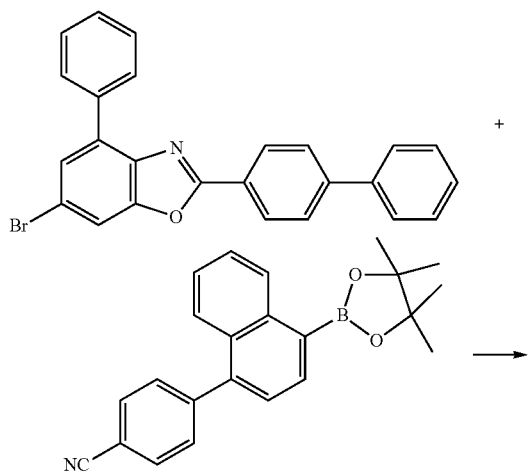

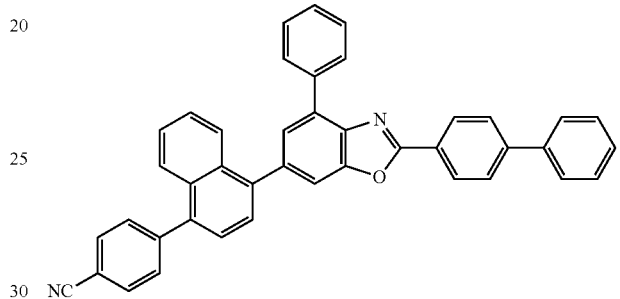

The structure of the obtained white powder was identified using NMR.

In $^1$H-NMR (CDCl$_3$), the following signals of 26 hydrogens were detected.

δ (ppm)=8.46 (2H), 8.18 (2H), 8.14 (1H), 7.91 (1H), 7.86 (2H), 7.81 (2H), 7.76 (2H), 7.72 (4H), 7.65 (1H), 7.62-7.40 (9H)

Example 37

Synthesis of 6-[4-{4-(4'-cyano-biphenyl-4-yl)-naphthalene-1-yl}-phenyl]-2,4-diphenyl-benzoxazole (Compound-155)

First, 4.0 g of 6-chloro-2,4-diphenyl-benzoxazole, 5.9 g of 4'-{4-(4,4,5,5-tetramethyl-[1,3,2]dioxaborolane-2-yl)-naphthalene-1-yl}-biphenyl-4-carbonitrile, 0.4 g of tris(dibenzylideneacetone)dipalladium(0), 0.4 g of tricyclohexylphosphine, and 5.6 g of tripotassium phosphate were placed in a reaction vessel, and stirred in a mixed solvent of 1,4-dioxane/H$_2$O under reflux overnight. After allowing to cool, methanol was added to the system for dispersing and washing, and the resulting system was filtered to obtain a crude product. The obtained crude product was purified through recrystallization from monochlorobenzene as solvent to thereby obtain 3.2 g (yield: 43%) of a white powder of 6-[4-{4-(4'-cyano-biphenyl-4-yl)-naphthalene-1-yl}-phenyl]-2,4-diphenyl-benzoxazole (Compound-155).

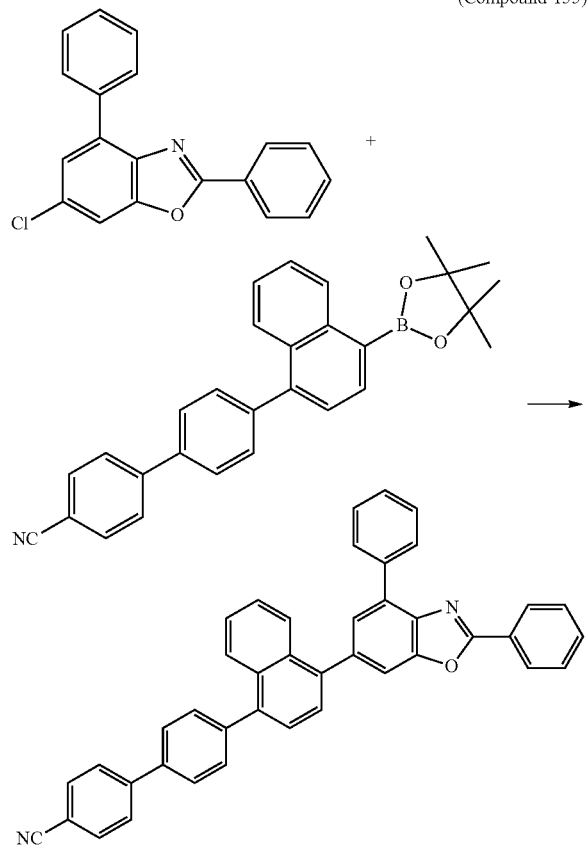

(Compound-155)

The structure of the obtained white powder was identified using NMR.

In $^1$H-NMR (CDCl$_3$), the following signals of 26 hydrogens were detected.

δ (ppm)=8.40 (1H), 8.38 (1H), 8.17 (2H), 8.13 (1H), 8.07 (1H), 7.83 (5H), 7.77 (3H), 7.72 (2H), 7.67-7.51 (9H), 7.47 (1H)

Example 38

Synthesis of 2-(biphenyl-4-yl)-6-(4"-cyano-[1,1';4',1"]terphenyl-4-yl)-4-phenyl-benzoxazole (Compound-156)

First, 13.2 g of 2-(biphenyl-4-yl)-6-bromo-4-phenyl-benzoxazole, 12.4 g of 4-(4-(4,4,5,5-tetramethyl-[1,3,2]dioxaborolane-2-yl)-[1,1';4',1"]terphenyl-4"-carbonitrile, 0.7 g of tetrakis(triphenylphosphine)dipalladium (0), and 7.3 g of potassium carbonate were placed in a reaction vessel, and stirred in a mixed solvent of toluene/ethanol/H$_2$O under refluxed overnight. After allowing to cool, methanol was added to the system for dispersing and washing, and the resulting system was filtered to obtain a crude product. The obtained crude product was purified through recrystallization from monochlorobenzene as solvent to thereby obtain 7.2 g (yield: 39%) of a white powder of 2-(biphenyl-4-yl)-6-(4"-cyano-[1,1';4',1"]terphenyl-4-yl)-4-phenyl-benzoxazole (Compound-156).

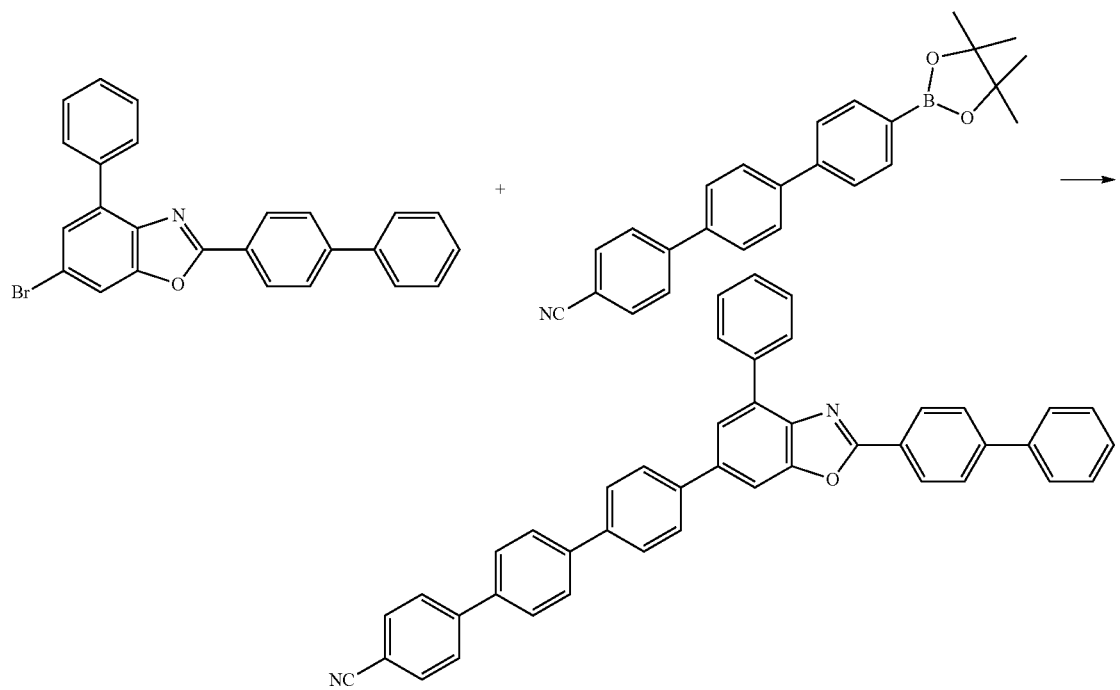

(Compound-156)

The structure of the obtained white powder was identified using NMR.

In $^1$H-NMR (CDCl$_3$), the following signals of 28 hydrogens were detected.

δ (ppm)=8.42 (2H), 8.16 (2H), 7.86 (3H), 7.84 (2H), 7.81 (4H), 7.78 (5H), 7.74 (2H), 7.71 (2H), 7.60 (2H), 7.52 (2H), 7.49 (1H), 7.45 (1H)

Example 39

Synthesis of 2-{4-(phenanthrene-9-yl)-phenyl}-6-(4"-cyano-[1,1';4',1"]terphenyl-4-yl)-4-phenyl-benzoxazole (Compound-157)

First, 12.8 g of 2-(4-chloro-phenyl)-6-(4"-cyano-[1,1';4',1"]terphenyl-4-yl)-4-phenyl-benzoxazole, 5.3 g of 9-phenanthreneboronic acid, 0.6 g of tris(dibenzylideneacetone)dipalladium(0), 0.6 g of tricyclohexylphosphine, and 9.7 g of tripotassium phosphate were placed in a reaction vessel, and stirred in a mixed solvent of 1,4-dioxane/H$_2$O under reflux overnight. After allowing to cool, methanol was added to the system for dispersing and washing, and the resulting system was filtered to obtain a crude product. The obtained crude product was purified through recrystallization from monochlorobenzene as solvent to thereby obtain 5.3 g (yield: 33%) of a white powder of 2-{4-(phenanthrene-9-yl)-phenyl}-6-(4"-cyano-[1,1';4',1"]terphenyl-4-yl)-4-phenyl-benzoxazole (Compound-157).

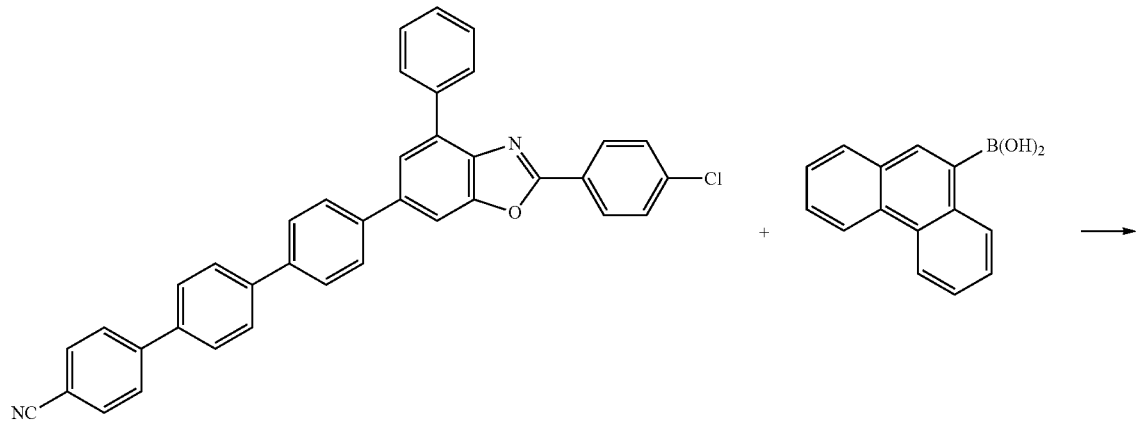

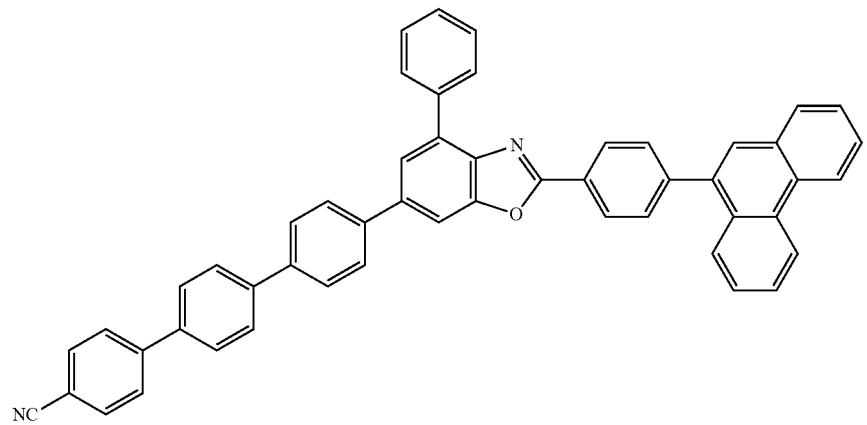

(Compound-157)

The structure of the obtained white powder was identified using NMR.

In ¹H-NMR (CDCl₃), the following signals of 32 hydrogens were detected.

δ (ppm)=8.84 (1H), 8.78 (1H), 8.50 (2H), 8.19 (2H), 7.97 (2H), 7.91-7.66 (20H), 7.61 (3H), 7.49 (1H)

Example 40

Synthesis of 2-(biphenyl-4-yl)-6-(3"-cyano-[1,1';4',1"]terphenyl-4-yl)-4-phenyl-benzoxazole (Compound-158)

First, 11.0 g of 2-(biphenyl-4-yl)-6-chloro-4-phenyl-benzoxazole, 11.5 g of 4-(4-(4,4,5,5-tetramethyl-[1,3,2]dioxaborolane-2-yl)-[1,1';4',1"]terphenyl-3"-carbonitrile, 0.8 g of tris(dibenzylideneacetone)dipalladium(0), 0.8 g of tricyclohexylphosphine, and 12.2 g of tripotassium phosphate were placed in a reaction vessel, and stirred in a mixed solvent of 1,4-dioxane/H₂O under reflux overnight. After allowing to cool, methanol was added to the system for dispersing and washing, and the resulting system was filtered to obtain a crude product. The obtained crude product was purified through recrystallization from 1,2-dichlorobenzene as solvent to thereby obtain 15.4 g (yield: 89%) of a pale yellow powder of 2-(biphenyl-4-yl)-6-(3"-cyano-[1,1';4',1"]terphenyl-4-yl)-4-phenyl-benzoxazole (Compound-158).

The structure of the obtained pale yellow powder was identified using NMR.

In ¹H-NMR (CDCl₃), the following signals of 28 hydrogens were detected.

δ (ppm)=8.42 (2H), 8.17 (2H), 7.96 (1H), 7.90 (1H), 7.88-7.76 (10H), 7.74-7.66 (5H), 7.60 (3H), 7.54 (2H), 7.45 (2H)

Example 41

Synthesis of 2-(biphenyl-4-yl)-6-{4-(4'-cyano-biphenyl-4-yl)-naphthalene-1-yl}-4-phenyl-benzoxazole (Compound-159)

First, 13.2 g of 2-(biphenyl-4-yl)-6-bromo-4-phenyl-benzoxazole, 14.0 g of 4'-{4-(4,4,5,5-tetramethyl-[1,3,2]dioxaborolane-2-yl)-naphthalene-1-yl}-biphenyl-4-carbonitrile, 0.7 g of tetrakis(triphenylphosphine)dipalladium (0), and 7.3 g of potassium carbonate were placed in a reaction vessel, and stirred in a mixed solvent of toluene/ethanol/H₂O under reflux overnight. After allowing to cool, methanol was added to the system for dispersing and washing, and the resulting system was filtered to obtain a crude product. The obtained crude product was purified through crystallization from a mixed solvent of tetrahydrofuran/acetone to thereby obtain 13.0 g (yield: 65%) of a white powder of 2-(biphenyl-4-yl)-6-{4-(4'-cyano-biphenyl-4-yl)-naphthalene-1-yl}-4-phenyl-benzoxazole (Compound-159).

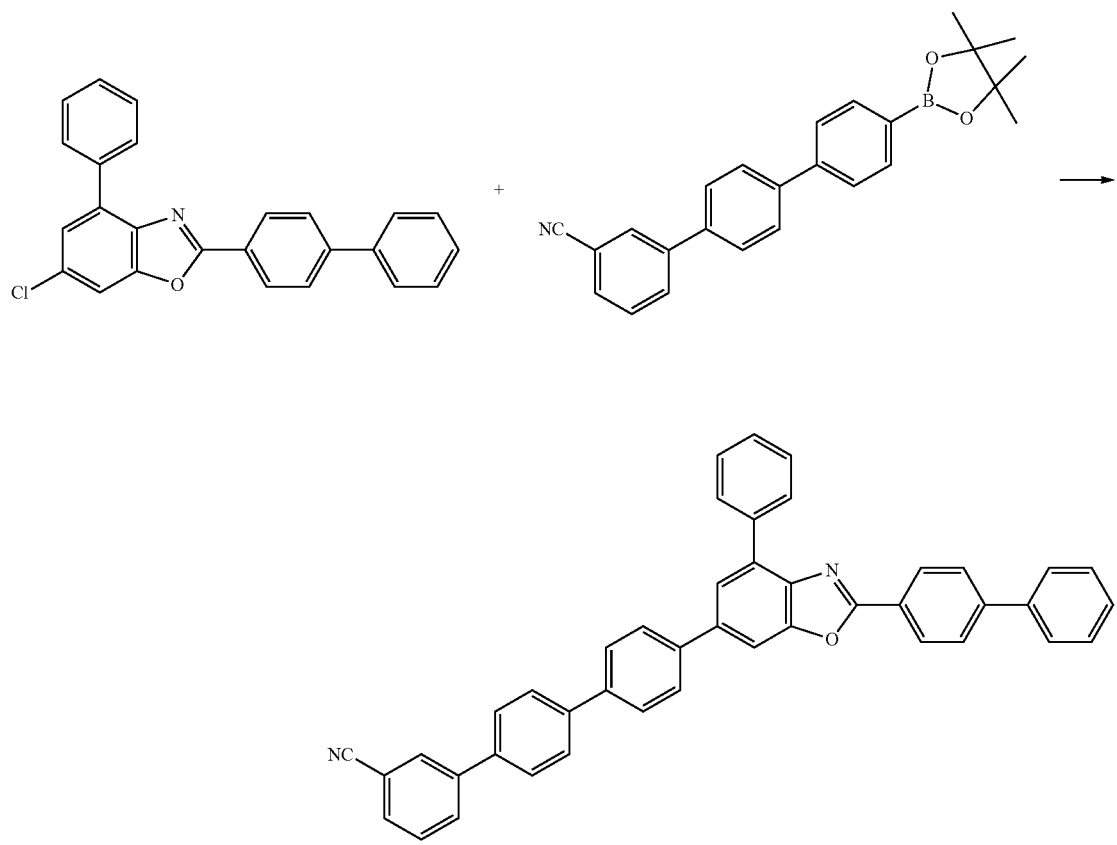

(Compound-158)

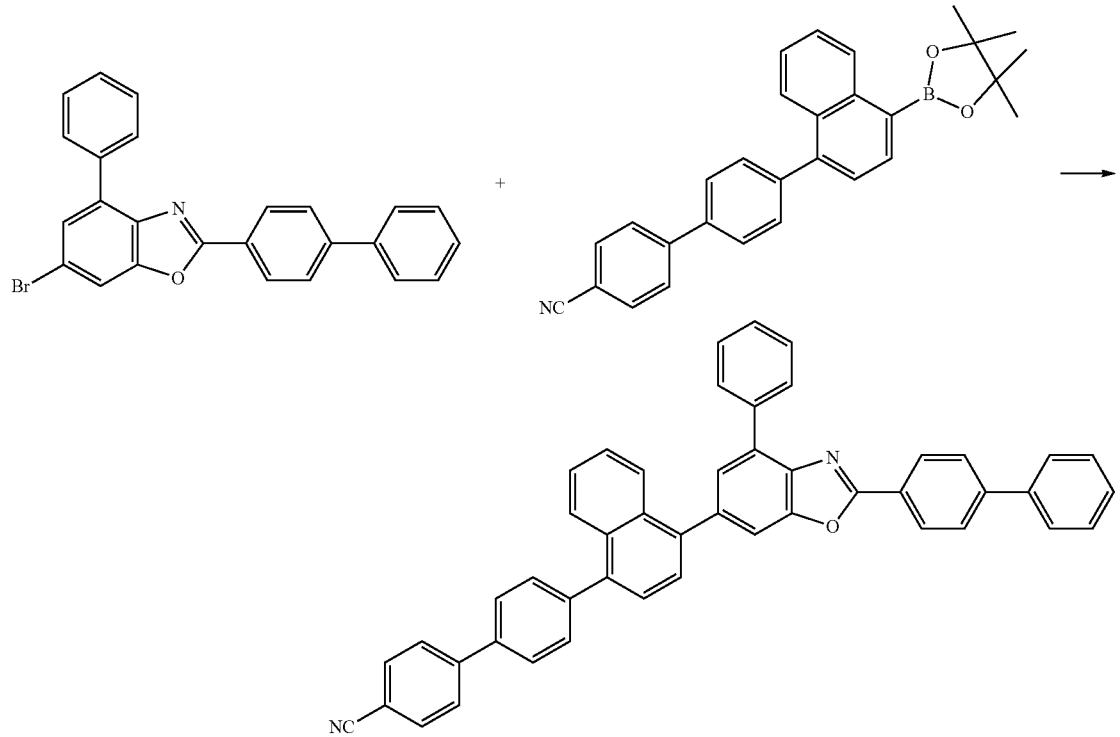
(Compound-159)

The structure of the obtained white powder was identified using NMR.

In $^1$H-NMR (CDCl$_3$), the following signals of 30 hydrogens were detected.

δ (ppm)=8.46 (2H), 8.19 (2H), 8.15 (1H), 8.08 (1H), 7.87-7.77 (10H), 7.72 (4H), 7.66 (1H), 7.62-7.41 (9H)

Example 42

Synthesis of 2-(biphenyl-4-yl)-6-{2-(4'-cyano-biphenyl-4-yl)-naphthalene-6-yl}-4-phenyl-benzoxazole (Compound-160)

First, 13.2 g of 2-(biphenyl-4-yl)-6-chloro-4-phenyl-benzoxazole, 15.7 g of 4'-{2-(4,4,5,5-tetramethyl-[1,3,2]dioxaborolane-2-yl)-naphthalene-6-yl}-biphenyl-4-carbonitrile, 0.9 g of tris(dibenzylideneacetone)dipalladium(0), 1.0 g of tricyclohexylphosphine, and 14.7 g of tripotassium phosphate were placed in a reaction vessel, and stirred in a mixed solvent of 1,4-dioxane/H$_2$O under reflux overnight. After allowing to cool, methanol was added to the system for dispersing and washing, and the resulting system was filtered to obtain a crude product. The obtained crude product was purified through recrystallization from 1,2-dichlorobenzene as solvent to thereby obtain 17.0 g (yield: 72%) of a pale yellow powder of 2-(biphenyl-4-yl)-6-{2-(4'-cyano-biphenyl-4-yl)-naphthalene-6-yl}-4-phenyl-benzoxazole (Compound-160).

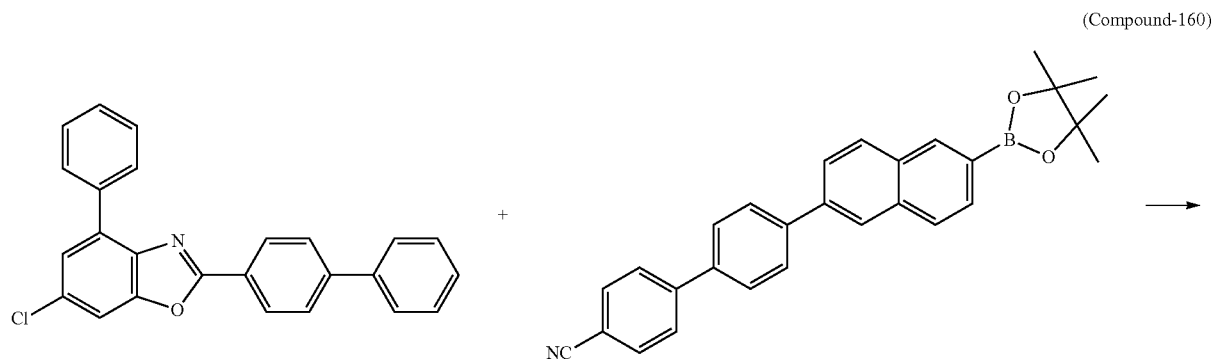
(Compound-160)

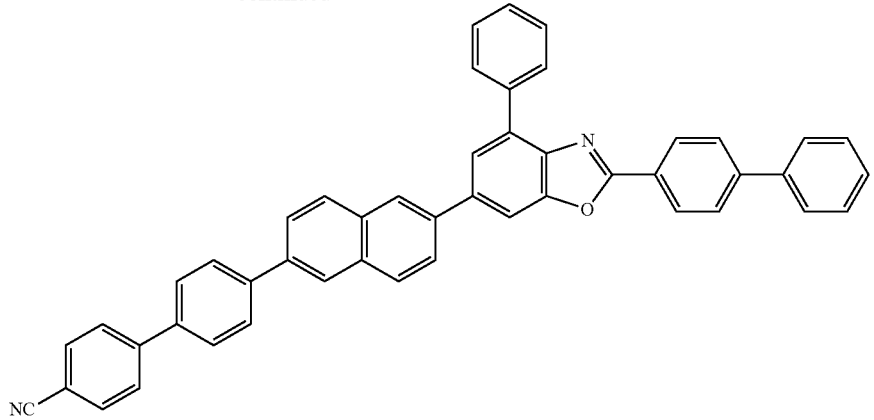

The structure of the obtained pale yellow powder was identified using NMR.

In $^1$H-NMR (CDCl$_3$), the following signals of 30 hydrogens were detected.

δ (ppm)=8.43 (2H), 8.22 (2H), 8.18 (2H), 8.08 (2H), 7.97 (2H), 7.93 (3H), 7.88 (1H), 7.85-7.77 (7H), 7.75 (2H), 7.70 (1H), 7.61 (2H), 7.52 (3H), 7.45 (1H)

Example 43

Synthesis of 2-(biphenyl-4-yl)-6-{2-(4'-cyano-biphenyl-4-yl)-naphthalene-7-yl}-4-phenyl-benzoxazole (Compound-161)

First, 13.2 g of 2-(biphenyl-4-yl)-6-chloro-4-phenyl-benzoxazole, 15.7 g of 4'-{2-(4,4,5,5-tetramethyl-[1,3,2]dioxaborolane-2-yl)-naphthalene-7-yl}-biphenyl-4-carbonitrile, 0.9 g of tris(dibenzylideneacetone)dipalladium(0), 1.0 g of tricyclohexylphosphine, and 14.7 g of tripotassium phosphate were placed in a reaction vessel, and stirred in a mixed solvent of 1,4-dioxane/H$_2$O under reflux overnight. After allowing to cool, methanol was added to the system for dispersing and washing, and the resulting system was filtered to obtain a crude product. The obtained crude product was purified through recrystallization from 1,2-dichlorobenzene as solvent to thereby obtain 17.3 g (yield: 77%) of a pale yellow powder of 2-(biphenyl-4-yl)-6-{2-(4'-cyano-biphenyl-4-yl)-naphthalene-7-yl}-4-phenyl-benzoxazole (Compound-161).

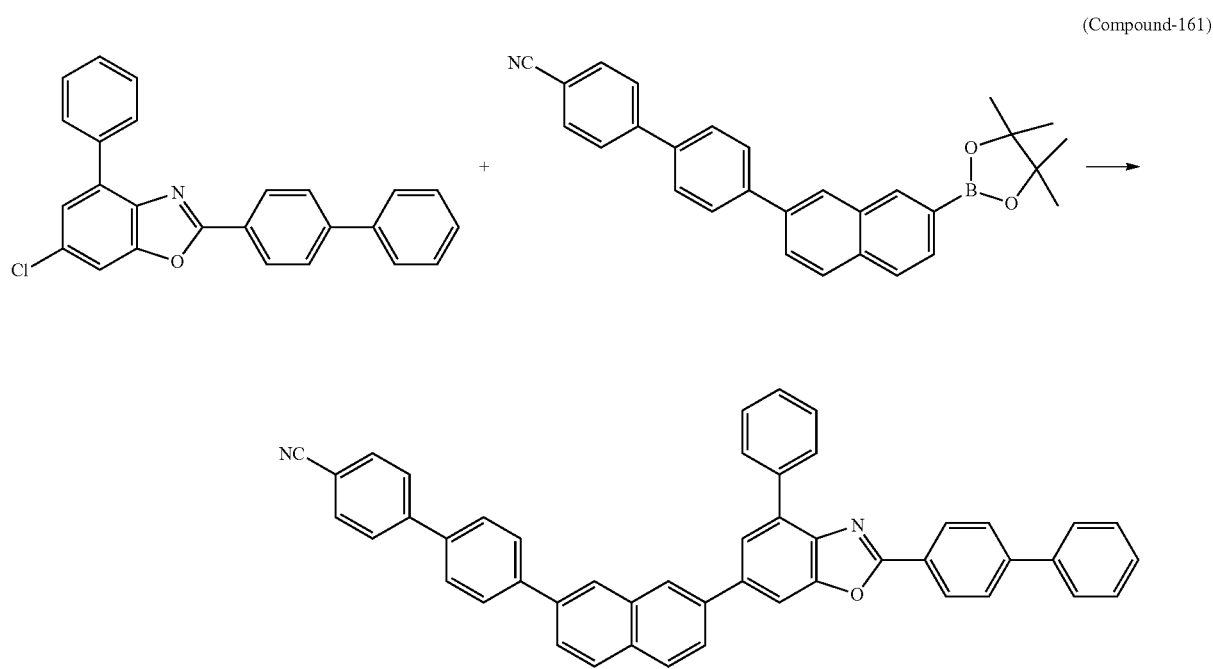

(Compound-161)

The structure of the obtained pale yellow powder was identified using NMR.

In $^1$H-NMR (CDCl$_3$), the following signals of 30 hydrogens were detected.

δ (ppm)=8.42 (2H), 8.23 (2H), 8.19 (2H), 8.03 (2H), 7.94 (2H), 7.92 (3H), 7.84 (2H), 7.82-7.76 (6H), 7.73 (2H), 7.70 (1H), 7.61 (2H), 7.52 (2H), 7.51 (1H), 7.45 (1H)

Example 44

Synthesis of 2-(biphenyl-4-yl)-4-(4-cyano-phenyl)-6-(phenanthrene-9-yl)-benzoxazole (Compound-164)

First, 9.4 g of 2-(4-chloro-phenyl)-4-(4-cyano-phenyl)-6-(phenanthrene-9-yl)-benzoxazole, 2.4 g of phenylboronic acid, 0.5 g of tris(dibenzylideneacetone)dipalladium(0), 0.5 g of tricyclohexylphosphine, and 7.9 g of tripotassium phosphate were placed in a reaction vessel, and stirred in a mixed solvent of 1,4-dioxane/H$_2$O under reflux overnight. After allowing to cool, methanol was added to the system for dispersing and washing, and the resulting system was filtered to obtain a crude product. The obtained crude product was purified through crystallization from a mixed solvent of toluene/acetone to thereby obtain 5.3 g (yield: 51%) of a white powder of 2-(biphenyl-4-yl)-4-(4-cyano-phenyl)-6-(phenanthrene-9-yl)-benzoxazole (Compound-164).

In $^1$H-NMR (CDCl$_3$), the following signals of 24 hydrogens were detected.

δ (ppm)=8.86 (1H), 8.80 (1H), 8.45 (2H), 8.33 (2H), 8.01 (1H), 7.96 (1H), 7.90-7.65 (12H), 7.61 (1H), 7.54 (2H), 7.46 (1H)

Example 45

Synthesis of 2-(biphenyl-4-yl)-4-(3-cyano-phenyl)-6-(phenanthrene-9-yl)-benzoxazole (Compound-165)

First, 9.1 g of 2-(biphenyl-4-yl)-6-chloro-4-(3-cyano-phenyl)-benzoxazole, 6.0 g of 9-phenanthreneboronic acid, 0.6 g of tris(dibenzylideneacetone)dipalladium(0), 0.6 g of tricyclohexylphosphine, and 9.5 g of tripotassium phosphate were placed in a reaction vessel, and stirred in a mixed solvent of 1,4-dioxane/H$_2$O under reflux overnight. After allowing to cool, methanol was added to the system for dispersing and washing, and the resulting system was filtered to obtain a crude product. The obtained crude product was purified through recrystallization from monochlorobenzene as solvent to thereby obtain 10.4 g (yield: 85%) of a white powder of 2-(biphenyl-4-yl)-4-(3-cyano-phenyl)-6-(phenanthrene-9-yl)-benzoxazole (Compound-165).

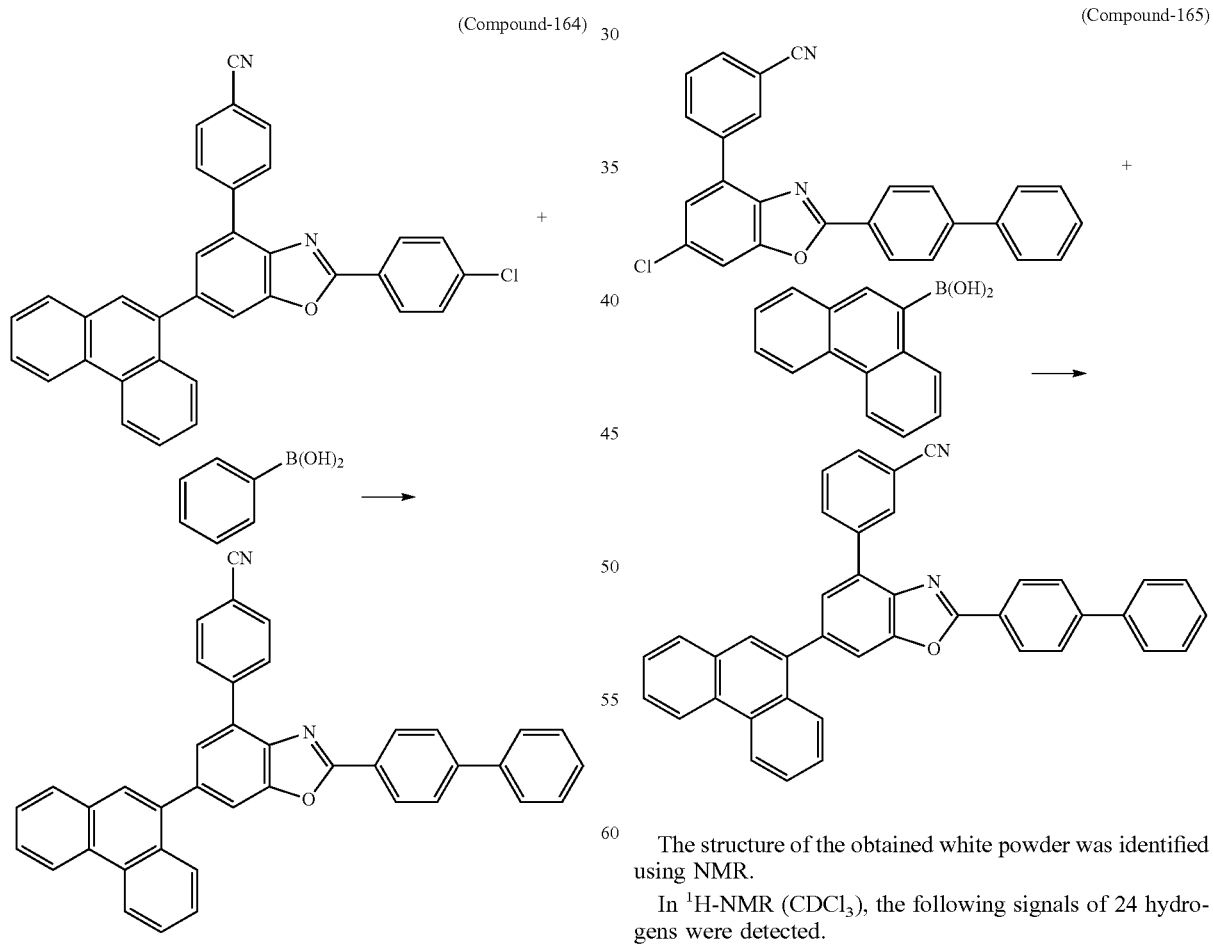

The structure of the obtained white powder was identified using NMR.

In $^1$H-NMR (CDCl$_3$), the following signals of 24 hydrogens were detected.

δ (ppm)=8.86 (1H), 8.79 (1H), 8.59 (1H), 8.45 (2H), 8.38 (1H), 8.02 (1H), 7.97 (1H), 7.84 (2H), 7.83 (2H), 7.79-7.53 (9H), 7.54 (2H), 7.45 (1H)

Example 46

Synthesis of 2-(biphenyl-4-yl)-4-(4-cyano-phenyl)-6-{4-(phenanthrene-9-yl)-phenyl}-benzoxazole (Compound-166)

First, 9.0 g of 2-(biphenyl-4-yl)-6-chloro-4-(4-cyano-phenyl)-benzoxazole, 7.9 g of 4-(phenanthrene-9-yl)phenylboronic acid, 0.6 g of tris(dibenzylideneacetone)dipalladium (0), 0.6 g of tricyclohexylphosphine, and 9.4 g of tripotassium phosphate were placed in a reaction vessel, and stirred in a mixed solvent of 1,4-dioxane/H$_2$O under reflux overnight. After allowing to cool, methanol was added to the system for dispersing and washing, and the resulting system was filtered to obtain a crude product. The obtained crude product was purified through recrystallization from monochlorobenzene as solvent to thereby obtain 11.7 g (yield: 85%) of a white powder of 2-(biphenyl-4-yl)-4-(4-cyano-phenyl)-6-{4-(phenanthrene-9-yl)-phenyl}-benzoxazole (Compound-166).

Example 47

Synthesis of 2-(biphenyl-4-yl)-4-(3-cyano-phenyl)-6-{4-(phenanthrene-9-yl)-phenyl}-benzoxazole (Compound-167)

First, 9.1 g of 2-(biphenyl-4-yl)-6-chloro-4-(3-cyano-phenyl)-benzoxazole, 8.0 g of 4-(phenanthrene-9-yl)phenylboronic acid, 0.6 g of tris(dibenzylideneacetone)dipalladium (0), 0.6 g of tricyclohexylphosphine, and 9.5 g of tripotassium phosphate were placed in a reaction vessel, and stirred in a mixed solvent of 1,4-dioxane/H$_2$O under reflux overnight. After allowing to cool, methanol was added to the system for dispersing and washing, and the resulting system was filtered to obtain a crude product. The obtained crude product was purified through recrystallization from monochlorobenzene solvent to thereby obtain 11.9 g (yield: 85%) of a white powder of 2-(biphenyl-4-yl)-4-(3-cyano-phenyl)-6-{4-(phenanthrene-9-yl)-phenyl}-benzoxazole (Compound-167).

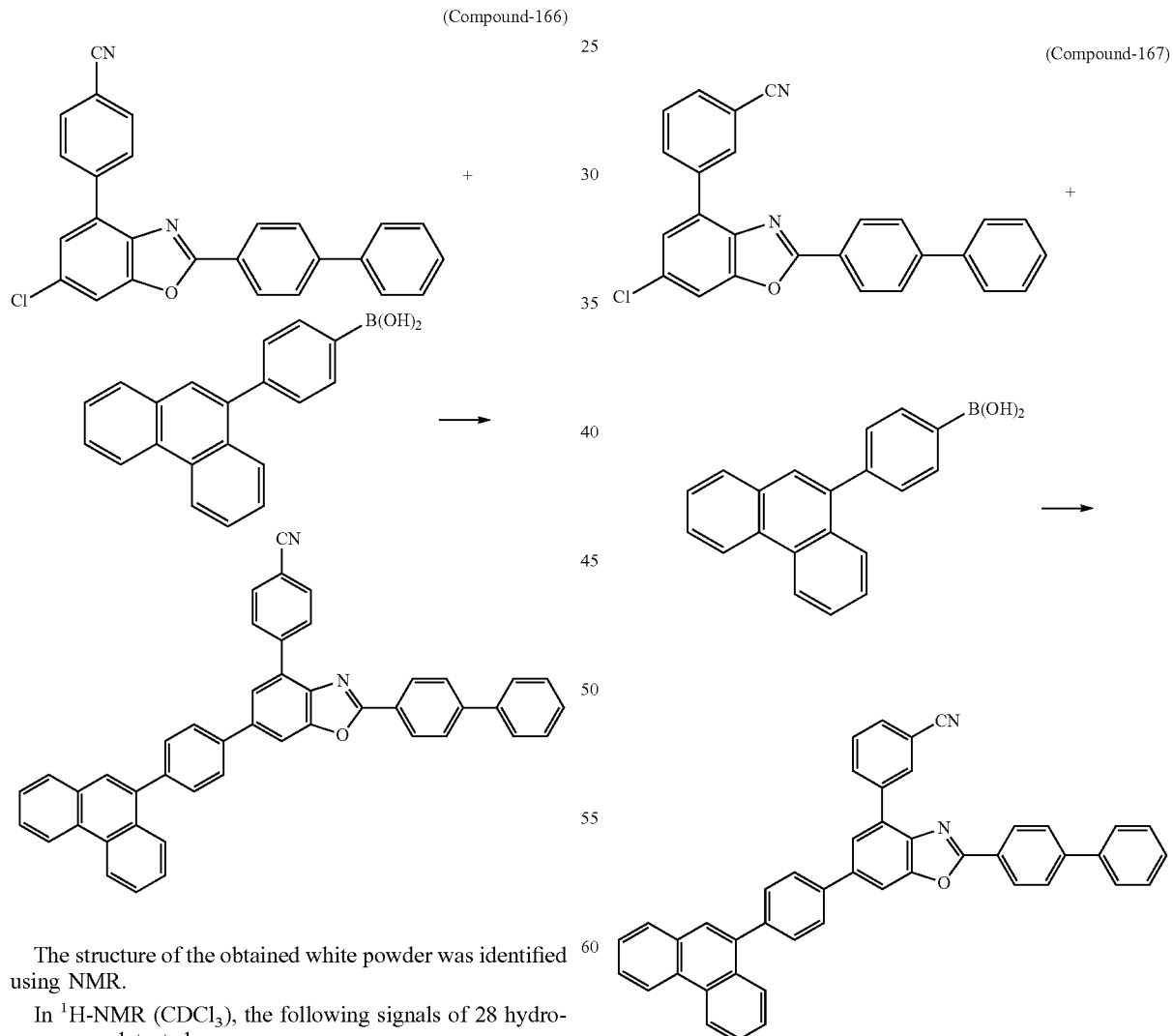

The structure of the obtained white powder was identified using NMR.

In $^1$H-NMR (CDCl$_3$), the following signals of 28 hydrogens were detected.

δ (ppm)=8.85 (1H), 8.78 (1H), 8.44 (2H), 8.34 (2H) 8.05 (1H), 7.96 (3H), 7.89 (4H), 7.83 (2H), 7.79 (1H), 7.77-7.68 (6H), 7.66 (1H), 7.62 (1H), 7.53 (2H), 7.45 (1H)

The structure of the obtained white powder was identified using NMR.

In ¹H-NMR (CDCl₃), the following signals of 28 hydrogens were detected.

δ (ppm)=8.84 (1H), 8.78 (1H), 8.56 (1H), 8.43 (3H), 8.05 (1H), 7.97 (1H), 7.96 (1H), 7.90 (2H), 7.85 (2H), 7.82-7.68 (10H), 7.63 (2H), 7.53 (2H), 7.45 (1H)

Example 48

Synthesis of 2-(biphenyl-4-yl)-4-(4'-cyano-biphenyl-4-yl)-6-(phenanthrene-9-yl)-benzoxazole (Compound-168)

First, 9.4 g of 2-(4-chloro-phenyl)-4-(4'-cyano-biphenyl-4-yl)-6-(phenanthrene-9-yl)-benzoxazole, 2.1 g of phenylboronic acid, 0.4 g of tris(dibenzylideneacetone)dipalladium (0), 0.5 g of tricyclohexylphosphine, and 6.8 g of tripotassium phosphate were placed in a reaction vessel, and stirred in a mixed solvent of 1,4-dioxane/H₂O under reflux overnight. After allowing to cool, methanol was added to the system for dispersing and washing, and the resulting system was filtered to obtain a crude product. The obtained crude product was purified through recrystallization from monochlorobenzene as solvent thereby obtain 5.2 g (yield: 51%) of a white powder of 2-(biphenyl-4-yl)-4-(4'-cyano-biphenyl-4-yl)-6-(phenanthrene-9-yl)-benzoxazole (Compound-168).

(Compound-168)

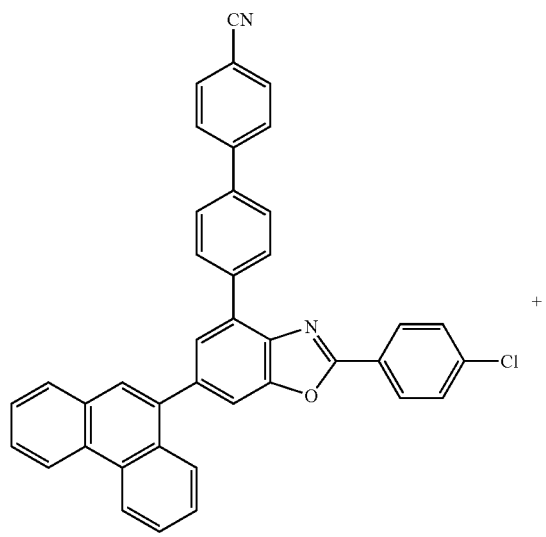

+

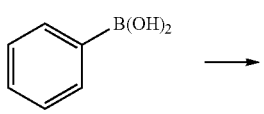

→

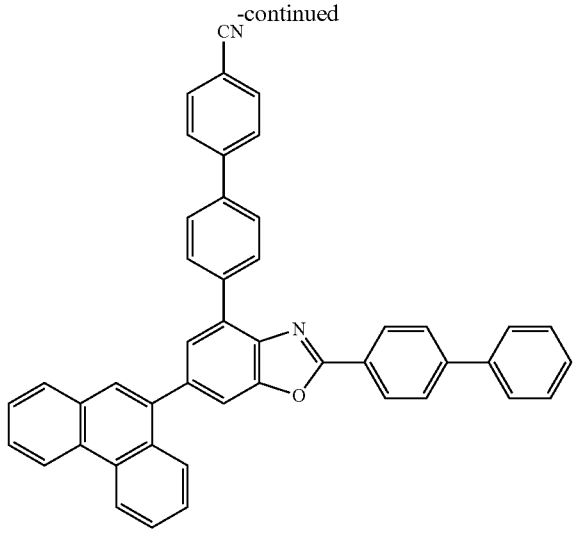

The structure of the obtained white powder was identified using NMR.

In ¹H-NMR (CDCl₃), the following signals of 28 hydrogens were detected.

δ (ppm)=8.86 (1H), 8.80 (1H), 8.46 (2H), 8.32 (2H), 8.07 (1H), 7.96 (1H), 7.88-7.77 (11H), 7.77-7.65 (5H), 7.61 (1H), 7.53 (2H), 7.45 (1H).

Example 49

Synthesis of 2-(biphenyl-4-yl)-6-(4'-cyano-biphenyl-4-yl)-4-{4-(pyridine-3-yl)-phenyl}-benzoxazole (Compound-173)

First, 7.5 g of 2-(biphenyl-4-yl)-6-chloro-4-{4-(pyridine-3-yl)-phenyl}-benzoxazole, 5.5 g of 4'-(4,4,5,5-tetramethyl-[1,3,2]dioxaborolane-2-yl)biphenyl-4-carbonitrile, 0.8 g of tris(dibenzylideneacetone)dipalladium(0), 0.9 g of tricyclohexylphosphine, and 10.4 g of tripotassium phosphate were placed in a reaction vessel, and stirred in a mixed solvent of 1,4-dioxane/H₂O under reflux overnight. After allowing to cool, water was added to the system for dispersing and washing, and the resulting system was filtered to obtain a crude product. The obtained crude product was purified through crystallization from a mixed solvent of N-methylpyrrolidone/acetone to thereby obtain 6.5 g (yield: 66%) of a pale yellow powder of 2-(biphenyl-4-yl)-6-(4'-cyano-biphenyl-4-yl)-4-{4-(pyridine-3-yl)-phenyl}-benzoxazole (Compound-173).

(Compound-173)

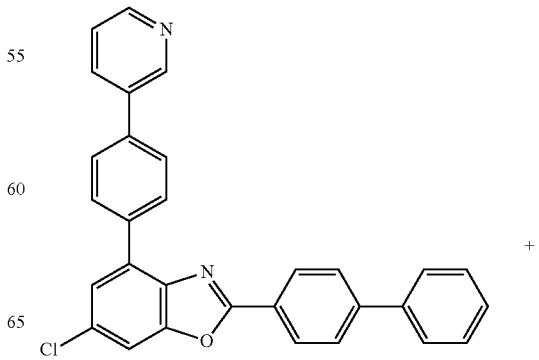

+

-continued

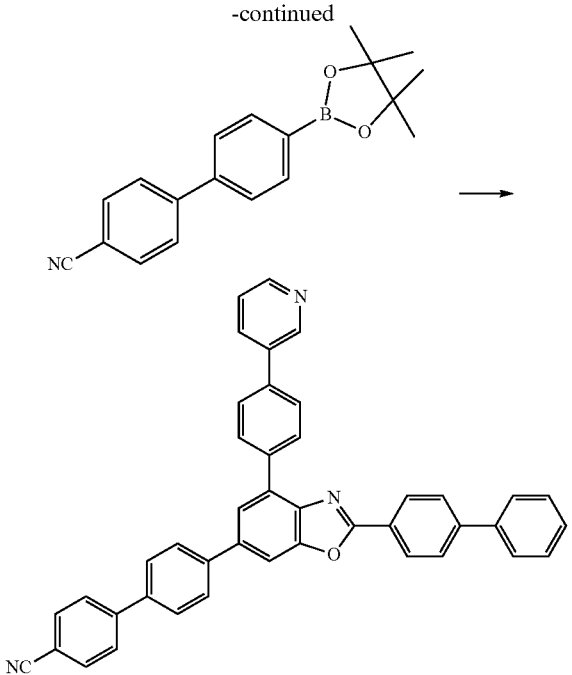

The structure of the obtained pale yellow powder was identified using NMR.

In ¹H-NMR (CDCl₃), the following signals of 27 hydrogens were detected.

δ (ppm)=9.00 (1H), 8.67 (1H), 8.43 (2H), 8.29 (2H), 8.01 (1H), 7.92-7.73 (14H), 7.72 (2H), 7.53 (2H), 7.44 (2H)

Example 50

Synthesis of 6-(4'-cyano-biphenyl-4-yl)-4-phenyl-2-{4'-(pyridine-3-yl)-biphenyl-4-yl}-benzoxazole (Compound-175)

First, 16.3 g of 2-(4-chloro-phenyl)-6-(4'-cyano-biphenyl-4-yl)-4-phenyl-benzoxazole, 7.1 g of 4-(pyridine-3-yl)phenylboronic acid, 0.6 g of tris(dibenzylideneacetone)dipalladium(0), 0.4 g of tricyclohexylphosphine, and 12.2 g of tripotassium phosphate were placed in a reaction vessel, and stirred in a mixed solvent of 1,4-dioxane/H₂O under reflux overnight. After allowing to cool, methanol was added to the system for dispersing and washing, and the resulting system was filtered to obtain a crude product. The obtained crude product was purified through recrystallization from 1,2-dichlorobenzene as solvent to thereby obtain 19.4 g (yield: 96%) of a pale yellow powder of 6-(4'-cyano-biphenyl-4-yl)-4-phenyl-2-{4'-(pyridine-3-yl)-biphenyl-4-yl}-benzoxazole (Compound-175).

(Compound-175)

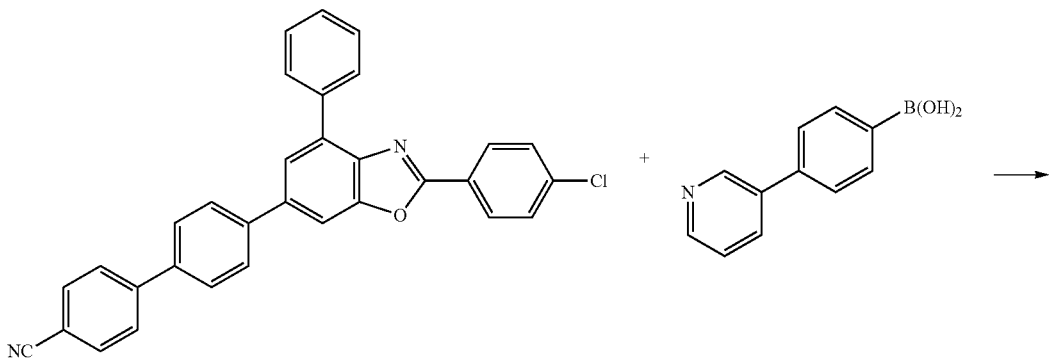

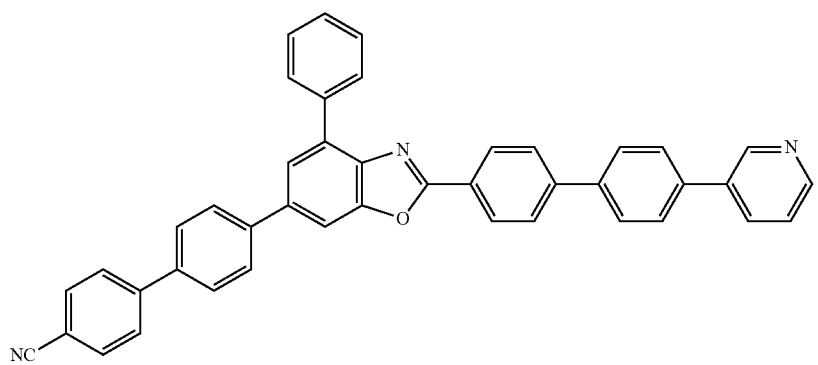

The structure of the obtained pale yellow powder was identified using NMR.

In $^1$H-NMR (CDCl$_3$), the following signals of 27 hydrogens were detected.

δ (ppm)=8.95 (1H), 8.66 (1H), 8.44 (2H), 8.15 (2H), 7.92 (1H), 7.89-7.70 (16H), 7.61 (2H), 7.49 (1H), 7.43 (1H)

Example 51

Synthesis of 2-(biphenyl-4-yl)-4-(4'-cyano-biphenyl-4-yl)-6-{4-(pyridine-3-yl)-phenyl}-benzoxazole (Compound-179)

First, 11.8 g of 2-(biphenyl-4-yl)-6-chloro-4-(4'-cyano-biphenyl-4-yl)-benzoxazole, 5.1 g of 4-(pyridine-3-yl)phenylboronic acid, 0.7 g of tris(dibenzylideneacetone)dipalladium(0), 0.7 g of tricyclohexylphosphine, and 10.3 g of tripotassium phosphate were placed in a reaction vessel, and stirred in a mixed solvent of 1,4-dioxane/H$_2$O under reflux overnight. After allowing to cool, methanol was added to the system for dispersing and washing, and the resulting system was filtered to obtain a crude product. The obtained crude product was purified through crystallization from a mixed solvent of monochlorobenzene/acetone to thereby obtain 10.5 g (yield: 72%) of a pale yellow powder of 2-(biphenyl-4-yl)-4-(4'-cyano-biphenyl-4-yl)-6-{4-(pyridine-3-yl)-phenyl}-benzoxazole (Compound-179).

(Compound-179)

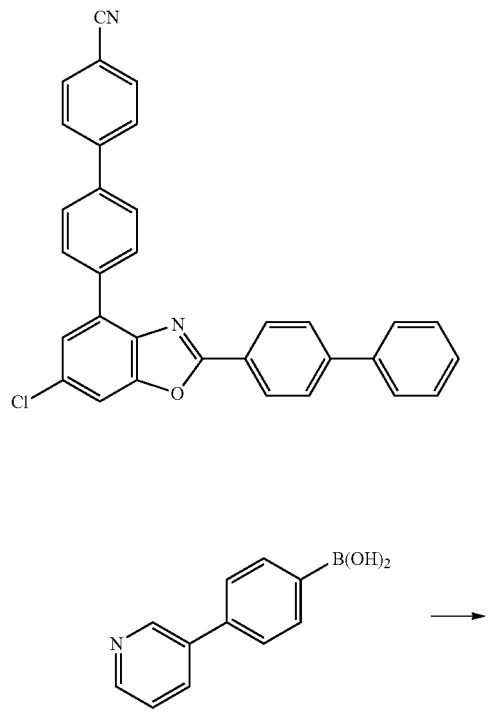

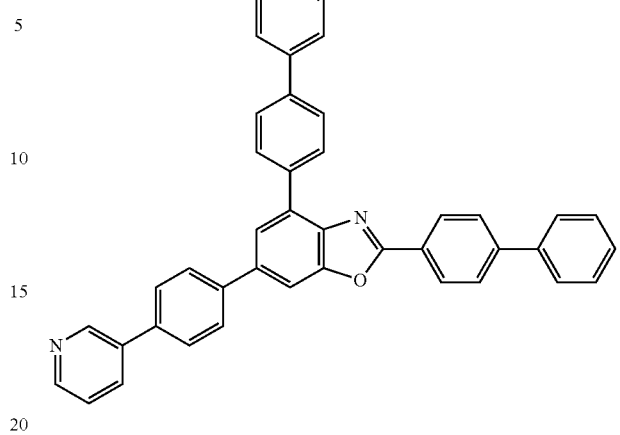

The structure of the obtained pale yellow powder was identified using NMR.

In $^1$H-NMR (CDCl$_3$), the following signals of 27 hydrogens were detected.

δ (ppm)=8.97 (1H), 8.66 (1H), 8.41 (2H), 8.28 (2H), 7.97 (1H), 7.91-7.66 (16H), 7.52 (2H), 7.44 (2H)

Example 52

Synthesis of 2-(biphenyl-4-yl)-4-(4'-cyano-biphenyl-3-yl)-6-{4-(pyridine-3-yl)-phenyl}-benzoxazole (Compound-180)

First, 5.0 g of 2-(biphenyl-4-yl)-6-chloro-4-(4'-cyano-biphenyl-3-yl)-benzoxazole, 2.3 g of 4-(pyridine-3-yl)phenylboronic acid, 0.2 g of tris(dibenzylideneacetone)dipalladium (0), 0.3 g of tricyclohexylphosphine, and 6.6 g of tripotassium phosphate were placed in a reaction vessel, and stirred in a mixed solvent of 1,4-dioxane/H$_2$O under reflux overnight. After allowing to cool, water was added to the system for dispersing and washing, and the resulting system was filtered to obtain a crude product. The obtained crude product was purified through recrystallization from 1,2-dichlorobenzene as solvent to thereby obtain 5.4 g (yield: 87%) of a pale yellow powder of 2-(biphenyl-4-yl)-4-(4'-cyano-biphenyl-3-yl)-6-{4-(pyridine-3-yl)-phenyl}-benzoxazole (Compound-180).

(Compound-180)

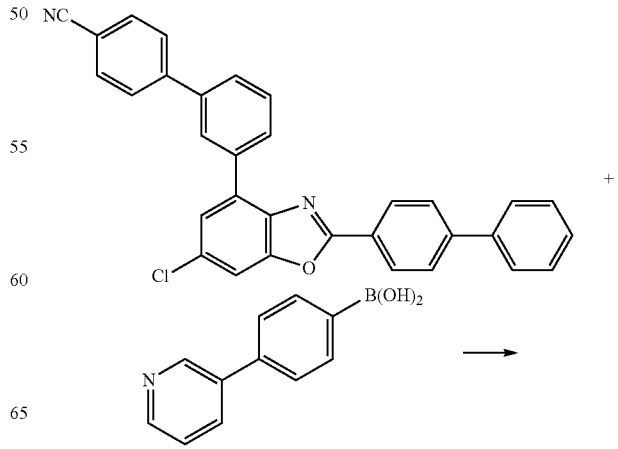

-continued

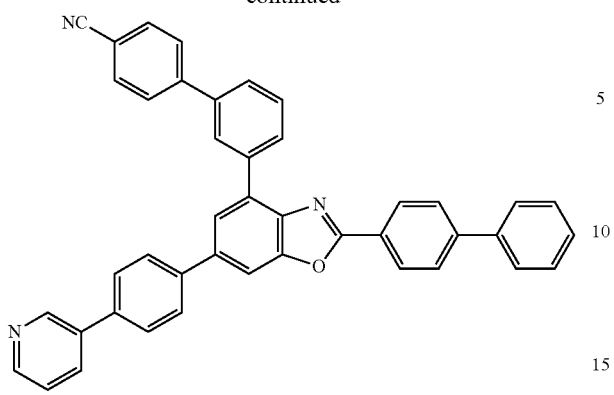

The structure of the obtained pale yellow powder was identified using NMR.

In $^1$H-NMR (CDCl$_3$), the following signals of 27 hydrogens were detected.

δ (ppm)=8.96 (1H), 8.67 (1H), 8.41 (1H), 8.39 (2H), 8.19 (1H), 7.98 (1H), 7.92-7.74 (11H), 7.71 (5H), 7.53 (2H), 7.44 (2H)

Example 53

Synthesis of 2-(biphenyl-4-yl)-4-(3'-cyano-biphenyl-4-yl)-6-{4-(pyridine-3-yl)-phenyl}-benzoxazole (Compound-181)

First, 6.0 g of 2-(biphenyl-4-yl)-6-chloro-4-(3'-cyano-biphenyl-4-yl)-benzoxazole, 3.0 g of 4-(pyridine-3-yl)phenyl-boronic acid, 0.3 g of tris(dibenzylideneacetone)dipalladium (0), 0.4 g of tricyclohexylphosphine, and 7.9 g of tripotassium phosphate were placed in a reaction vessel, and stirred in a mixed solvent of 1,4-dioxane/H$_2$O under reflux overnight. After allowing to cool, water was added to the system for dispersing and washing, and the resulting system was filtered to obtain a crude product. The obtained crude product was purified through crystallization from a mixed solvent of monochlorobenzene/acetone to thereby obtain 5.2 g (yield: 70%) of a pale yellow powder of 2-(biphenyl-4-yl)-4-(3'-cyano-biphenyl-4-yl)-6-{4-(pyridine-3-yl)-phenyl}-benzoxazole (Compound-181).

(Compound-181)

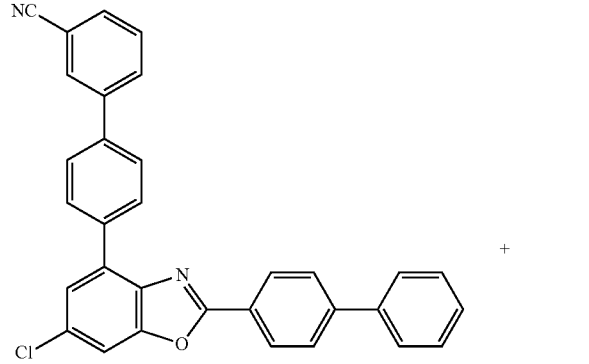

+

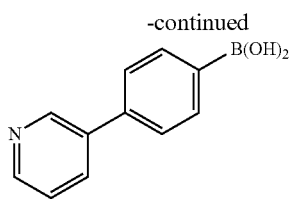

→

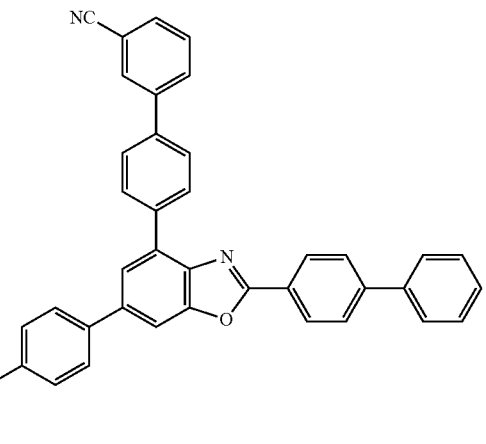

The structure of the obtained pale yellow powder was identified using NMR.

In $^1$H-NMR (CDCl$_3$), the following signals of 27 hydrogens were detected.

δ (ppm)=8.92 (1H), 8.67 (1H), 8.43 (2H), 8.29 (2H), 8.00 (1H), 7.95 (2H), 7.88 (3H), 7.84-7.73 (6H), 7.70 (3H), 7.64 (2H), 7.53 (2H), 7.45 (2H)

Example 54

Synthesis of 2-(biphenyl-4-yl)-4-(4'-cyano-biphenyl-4-yl)-6-{4-(pyridine-2-yl)-phenyl}-benzoxazole (Compound-182)

First, 6.0 g of 2-(biphenyl-4-yl)-6-chloro-4-(4'-cyano-biphenyl-4-yl)-benzoxazole, 4.2 g of 2-{4-(4,4,5,5-tetramethyl-[1,3,2]dioxaborolane-2-yl)-phenyl}-pyridine, 0.3 g of tris(dibenzylideneacetone)dipalladium(0), 0.4 g of tricyclohexylphosphine, and 7.9 g of tripotassium phosphate were placed in a reaction vessel, and stirred in a mixed solvent of 1,4-dioxane/H$_2$O under reflux overnight. After allowing to cool, water was added to the system for dispersing and washing, and the resulting system was filtered to obtain a crude product. The obtained crude product was purified through crystallization from a mixed solvent of monochlorobenzene/acetone to thereby obtain 5.4 g (yield: 72%) of a pale yellow powder of 2-(biphenyl-4-yl)-4-(4'-cyano-biphenyl-4-yl)-6-{4-(pyridine-2-yl)-phenyl}-benzoxazole (Compound-182).

(Compound-182)

The structure of the obtained pale yellow powder was identified using NMR.

In ¹H-NMR (CDCl₃), the following signals of 27 hydrogens were detected.

δ (ppm)=8.77 (1H), 8.42 (2H), 8.30 (2H), 8.18 (2H), 7.92-7.73 (13H), 7.70 (3H), 7.52 (2H), 7.45 (1H), 7.31 (1H)

Example 55

Synthesis of 2-[4-{7-(4'-cyano-biphenyl-4-yl)-9,9-diphenyl-9H-fluorene-2-yl}-phenyl]-benzoxazole (Compound-201)

First, 2.8 g of 2-{4-(4,4,5,5-tetramethyl-[1,3,2]dioxaborolane-2-yl)-phenyl}-benzoxazole, 4.5 g of 4'-(7-bromo-9,9-diphenyl-9H-fluorene-2-yl)-biphenyl-4-carbonitrile, 0.5 g of tetrakis(triphenylphosphine)dipalladium (0), and 1.6 g of potassium carbonate were placed in a reaction vessel, and stirred in a mixed solvent of toluene/ethanol/H₂O under reflux overnight. After allowing to cool, methanol was added to the system for dispersing and washing, and the resulting system was filtered to obtain a crude product. The obtained crude product was purified through recrystallization from monochlorobenzene as solvent to thereby obtain 5.0 g (yield: 93%) of a yellow powder of 2-[4-{7-(4'-cyano-biphenyl-4-yl)-9,9-diphenyl-9H-fluorene-2-yl}-phenyl]-benzoxazole (Compound-201).

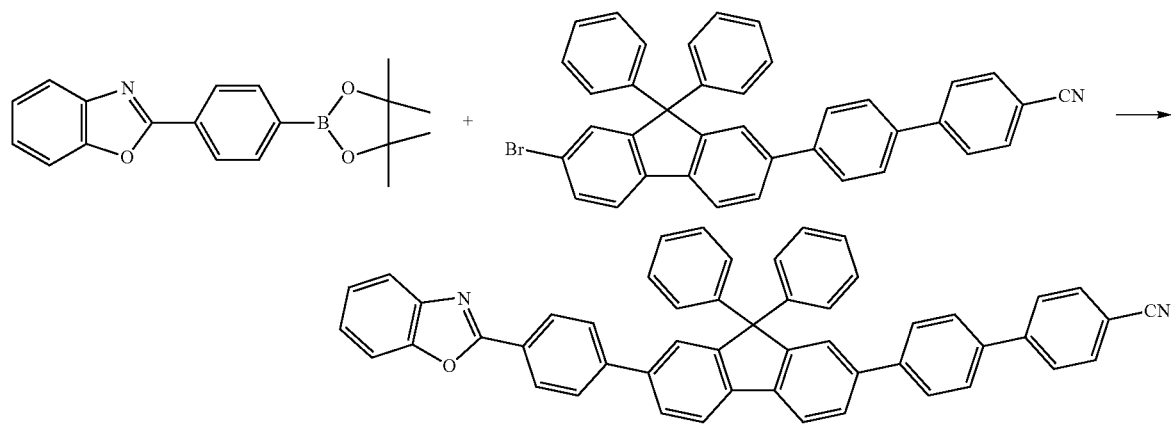

(Compound-201)

The structure of the obtained yellow powder was identified using NMR.

In $^1$H-NMR (CDCl$_3$), the following signals of 32 hydrogens were detected.

δ (ppm)=8.33 (2H), 7.93 (2H), 7.84-7.59 (16H), 7.44-7.23 (12H)

Example 56

The melting point and the glass transition point of each of the compounds having a benzazole ring structure obtained in Examples 1 to 55 above were measured using a high-sensitivity differential scanning calorimeter (DSC3100SA manufactured by Bruker AXS K.K.). Table 1 shows the results.

TABLE 1

| Compound | Melting point | Glass transition point |
|---|---|---|
| Compound of Ex. 1 | —° C. | 142° C. |
| Compound of Ex. 2 | 288° C. | 169° C. |
| Compound of Ex. 3 | 315° C. | 135° C. |
| Compound of Ex. 4 | 253° C. | 137° C. |
| Compound of Ex. 5 | 282° C. | 150° C. |
| Compound of Ex. 6 | 252° C. | 118° C. |
| Compound of Ex. 7 | 329° C. | —° C. |
| Compound of Ex. 8 | 276° C. | —° C. |
| Compound of Ex. 9 | 341° C. | —° C. |
| Compound of Ex. 10 | 283° C. | 138° C. |
| Compound of Ex. 11 | —° C. | 143° C. |
| Compound of Ex. 12 | 361° C. | —° C. |
| Compound of Ex. 13 | 243° C. | 127° C. |
| Compound of Ex. 14 | 218° C. | 102° C. |
| Compound of Ex. 15 | —° C. | 130° C. |
| Compound of Ex. 16 | —° C. | 113° C. |
| Compound of Ex. 17 | —° C. | 156° C. |
| Compound of Ex. 18 | 278° C. | 131° C. |
| Compound of Ex. 19 | 263° C. | 123° C. |
| Compound of Ex. 20 | 243° C. | 124° C. |
| Compound of Ex. 21 | 234° C. | 100° C. |
| Compound of Ex. 22 | 321° C. | 153° C. |
| Compound of Ex. 23 | 244° C. | 96° C. |
| Compound of Ex. 24 | 292° C. | 127° C. |
| Compound of Ex. 25 | 259° C. | 132° C. |
| Compound of Ex. 26 | 302° C. | —° C. |
| Compound of Ex. 27 | 308° C. | 146° C. |
| Compound of Ex. 28 | 250° C. | 121° C. |
| Compound of Ex. 29 | 236° C. | 125° C. |
| Compound of Ex. 30 | —° C. | 170° C. |
| Compound of Ex. 31 | 253° C. | 143° C. |
| Compound of Ex. 32 | 278° C. | 155° C. |
| Compound of Ex. 33 | 265° C. | 138° C. |
| Compound of Ex. 34 | 288° C. | 154° C. |
| Compound of Ex. 35 | 295° C. | 182° C. |
| Compound of Ex. 36 | 254° C. | 120° C. |
| Compound of Ex. 37 | 274° C. | 116° C. |
| Compound of Ex. 38 | 282° C. | —° C. |
| Compound of Ex. 39 | 274° C. | 143° C. |
| Compound of Ex. 40 | 267° C. | —° C. |
| Compound of Ex. 41 | 267° C. | 126° C. |
| Compound of Ex. 42 | 290° C. | 119° C. |
| Compound of Ex. 43 | 255° C. | 138° C. |
| Compound of Ex. 44 | —° C. | 130° C. |
| Compound of Ex. 45 | 258° C. | 116° C. |
| Compound of Ex. 46 | 304° C. | 137° C. |
| Compound of Ex. 47 | 251° C. | 124° C. |
| Compound of Ex. 48 | —° C. | 149° C. |
| Compound of Ex. 49 | —° C. | 125° C. |
| Compound of Ex. 50 | 309° C. | —° C. |
| Compound of Ex. 51 | 237° C. | 125° C. |
| Compound of Ex. 52 | 262° C. | 109° C. |
| Compound of Ex. 53 | —° C. | 110° C. |
| Compound of Ex. 54 | —° C. | 126° C. |
| Compound of Ex. 55 | 336° C. | —° C. |

The compounds having a benzazole ring structure obtained in Examples 1 to 55 above had a glass transition point of 98° C. or higher, which means that these compounds are stable in the form of a thin film.

Example 57

A vapor-deposited film (thickness: 100 nm) of the compound having a benzazole ring structure obtained in Examples 1 to 55 above was formed on an ITO substrate, and the work function was measured using an ionization potential measuring device (PYS-202 manufactured by Sumitomo Heavy Industries, Ltd.). Table 2 shows the results.

TABLE 2

| Compound | Work function |
|---|---|
| Compound of Ex. 1 | 6.38 eV |
| Compound of Ex. 2 | 6.42 eV |
| Compound of Ex. 3 | 6.40 eV |
| Compound of Ex. 4 | 6.31 eV |
| Compound of Ex. 5 | 6.35 eV |
| Compound of Ex. 6 | 6.37 eV |
| Compound of Ex. 7 | 6.40 eV |
| Compound of Ex. 8 | 6.36 eV |
| Compound of Ex. 9 | 6.46 eV |
| Compound of Ex. 10 | 6.31 eV |
| Compound of Ex. 11 | 6.46 eV |
| Compound of Ex. 12 | 6.38 eV |
| Compound of Ex. 13 | 6.24 eV |
| Compound of Ex. 14 | 6.41 eV |
| Compound of Ex. 15 | 6.38 eV |
| Compound of Ex. 16 | 6.40 eV |
| Compound of Ex. 17 | 6.41 eV |
| Compound of Ex. 18 | 6.39 eV |
| Compound of Ex. 19 | 6.49 eV |
| Compound of Ex. 20 | 6.69 eV |
| Compound of Ex. 21 | 6.39 eV |
| Compound of Ex. 22 | 6.53 eV |
| Compound of Ex. 23 | 6.52 eV |
| Compound of Ex. 24 | 6.41 eV |
| Compound of Ex. 25 | 6.51 eV |
| Compound of Ex. 26 | 6.30 eV |
| Compound of Ex. 27 | 6.41 eV |
| Compound of Ex. 28 | 6.38 eV |
| Compound of Ex. 29 | 6.40 eV |
| Compound of Ex. 30 | 6.45 eV |
| Compound of Ex. 31 | 6.44 eV |
| Compound of Ex. 32 | 6.38 eV |
| Compound of Ex. 33 | 6.38 eV |
| Compound of Ex. 34 | 6.52 eV |
| Compound of Ex. 35 | 6.51 eV |
| Compound of Ex. 36 | 6.46 eV |
| Compound of Ex. 37 | 6.38 eV |
| Compound of Ex. 38 | 6.29 eV |
| Compound of Ex. 39 | 6.47 eV |
| Compound of Ex. 40 | 6.35 eV |
| Compound of Ex. 41 | 6.37 eV |
| Compound of Ex. 42 | 6.19 eV |
| Compound of Ex. 43 | 6.36 eV |
| Compound of Ex. 44 | 6.43 eV |
| Compound of Ex. 45 | 6.40 eV |
| Compound of Ex. 46 | 6.40 eV |
| Compound of Ex. 47 | 6.38 eV |
| Compound of Ex. 48 | 6.42 eV |
| Compound of Ex. 49 | 6.38 eV |
| Compound of Ex. 50 | 6.36 eV |
| Compound of Ex. 51 | 6.41 eV |
| Compound of Ex. 52 | 6.40 eV |
| Compound of Ex. 53 | 6.38 eV |
| Compound of Ex. 54 | 6.39 eV |
| Compound of Ex. 55 | 6.31 eV |

The compounds having a benzazole ring structure obtained in Examples 1 to 55 above had a work function larger than 5.5 eV, whereas the work function of common hole-transporting materials such as NPD and TPD is generally 5.5 eV. This means that the compounds having a benzazole ring structure obtained in Examples have good hole-blocking capability.

Example 58

Figure 15:
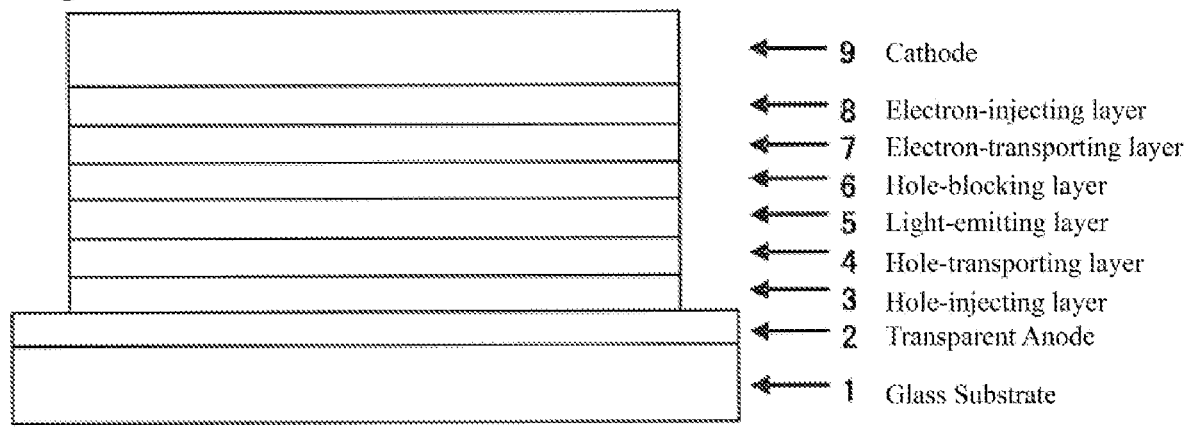
FIG. 15 shows the configuration of organic EL elements of Examples 58 to 112 and Comparative Examples 1 and 2.

An organic EL element as shown in FIG. 15 was prepared by vapor-depositing, on an ITO electrode as a transparent anode 2 that had been formed on a glass substrate 1, a hole-injecting layer 3, a hole-transporting layer 4, a light-emitting layer 5, a hole-blocking layer 6, an electron-transporting layer 7, an electron-injecting layer 8, and a cathode (aluminum electrode) 9 in this order.

Specifically, a glass substrate 1 having an ITO film with a thickness of 50 nm as a transparent anode 2 was ultrasonically cleaned in isopropyl alcohol for 20 minutes, and then dried for 10 minutes on a hot plate heated to 200° C. After that, UV/ozone treatment was performed for 15 minutes. Then, the glass substrate with ITO was set inside a vacuum vapor deposition machine, and the pressure was reduced to 0.001 Pa or less. Subsequently, an electron acceptor (Acceptor-1) having the structural formula below and a compound (HTM-1) having the structural formula below were vapor-deposited so as to coat the transparent anode 2 through binary vapor deposition at vapor deposition rates such that the ratio of the vapor deposition rate of Acceptor-1 to that of HTM-1 was 3:97, to thereby form a hole-injecting layer 3 with a thickness of 10 nm.

On this hole-injecting layer 3, a hole-transporting layer 4 (thickness: 60 nm) made of the compound (HTM-1) having the structural formula below was formed.

A compound (EMD-1) having the structural formula below and a compound (EMH-1) having the structural formula below were vapor-deposited on the hole-transporting layer 4 through binary vapor deposition at vapor deposition rates such that the ratio of the vapor deposition rate of EMD-1 to that of EMH-1 was 5:95, to thereby form a light-emitting layer 5 with a thickness of 20 nm.

The compound of Example 1 (Compound-2) and a compound (ETM-1) having the structural formula below were vapor-deposited on this light-emitting layer 5 through binary vapor deposition at vapor deposition rates such that the ratio of the vapor deposition rate of Compound-2 to that of ETM-1 was 50:50, to thereby from a layer (thickness: 30 nm) serving as both a hole-blocking layer 6 and an electron-transporting layer 7.

On this layer serving as both the hole-blocking layer 6 and the electron-transporting layer 7, an electron-injecting layer 8 (thickness: 1 nm) made of lithium fluoride was formed. Finally, aluminum was vapor-deposited to a thickness of 100 nm to thereby form a cathode 9.

The prepared organic EL element were characterized in the atmosphere at normal temperature. Tables 3 and 4 collectively show the measurement results of light emission characteristics when a DC voltage was applied to the prepared organic EL element.

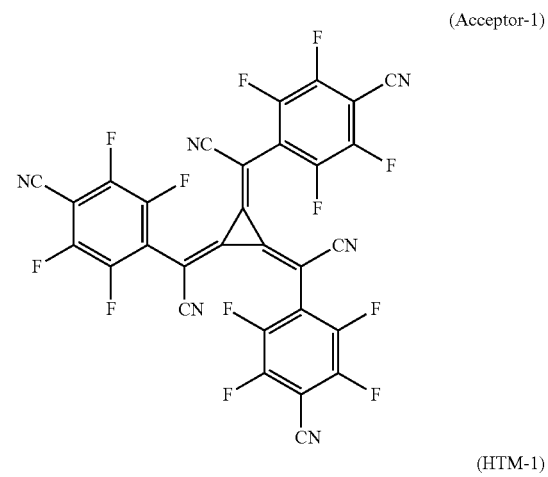

(Acceptor-1)

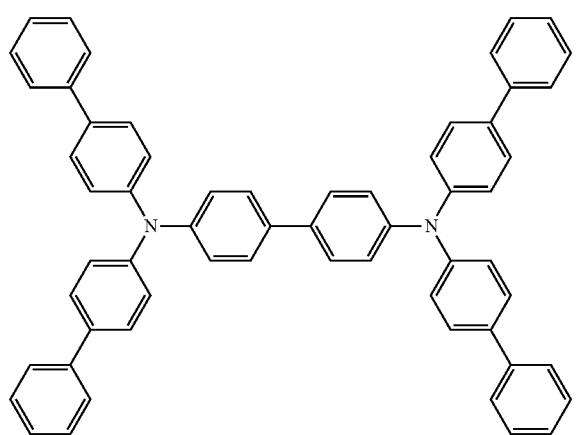

(HTM-1)

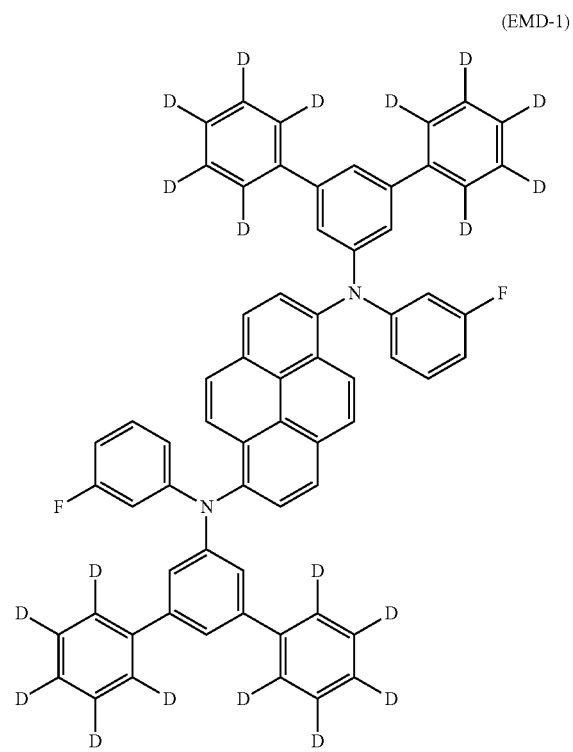

(EMD-1)

(EMH-1)

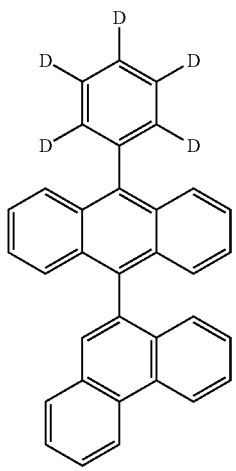

(Compound-2)

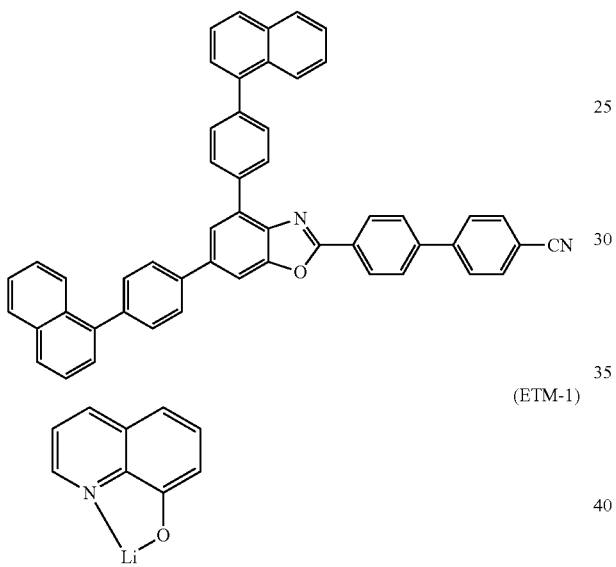

(ETM-1)

Examples 59 to 112

Organic EL elements were prepared under the same conditions as in Example 58, except that, instead of the compound of Example 1 (Compound-2), the compounds of Examples 2 to 55, respectively, were used as the material for the layer serving as both the hole-blocking layer 6 and the electron-transporting layer 7, and that binary vapor deposition was performed at vapor deposition rates such that the ratio of the vapor deposition rate of the compounds of Examples 2 to 55 to that of ETM-1 was 50:50. The prepared organic EL elements were characterized in the atmosphere at normal temperature. Tables 3 and 4 collectively show the measurement results of light emission characteristics when a DC voltage was applied to the prepared organic EL element.

Comparative Example 1

For comparison, an organic EL element was prepared under the same conditions as in Example 58, except that, instead of the compound of Example 1 (Compound-2), a compound (ETM-2) having the structural formula below (see Patent Literature 8, for example) was used as the material for the layer serving as both the hole-blocking layer 6 and the electron-transporting layer 7, and that binary vapor deposition was performed at vapor deposition rates such that the ratio of the vapor deposition rate of ETM-2 to that of ETM-1 was 50:50. The prepared organic EL element was characterized in the atmosphere at normal temperature. Tables 3 and 4 collectively show the measurement results of light emission characteristics when a DC voltage was applied to the prepared organic EL element.

(ETM-2)

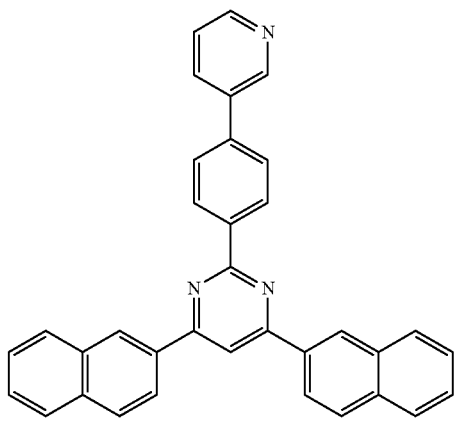

Comparative Example 2

For comparison, an organic EL element was prepared under the same conditions as in Example 58, except that, instead of the compound of Example 1 (Compound-5), a compound (ETM-3) having the structural formula below (see Patent Literature 9, for example) was used as the material for the layer serving as both the hole-blocking layer 6 and the electron-transporting layer 7, and that binary vapor deposition was performed at vapor deposition rates such that the ratio of the vapor deposition rate of ETM-3 to that of ETM-1 was 50:50. The prepared organic EL element was characterized in the atmosphere at normal temperature. Tables 3 and 4 collectively show the measurement results of light emission characteristics when a DC voltage was applied to the prepared organic EL element.

(ETM-3)

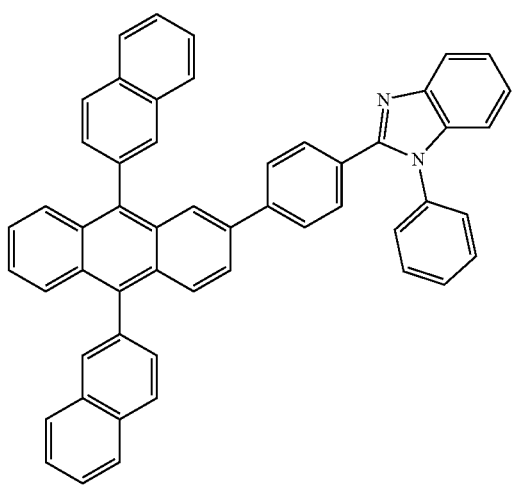

The element lifespan of the organic EL elements prepared in Examples 58 to 112 and Comparative Examples 1 and 2 was measured. Tables 3 and 4 collectively show the results. The element lifespan was defined as follows: the organic EL element was driven by constant current to emit light at an initial luminance (luminance when light emission started) of 2,000 cd/m², and the time taken for the luminance to decay to 1,900 cd/m² (corresponding to 95% based on the initial luminance (100%): 95% decay) was determined and defined as the element lifespan.

TABLE 3

|  | Layer serving as both hole-blocking layer and electron-transporting layer | Voltage [V] (@10 mA/cm²) | Luminance [cd/m²] (@10 mA/cm²) | Luminous efficacy [cd/A] (@10 mA/cm²) | Power efficiency [lm/W] (@10 mA/cm²) | Element lifespan (95% decay) |
|---|---|---|---|---|---|---|
| Ex. 58 | Compound-2/ETM-1 | 3.54 | 873 | 8.73 | 7.75 | 294 hours |
| Ex. 59 | Compound-10/ETM-1 | 3.50 | 876 | 8.77 | 7.89 | 248 hours |
| Ex. 60 | Compound-22/ETM-1 | 3.43 | 894 | 8.95 | 8.21 | 287 hours |
| Ex. 61 | Compound-23/ETM-1 | 3.41 | 883 | 8.84 | 8.14 | 267 hours |
| Ex. 62 | Compound-24/ETM-1 | 3.43 | 879 | 8.80 | 8.06 | 288 hours |
| Ex. 63 | Compound-27/ETM-1 | 3.51 | 866 | 8.67 | 7.77 | 247 hours |
| Ex. 64 | Compound-75/ETM-1 | 3.68 | 886 | 8.87 | 7.58 | 249 hours |
| Ex. 65 | Compound-77/ETM-1 | 3.38 | 887 | 8.87 | 8.25 | 261 hours |
| Ex. 66 | Compound-84/ETM-1 | 3.49 | 866 | 8.68 | 7.81 | 246 hours |
| Ex. 67 | Compound-104/ETM-1 | 3.48 | 823 | 8.22 | 7.42 | 288 hours |
| Ex. 68 | Compound-105/ETM-1 | 3.67 | 893 | 8.94 | 7.65 | 263 hours |
| Ex. 69 | Compound-106/ETM-1 | 3.43 | 877 | 8.78 | 8.05 | 258 hours |
| Ex. 70 | Compound-108/ETM-1 | 3.48 | 892 | 8.94 | 8.08 | 280 hours |
| Ex. 71 | Compound-109/ETM-1 | 3.53 | 875 | 8.77 | 7.80 | 270 hours |
| Ex. 72 | Compound-110/ETM-1 | 3.70 | 884 | 8.85 | 7.52 | 256 hours |
| Ex. 73 | Compound-111/ETM-1 | 3.50 | 879 | 8.80 | 7.91 | 288 hours |
| Ex. 74 | Compound-115/ETM-1 | 3.44 | 892 | 8.93 | 8.16 | 251 hours |
| Ex. 75 | Compound-117/ETM-1 | 3.47 | 859 | 8.60 | 7.78 | 281 hours |
| Ex. 76 | Compound-118/ETM-1 | 3.35 | 888 | 8.89 | 8.34 | 266 hours |
| Ex. 77 | Compound-119/ETM-1 | 3.52 | 880 | 8.81 | 7.87 | 246 hours |
| Ex. 78 | Compound-120/ETM-1 | 3.47 | 900 | 9.01 | 8.15 | 271 hours |
| Ex. 79 | Compound-123/ETM-1 | 3.55 | 898 | 8.99 | 7.97 | 247 hours |
| Ex. 80 | Compound-127/ETM-1 | 3.53 | 852 | 8.53 | 7.59 | 284 hours |
| Ex. 81 | Compound-128/ETM-1 | 3.61 | 847 | 8.48 | 7.38 | 278 hours |
| Ex. 82 | Compound-130/ETM-1 | 3.46 | 894 | 8.95 | 8.14 | 249 hours |
| Ex. 83 | Compound-136/ETM-1 | 3.50 | 882 | 8.82 | 7.93 | 251 hours |
| Ex. 84 | Compound-137/ETM-1 | 3.42 | 877 | 8.77 | 8.06 | 267 hours |

TABLE 4

|  | Layer serving as both hole-blocking layer and electron-transporting layer | Voltage [V] (@10 mA/cm²) | Luminance [cd/m²] (@10 mA/cm²) | Luminous efficacy [cd/A] (@10 mA/cm²) | Power efficiency [lm/W] (@10 mA/cm²) | Element lifespan (95% decay) |
|---|---|---|---|---|---|---|
| Ex. 85 | Compound-138/ETM-1 | 3.53 | 879 | 8.80 | 7.83 | 246 hours |
| Ex. 86 | Compound-143/ETM-1 | 3.46 | 893 | 8.94 | 8.13 | 268 hours |
| Ex. 87 | Compound-144/ETM-1 | 3.56 | 848 | 8.48 | 7.49 | 271 hours |
| Ex. 88 | Compound-147/ETM-1 | 3.53 | 839 | 8.39 | 7.47 | 300 hours |
| Ex. 89 | Compound-148/ETM-1 | 3.38 | 898 | 8.98 | 8.34 | 241 hours |
| Ex. 90 | Compound-149/ETM-1 | 3.53 | 892 | 8.93 | 7.95 | 240 hours |
| Ex. 91 | Compound-150/ETM-1 | 3.52 | 875 | 8.76 | 7.83 | 256 hours |
| Ex. 92 | Compound-151/ETM-1 | 3.56 | 891 | 8.91 | 7.87 | 279 hours |
| Ex. 93 | Compound-154/ETM-1 | 3.56 | 893 | 8.94 | 7.89 | 255 hours |
| Ex. 94 | Compound-155/ETM-1 | 3.39 | 874 | 8.74 | 8.10 | 251 hours |
| Ex. 95 | Compound-156/ETM-1 | 3.63 | 896 | 8.97 | 7.77 | 280 hours |
| Ex. 96 | Compound-157/ETM-1 | 3.51 | 887 | 8.89 | 7.97 | 276 hours |
| Ex. 97 | Compound-158/ETM-1 | 3.56 | 873 | 8.71 | 7.68 | 277 hours |
| Ex. 98 | Compound-159/ETM-1 | 3.40 | 900 | 9.00 | 8.31 | 308 hours |
| Ex. 99 | Compound-160/ETM-1 | 3.71 | 843 | 8.40 | 7.13 | 296 hours |
| Ex. 100 | Compound-161/ETM-1 | 3.42 | 879 | 8.80 | 8.08 | 260 hours |
| Ex. 101 | Compound-164/ETM-1 | 3.58 | 890 | 8.91 | 7.81 | 241 hours |
| Ex. 102 | Compound-165/ETM-1 | 3.53 | 883 | 8.84 | 7.88 | 272 hours |
| Ex. 103 | Compound-166/ETM-1 | 3.48 | 893 | 8.94 | 8.08 | 289 hours |
| Ex. 104 | Compound-167/ETM-1 | 3.51 | 864 | 8.66 | 7.76 | 267 hours |
| Ex. 105 | Compound-168/ETM-1 | 3.38 | 890 | 8.91 | 8.29 | 294 hours |
| Ex. 106 | Compound-173/ETM-1 | 3.59 | 849 | 8.49 | 7.43 | 241 hours |
| Ex. 107 | Compound-175/ETM-1 | 3.69 | 888 | 8.89 | 7.59 | 251 hours |
| Ex. 108 | Compound-179/ETM-1 | 3.50 | 909 | 9.10 | 8.19 | 298 hours |
| Ex. 109 | Compound-180/ETM-1 | 3.47 | 857 | 8.58 | 7.78 | 261 hours |
| Ex. 110 | Compound-181/ETM-1 | 3.53 | 882 | 8.83 | 7.87 | 277 hours |
| Ex. 111 | Compound-182/ETM-1 | 3.47 | 894 | 8.95 | 8.11 | 292 hours |
| Ex. 112 | Compound-201/ETM-1 | 3.44 | 874 | 8.75 | 8.00 | 285 hours |
| Com.Ex. 1 | ETM-2/ETM-1 | 3.82 | 805 | 8.05 | 6.62 | 165 hours |
| Com.Ex. 2 | ETM-3/ETM-1 | 4.01 | 659 | 6.59 | 5.16 | 203 hours |

As shown in Tables 3 and 4, a current of 10 mA/cm² in terms of a current density was passed through the organic EL elements, and at that time, while the organic EL elements of Comparative Examples 1 and 2 including the compounds ETM-2 and ETM-3 of the structural formulas shown above, respectively, had a driving voltage of 3.82 to 4.01 V, the organic EL elements of Examples 58 to 112 had a lower driving voltage of 3.35 to 3.71 V. While the organic EL elements of Comparative Examples 1 and 2 had a luminous efficacy of 6.59 to 8.05 cd/A, the organic EL elements of Examples 58 to 112 had an improved luminous efficiency of 8.22 to 9.10 cd/A. While the organic EL elements of Comparative Examples 1 and 2 had a power efficiency of 5.16 to 6.62 lm/W, the organic EL elements of Examples 58 to 112 had a significantly improved power efficiency of 7.13 to 8.34 lm/W. While the organic EL elements of Comparative Examples 1 and 2 had an element lifespan (95% decay) of 165 to 203 hours, the organic EL elements of Examples 58 to 112 had a significantly longer lifespan of 240 to 308 hours.

It can be seen from the above that the organic EL elements of the present invention have excellent luminous efficacy and power efficiency as well as a longer lifespan, compared with elements including the compounds ETM-2 and ETM-3 having the structural formulae shown above.

INDUSTRIAL APPLICABILITY

The compound having a specific benzazole ring structure of the present invention has good electron-injecting properties and hole-blocking capability, and is stable in the form of a thin film, and the compound of the present invention is therefore an excellent compound for an organic EL element. An organic EL element prepared by using this compound can achieve high efficiency and also achieve a reduced driving voltage and hence improved durability. Thus, the organic EL element can be applied to uses such as home electric appliances and lighting equipment, for example.

The invention claimed is:

1. A compound having a benzazole ring structure and represented by the general formula (a-4):

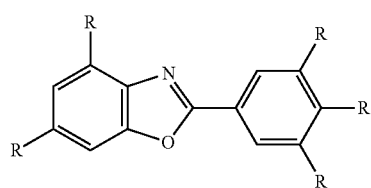

(a-4)

where a plurality of R are the same or different, and represent a group represented by the structural formula (b-1) below, a hydrogen atom, a substituted or unsubstituted aromatic hydrocarbon group, or a substituted or unsubstituted fused polycyclic aromatic group, at least one R is a group represented by the structural formula (b-1), and at least one other R is a phenyl group, a naphthyl group, a phenanthrenyl group, a spirobifluorenyl group, a pyridyl group, or a substituted or unsubstituted fluorenyl group, or a group obtained by combining any of these groups with a phenylene group:

(b-1)

where $L_1$ and $L_2$ are the same or different, and represent a single bond, a substituted or unsubstituted aromatic hydrocarbon group, a substituted or unsubstituted aromatic heterocyclic group, or a substituted or unsubstituted fused polycyclic aromatic group, n is an integer 1 or 2, and the dashed line indicates a binding site.

2. The compound having a benzazole ring structure as set forth in claim 1, represented by the general formula (a-5):

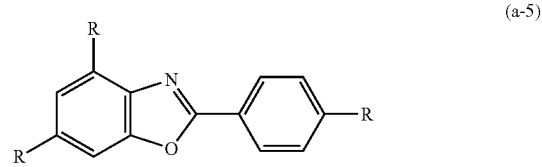

(a-5)

where R is as defined in the general formula (a-4).

3. The compound having a benzazole ring structure as set forth in claim 1, wherein n in the structural formula (b-1) is an integer 1.

4. The compound having a benzazole ring structure as set forth in claim 1, wherein $L_2$ in the structural formula (b-1) is a substituted or unsubstituted phenylene group or a substituted or unsubstituted biphenylene group.

5. An organic electroluminescent element comprising a pair of electrodes and one or more organic layers sandwiched therebetween, wherein the compound having a benzazole ring structure as set forth in claim 1 is included in at least one of the organic layers.

6. The organic electroluminescent element as set forth in claim 5, wherein the organic layer including the compound having a benzazole ring structure is an electron-transporting layer.

7. The organic electroluminescent element as set forth in claim 5, wherein the organic layer including the compound having a benzazole ring structure is a hole-blocking layer.

8. The organic electroluminescent element as set forth in claim 5, wherein the organic layer including the compound having a benzazole ring structure is a light-emitting layer.

9. The organic electroluminescent element as set forth in claim 5, wherein the organic layer including the compound having a benzazole ring structure is an electron-injecting layer.

* * * * *